US007695968B2

(12) United States Patent
Karchi et al.

(10) Patent No.: US 7,695,968 B2
(45) Date of Patent: Apr. 13, 2010

(54) NUCLEOTIDE SEQUENCES REGULATING GENE EXPRESSION AND CONSTRUCTS AND METHODS UTILIZING SAME

(75) Inventors: Hagai Karchi, Doar-Na Emek Soreq (IL); Rafael Meissner, Rechovot (IL); Gil Ronen, Emeq-Hefer (IL); Ezekiel Golan, Tel Aviv (IL); Larisa Rabinovich, Rishon LeZion (IL); Naama Zeliger, Moshav Mechora (IL); Noa Savir, Kibbutz Givat-Brener (IL)

(73) Assignee: Evogene Ltd., Rechovot (IL)

( * ) Notice: Subject to any disclaimer, the term of this patent is extended or adjusted under 35 U.S.C. 154(b) by 216 days.

(21) Appl. No.: 10/548,548

(22) PCT Filed: Mar. 11, 2004

(86) PCT No.: PCT/IL2004/000235

§ 371 (c)(1),
(2), (4) Date: Sep. 12, 2005

(87) PCT Pub. No.: WO2004/081173

PCT Pub. Date: Sep. 23, 2004

(65) Prior Publication Data

US 2007/0022503 A1 Jan. 25, 2007

Related U.S. Application Data

(60) Provisional application No. 60/453,843, filed on Mar. 12, 2003.

(51) Int. Cl.
*C12N 15/82* (2006.01)
*C12N 15/63* (2006.01)

(52) U.S. Cl. ............... 435/419; 435/252.3; 435/320.1; 536/24.1; 800/278

(58) Field of Classification Search .................. None
See application file for complete search history.

(56) References Cited

U.S. PATENT DOCUMENTS

| | | | |
|---|---|---|---|
| 4,761,367 A | 8/1988 | Edgell et al. | |
| 6,177,611 B1 | 1/2001 | Rice | |
| 6,359,196 B1 | 3/2002 | Lok et al. | |
| 6,363,399 B1 | 3/2002 | Maslyn et al. | |
| 6,403,862 B1 | 6/2002 | Jiao et al. | |
| 7,034,204 B2 | 4/2006 | Conner et al. | |
| 2002/0029394 A1 | 3/2002 | Allen et al. | |
| 2004/0121360 A1 | 6/2004 | Karchi et al. | |
| 2007/0022503 A1 | 1/2007 | Karchi et al. | |

FOREIGN PATENT DOCUMENTS

| WO | WO 95/04830 | 2/1995 |
|---|---|---|
| WO | WO 00/29594 | 5/2000 |
| WO | WO 01/20024 | 3/2001 |
| WO | WO 01/55371 | 8/2001 |
| WO | WO 02/16655 | 2/2002 |
| WO | WO/02/16655 | * 2/2002 |
| WO | WO 02/079487 | 10/2002 |
| WO | WO 2004/081173 | 9/2004 |

OTHER PUBLICATIONS

Liu et al 1995 The Plant Journal 7(2): 351-358.*
Sato et al 2000 DNA Research 7: 131-135.*
Sato et al 1999 NCBI Locus AB022220, National LIbrary of Medicine, NIH Bethesda, Maryland USA.*
Schuler et al. "A Gene Map of the Human Genome", Science, 274: 540-546, 1996.
Seki et al. "Rapid Construction of A Transcription Map for A Cosmid Contig of *Arabidopsis thaliana* Genome Using A Novel cDNA Selection Method", The Plant Journal, 12(2): 481-487, 1997.
"*Arabidopsis thaliana* DNA Chromosome 3, BAC Clone T22E16", Database EMBL [Online], Retrieved From EBI Accession No. EM_PRO: AL132975, 1999. 100% Identity With SEQ ID No. 1.
"*Arabidopsis thaliana* T-DNA Flanking Sequence GK-125F03-012814", Database EMBL [Online], Retrieved From EBI Accession No. EM_PRO: AL764424, 2002. The Sequence Has 96.3% Identity With SEQ ID No. 1 in the Region From Nt 410-Nt 818.
"SALK_003991 *Arabidopsis thaliana* TDNA Insertion Lines *Arabidopsis thaliana* Genomic Clone SALK_003991, DNA Sequence", Database EMBL [Online], Retrieved From EBI Accession No. EM_PRO: BH171252, 2001. The Sequence Is 100% Identical With SEQ ID No. 1 in the Region From Nt 1285-Nt 1479.
Werner "The Promoter Connection", Nature Genetics, 29: 105-106, 2001.
Scherf et al. "First Pass Annotation of Promoters on Human Chromosome 22", Genome Research, 11: 333-340, 2001.
Brander et al. "A Pollen-Specific DEAD-Box Protein Related to Translation Initiation Factor EIF-4A From Tobacco", Plant Molecular Biology, 27: 637-649, 1995.
Comella et al. "Fine Sequence Analysis of 60 Kb Around the *Arabidopsis thaliana* AtEm1 Locus on Chromosome III", Plant Molecular Biology, 41: 687-700, 1999.
Chiaromonte et al. "Association Between Divergence and Interspersed Repeats in Mammalian Noncoding Genomic DNA", Proc. Natl. Acad. Sci. USA, 98(25): 14503-14508, 2001.
Google "Definitions of CONTIG on the Web", Google Search, 2 P., 2007.
Hsieh et al. "Genomic Cloning and Promoter Analysis of Aortic Preferentially Expressed Gene-1", The Journal of Biological Chemistry, 274(20): 14344-14351, 1999.
Mette et al. "Transcriptional Silencing and Promoter Methylation Triggered by Double-Stranded RNA", The EMBO Journal, 19(19): 5194-5201, 2000.

(Continued)

*Primary Examiner*—David H Kruse

(57) ABSTRACT

Novel plant derived regulatory sequences and constructs and methods of using such sequences for directing expression of exogenous polynucleotide sequences in plants are provided.

12 Claims, 17 Drawing Sheets

OTHER PUBLICATIONS

Communication Pursuant to Article 94(3) EPC Dated Feb. 13, 2008 From the European Patent Office Re.: Application No. 04719565.6.
Communication Pursuant to Article 94(3) EPC Dated Jun. 23, 2008 From the European Patent Office Re.: Application No. 04719565.6.
Communication Pursuant to article 96(2) EPC Dated Oct. 10, 2006 From the European Patent Office Re.: Application No. 02717022.4.
Communication Pursuant to Article 96(2) EPC Dated Jul. 11, 2007 From the European Patent Office Re.: Application No. 02717022.4.
Examination Report Dated Oct. 3, 2007 From the Government of India, Patent Office Re.: Application No. 2604/CHENP/2005.
International Search Report Dated Jan. 9, 2003 From the International Searching Authority Re.: Application No. PCT/IL02/00267.
International Preliminary Examination Report Dated Jul. 6, 2004 From the International Preliminary Examining Authority Re.: Application No. PCT/IL02/00267.
International Preliminary Examination Report Dated Oct. 15, 2004 From the International Preliminary Examining Authority Re.: Application No. PCT/IL02/00267.
International Preliminary Report on Patentability Dated Oct. 6, 2005 From the International Bureau of WIPO Re.: Application No. PCT/IL2004/000235.
International Search Report Dated Sep. 1, 2005 From the International Searching Authority Re.: Application No. PCT/IL04/00235.
Official Action Dated Jul. 16, 2007 From the Israeli Patent Office Re.: Application No. 170792.
Official Action Dated Nov. 1, 2007 From the US Patent Office Re.: U.S. Appl. No. 10/471,606.
Official Action Dated Mar. 3, 2008 From the Australian Government, IP Australia Re.: Application No. 2004219858.
Official Action Dated Mar. 7, 2007 From the US Patent Office Re.: U.S. Appl. No. 10/471,606.
Official Action Dated Jul. 13, 2006 From the US Patent Office Re.: U.S. Appl. No. 10/471,606.
Official Action Dated Mar. 20, 2006 From the US Patent Office Re.: U.S. Appl. No. 10/471,606.
Official Action Dated May 21, 2008 From the US Patent Office Re.: U.S. Appl. No. 10/471,606.
Official Action Dated Aug. 24, 2006 From the Australian Government, IP Australia Re. Application No. 2002247942.
Supplementary European Search Report Dated May 7, 2004 From the European Patent Office Re.: Application No. 02717022.4.
Supplementary Partial European Search Report Dated Jun. 12, 2006 From the European Patent Office Re.: Application No. 04719565.6.
Written Opinion Dated Sep. 1, 2005 From the International Searching Authority Re.: Application No. PCT/IL04/00235.
Written Opinion Dated Nov. 12, 2003 From the International Preliminary Examining Authority Re.: Application No. PCT/IL02/00267.
Communication Pursuant to Article 94(3) EPC Dated Nov. 5, 2008 From the European Patent Office Re.: Application No. 04719565.6.
Office Action Dated Nov. 4, 2008 From the Israeli Patent Office Re.: Application No. 170792 and Its Translation Into English.
GenBank "FTP Directory", FTP Directory/Repository/UniGene/at ftp.ncbi.nih.gov, UniGene, 6 P., 2003.
GenBank "*Zea mays*", Unigene Build #30, 2003.
Liu et al. "Generation of a High-Quality P1 Library of Arabidopsis Suitable for Chromosome Walking", The Plant Journal, 7(2): 351-358, 1995.
Sato et al. "*Arabidopsis thaliana* Genomic DNA, Chromosome 3 P1 Clone: MLN21", NCBI Locus AB022220, National Library of Medicine, 32 P., 1999.
Sato et al. "Structural Analysis of *Arabidopsis thaliana* Chromosome 3. I. Sequence Features of the Regions of 4,504,864 BP Covered by Sixty P1 and TAC Clones", DNA Research, 7(2): 131-135, 2000.
Schuler "Pieces of the Puzzle: Expressed Sequence Tags and the Catalog of Human Genes", Journal of Molecular Medicine, 75: 694-698, 1997.

* cited by examiner

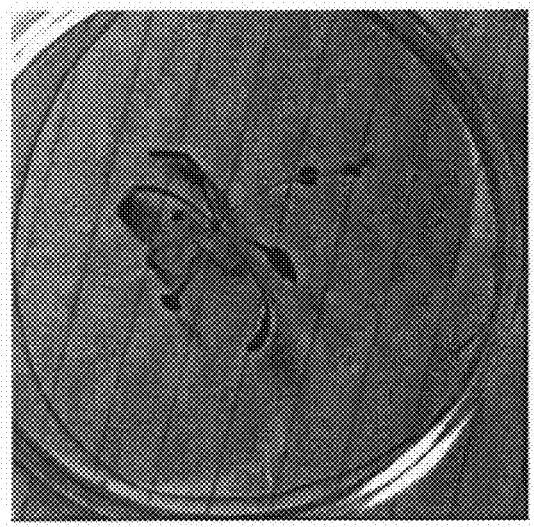 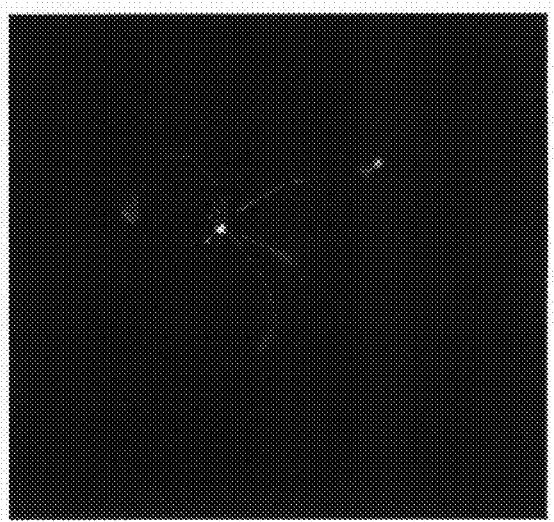
Fig. 11a  Fig. 11b
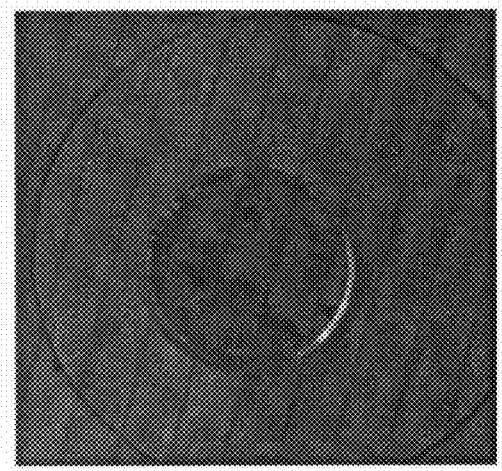 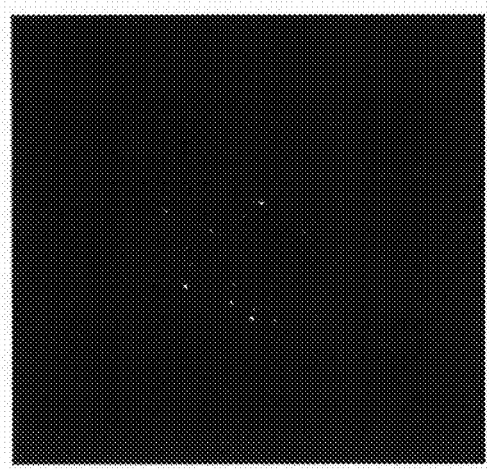
Fig. 12a  Fig. 12b

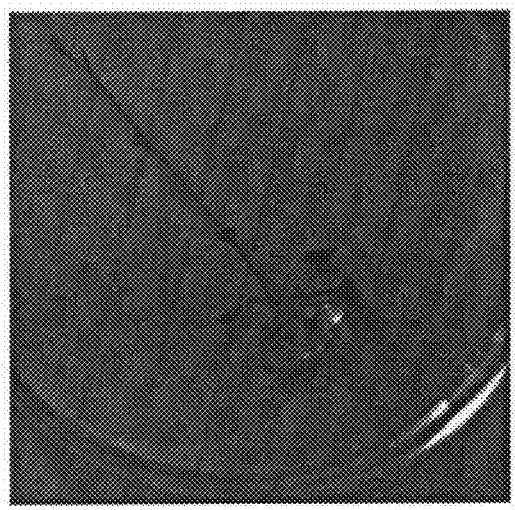 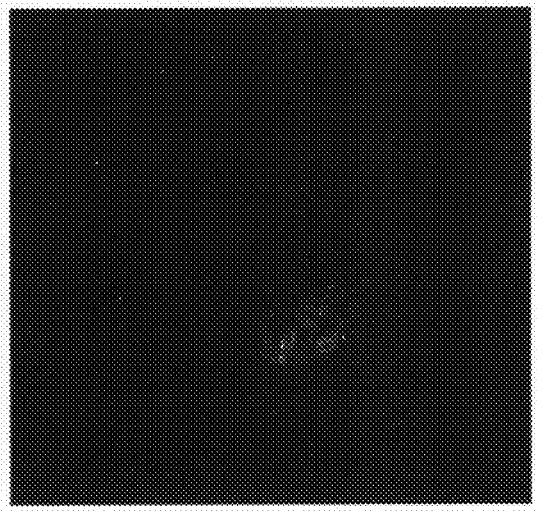
Fig. 13a    Fig. 13b
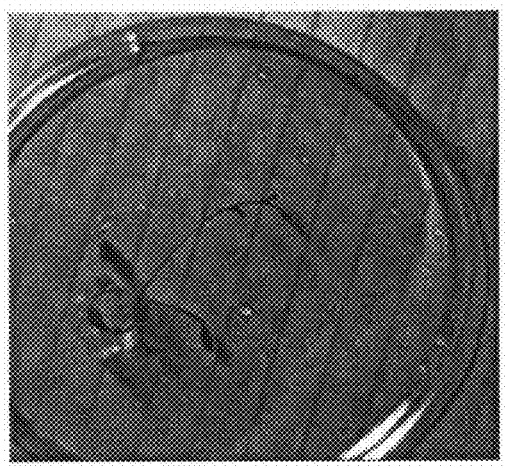 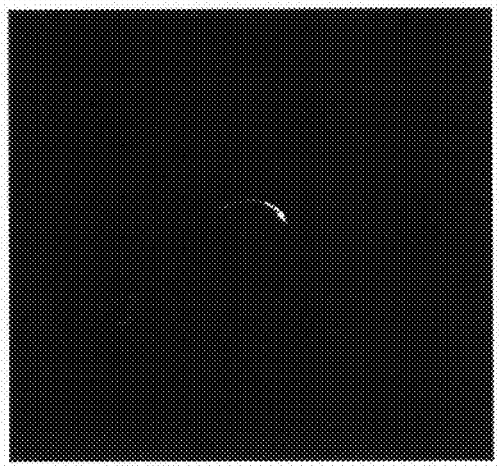
Fig. 14a    Fig. 14b

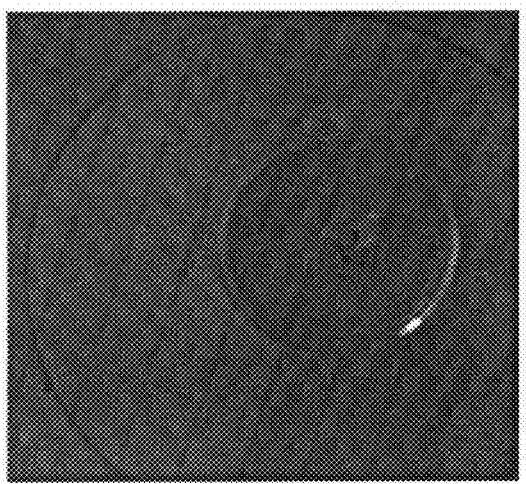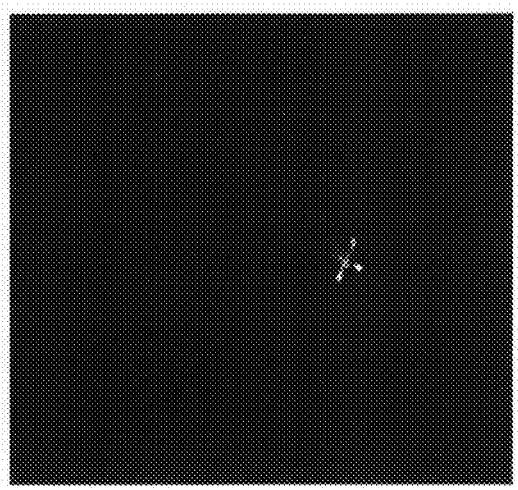
Fig. 17a     Fig. 17b
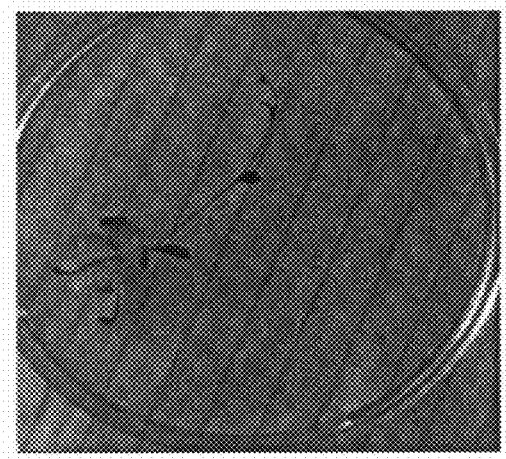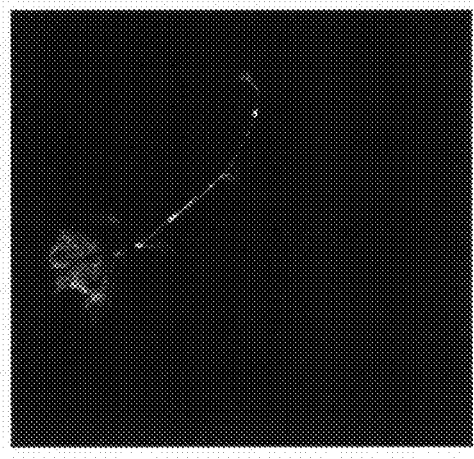
Fig. 18a     Fig. 18b

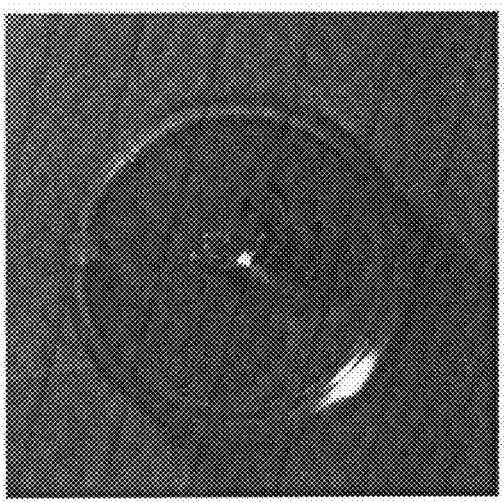
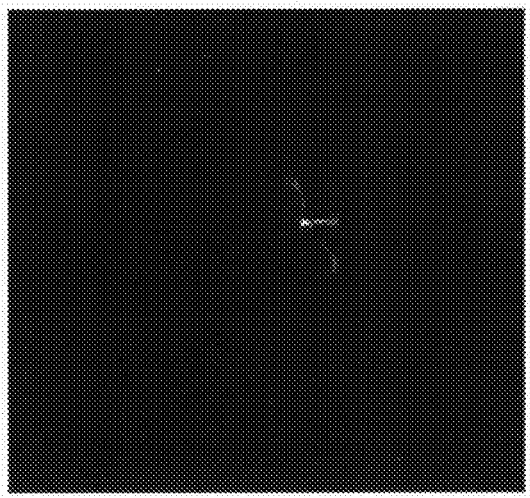
Fig. 19a  Fig. 19b
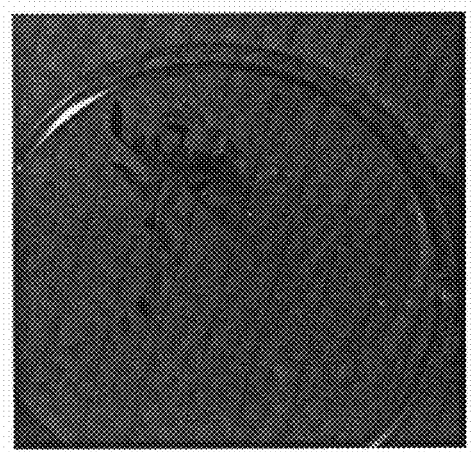
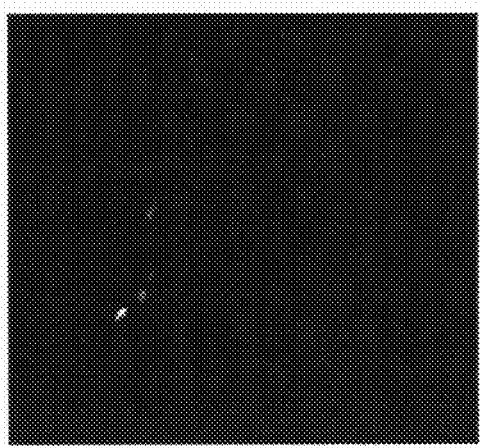
Fig. 20a  Fig. 20b

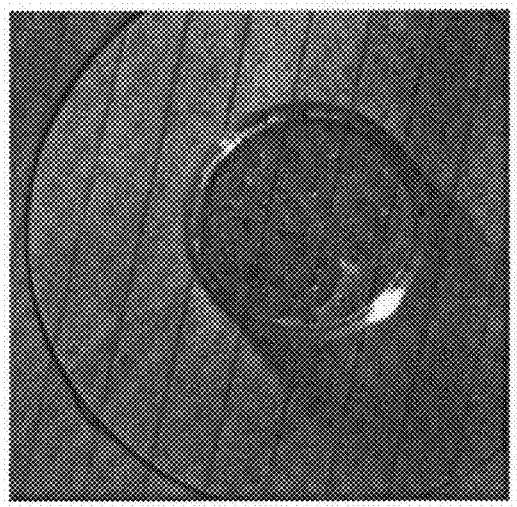 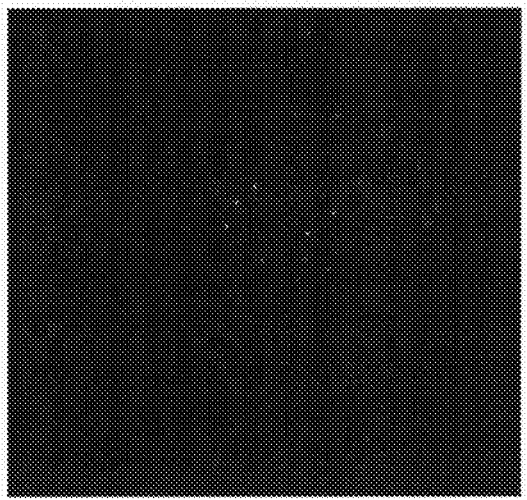
Fig. 21a　　　　Fig. 21b
 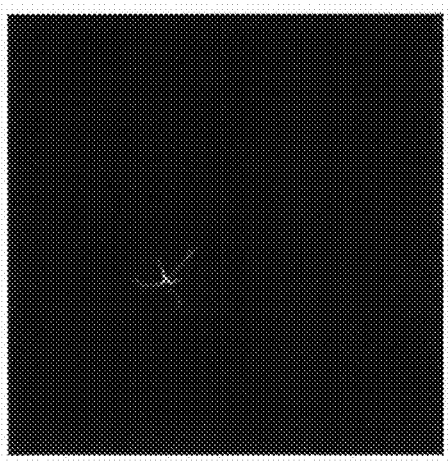
Fig. 22a　　　　Fig. 22b

```
Score = 1388 bits (722), Expect = 0.0
Identities = 722/722 (100%)
Strand = Plus / Plus Query: 1570 gacataaactatgctgtcaaaatgtgtagaatcttttacataaatcattccctgttaca 1629
              |||||||||||||||||||||||||||||||||||||||||||||||||||||||||||
Sbjct: 1168 gacataaactatgctgtcaaaatgtgtagaatcttttacataaatcattccctgttaca 1227

Query: 1630 cactaaaaggttcacaacggacgattgtattggacttccagatcataaaccatgcaaaac 1689
              ||||||||||||||||||||||||||||||||||||||||||||||||||||||||||||
Sbjct: 1228 cactaaaaggttcacaacggacgattgtattggacttccagatcataaaccatgcaaaac 1287

Query: 1690 tgaaaaccacaagaataattagttctaactttagaacgttcgtacgtgtttcatgttcaa 1749
              ||||||||||||||||||||||||||||||||||||||||||||||||||||||||||||
Sbjct: 1288 tgaaaaccacaagaataattagttctaactttagaacgttcgtacgtgtttcatgttcaa 1347

Query: 1750 aaagcgtcaattataaaagttgggaaattacttttgagttttgacattctaaggacagt 1809
              |||||||||||||||||||||||||||||||||||||||||||||||||||||||||||
Sbjct: 1348 aaagcgtcaattataaaagttgggaaattacttttgagttttgacattctaaggacagt 1407

Query: 1810 caaatatgacaacattgggatgcaacttaccttgtattaacttatttgttataaaacca 1869
              |||||||||||||||||||||||||||||||||||||||||||||||||||||||||||
Sbjct: 1408 caaatatgacaacattgggatgcaacttaccttgtattaacttatttgttataaaacca 1467

Query: 1870 tatattacatattttaaagggttgataaataatcaaatataccaaaacatagcttttcaa 1929
              ||||||||||||||||||||||||||||||||||||||||||||||||||||||||||||
Sbjct: 1468 tatattacatattttaaagggttgataaataatcaaatataccaaaacatagcttttcaa 1527

Query: 1930 tatatttgtaaaacacgtttggtctactagctaattatgagaacatttgttcaatgcatg 1989
              ||||||||||||||||||||||||||||||||||||||||||||||||||||||||||||
Sbjct: 1528 tatatttgtaaaacacgtttggtctactagctaattatgagaacatttgttcaatgcatg 1587

Query: 1990 attatctagtatctactagtggattatgaaaattagatattttcattgcatgattatctt 2049
              ||||||||||||||||||||||||||||||||||||||||||||||||||||||||||||
Sbjct: 1588 attatctagtatctactagtggattatgaaaattagatattttcattgcatgattatctt 1647

Query: 2050 ccatatatagtgataacatcaaaagaatctacaccaattattgcatttttcattatata 2109
              |||||||||||||||||||||||||||||||||||||||||||||||||||||||||||
Sbjct: 1648 ccatatatagtgataacatcaaaagaatctacaccaattattgcatttttcattatata 1707

Query: 2110 ataagcactaaactgtaaaattatattcagccacccaaaccatgacaaatcaccttaaag 2169
              ||||||||||||||||||||||||||||||||||||||||||||||||||||||||||||
Sbjct: 1708 ataagcactaaactgtaaaattatattcagccacccaaaccatgacaaatcaccttaaag 1767

Query: 2170 gcttaaacacataacagccattacgagtcacaggtaagggtataatagtaaagaatcaat 2229
              ||||||||||||||||||||||||||||||||||||||||||||||||||||||||||||
Sbjct: 1768 gcttaaacacataacagccattacgagtcacaggtaagggtataatagtaaagaatcaat 1827
```

Fig. 27a

| Fig. 27a |
| --- |
| Fig. 27b |
| Fig. 27c |
| Fig. 27d |

Fig. 27

```
Query:  2230  ctatataatatacgacccacccttctcattctttctggagagtaacatcgagacaaaga  2289
              ||||||||||||||||||||||||||||||||||||||||||||||||||||||||||||
Sbjct:  1828  ctatataatatacgacccacccttctcattctttctggagagtaacatcgagacaaaga  1887

Query:  2290  ag  2291
              ||
Sbjct:  1888  ag  1889
Score = 1136 bits (591), Expect = 0.0
Identities = 591/591 (100%)
 Strand = Plus / Plus Query:  943   gtagatatacacattgatttactacaaacgtatactactatccatcttcaactcttcgga  1002
              ||||||||||||||||||||||||||||||||||||||||||||||||||||||||||||
Sbjct:  541   gtagatatacacattgatttactacaaacgtatactactatccatcttcaactcttcgga  600

Query:  1003  atatgatttcgaaaaaactatgaagattaacgggtatcttaaacatgttaagatacaccg  1062
              ||||||||||||||||||||||||||||||||||||||||||||||||||||||||||||
Sbjct:  601   atatgatttcgaaaaaactatgaagattaacgggtatcttaaacatgttaagatacaccg  660

Query:  1063  gacaattttcatttagaagaattgatatgcaattaacaataaatagttgatgatctttta  1122
              ||||||||||||||||||||||||||||||||||||||||||||||||||||||||||||
Sbjct:  661   gacaattttcatttagaagaattgatatgcaattaacaataaatagttgatgatctttta  720

Query:  1123  gttttgaagatgtgcgttaagacttaagcgtgtggtaacaaggtgggactcgggcaacgc  1182
              ||||||||||||||||||||||||||||||||||||||||||||||||||||||||||||
Sbjct:  721   gttttgaagatgtgcgttaagacttaagcgtgtggtaacaaggtgggactcgggcaacgc  780

Query:  1183  aaagccttgtagagtccacttgctcaacttgtctttcttttatctcttttccaagtctca  1242
              ||||||||||||||||||||||||||||||||||||||||||||||||||||||||||||
Sbjct:  781   aaagccttgtagagtccacttgctcaacttgtctttcttttatctcttttccaagtctca  840

Query:  1243  agattcaatgaactccgtgtaacacaaacacgcccatagatgagctcatttttggtattt  1302
              ||||||||||||||||||||||||||||||||||||||||||||||||||||||||||||
Sbjct:  841   agattcaatgaactccgtgtaacacaaacacgcccatagatgagctcatttttggtattt  900

Query:  1303  ccaatattgccactccatgataatatcatctagggatggggttcatttattttgaaatct  1362
              ||||||||||||||||||||||||||||||||||||||||||||||||||||||||||||
Sbjct:  901   ccaatattgccactccatgataatatcatctagggatggggttcatttattttgaaatct  960

Query:  1363  caacaaatctcgtcgattctaacacacatgattgatttgtttacttacttgaaagttggc  1422
              ||||||||||||||||||||||||||||||||||||||||||||||||||||||||||||
Sbjct:  961   caacaaatctcgtcgattctaacacacatgattgatttgtttacttacttgaaagttggc  1020

Query:  1423  aactatctgggattaaaatttatcttttctactgctagctagaagcatctatatatgtt  1482
              ||||||||||||||||||||||||||||||||||||||||||||||||||||||||||||
Sbjct:  1021  aactatctgggattaaaatttatcttttctactgctagctagaagcatctatatatgtt  1080

Query:  1483  agcctaatacgtggaagatgtcattgctaataatggctaaagatgtgtatt  1533
              |||||||||||||||||||||||||||||||||||||||||||||||||||
Sbjct:  1081  agcctaatacgtggaagatgtcattgctaataatggctaaagatgtgtatt  1131
Score =  962 bits (500), Expect = 0.0
Identities = 500/500 (100%)
 Strand = Plus / Plus
```

Fig. 27b

```
Query: 403  ggttaaagaatgatgattcgattatagcctcaactagaagatacgtgtagtgcaggtgtg  462
            ||||||||||||||||||||||||||||||||||||||||||||||||||||||||||||
Sbjct: 1    ggttaaagaatgatgattcgattatagcctcaactagaagatacgtgtagtgcaggtgtg  60

Query: 463  tagttaactggtggtagtggcagacaaccagattaggagttaaataaagcctttagattt  522
            ||||||||||||||||||||||||||||||||||||||||||||||||||||||||||||
Sbjct: 61   tagttaactggtggtagtggcagacaaccagattaggagttaaataaagcctttagattt  120

Query: 523  gagagattgaaatattcgattggaacctttctagattttacagccatctaaaattagat  582
            ||||||||||||||||||||||||||||||||||||||||||||||||||||||||||||
Sbjct: 121  gagagattgaaatattcgattggaacctttctagattttacagccatctaaaattagat  180

Query: 583  gcagatcacctactaccattcaaaaatgaacaaaataatttcatttacattttcctagca  642
            ||||||||||||||||||||||||||||||||||||||||||||||||||||||||||||
Sbjct: 181  gcagatcacctactaccattcaaaaatgaacaaaataatttcatttacattttcctagca  240

Query: 643  taagatataataataaaatagtgctcattttaattacttttctaaatattttcgttatt  702
            ||||||||||||||||||||||||||||||||||||||||||||||||||||||||||||
Sbjct: 241  taagatataataataaaatagtgctcattttaattacttttctaaatattttcgttatt  300

Query: 703  ttaaattttgcttgtctatactctacagctcatttaataacggaaacaaaaataattgca  762
            ||||||||||||||||||||||||||||||||||||||||||||||||||||||||||||
Sbjct: 301  ttaaattttgcttgtctatactctacagctcatttaataacggaaacaaaaataattgca  360

Query: 763  gggatacggatgggtagctttcaaaacttacatcatcttctgtttcttgagatcaactat  822
            ||||||||||||||||||||||||||||||||||||||||||||||||||||||||||||
Sbjct: 361  gggatacggatgggtagctttcaaaacttacatcatcttctgtttcttgagatcaactat  420

Query: 823  ttttggagctttgtctcaatcgtaccaaaggataatggtcctacctccttttgcattctt  882
            ||||||||||||||||||||||||||||||||||||||||||||||||||||||||||||
Sbjct: 421  ttttggagctttgtctcaatcgtaccaaaggataatggtcctacctccttttgcattctt  480

Query: 883  aactttatcttctctactta  902
            ||||||||||||||||||||
Sbjct: 481  aactttatcttctctactta  500
CPU time:     0.06 user secs.        0.04 sys. secs        0.10 total secs.
```

Fig. 27c

```
Lambda      K        H
  1.33     0.621    1.12

Gapped
Lambda      K        H
  1.33     0.621    1.12

Matrix: blastn matrix:1 -2
Gap Penalties: Existence: 5, Extension: 2
Number of Hits to DB: 13
Number of Sequences: 0
Number of extensions: 13
Number of successful extensions: 6
Number of sequences better than 10.0: 1
length of query: 2316
length of database: 2,385,885,539
effective HSP length: 24
effective length of query: 2292
effective length of database: 2,385,885,515
effective search space: 5468449600380
effective search space used: 5468449600380
T: 0
A: 30
X1: 6 (11.5 bits)
X2: 26 (50.0 bits)
S1: 12 (23.8 bits)
S2: 20 (39.1 bits)
```

Fig. 27d

NUCLEOTIDE SEQUENCES REGULATING GENE EXPRESSION AND CONSTRUCTS AND METHODS UTILIZING SAME

RELATED PATENT APPLICATION

This application is a National Phase Application of PCT/IL2004/000235 having International Filing Date of 11 Mar. 2004, which claims the benefit of U.S. Provisional Patent Application No. 60/453,843 filed 12 Mar. 2003. The contents of the above Application are all incorporated herein by reference.

FIELD AND BACKGROUND OF THE INVENTION

The present invention relates to isolated polynucleotides which are capable of regulating gene expression in an organism and more specifically, to novel nucleic acid sequences which include constitutive, inducible, tissue-specific and developmental stage-specific promoters which are capable of directing gene expression in plants.

A promoter is a nucleic acid sequence approximately 200-1500 base pairs (bp) in length which is typically located upstream of coding sequences. A promoter functions in directing transcription of an adjacent coding sequence and thus acts as a switch for gene expression in an organism. Thus, all cellular processes are ultimately governed by the activity of promoters, making such regulatory elements important research and commercial tools.

Promoters are routinely utilized for heterologous gene expression in commercial expression systems, gene therapy and a variety of research applications.

The choice of the promoter sequence determines when, where and how strongly the heterologous gene of choice is expressed. Accordingly, when a constitutive expression throughout an organism is desired, a constitutive promoter is preferably utilized. On the other hand, when triggered gene expression is desired, an inductive promoter is preferred. Likewise, when an expression is to be confined to a particular tissue, or a particular physiological or developmental stage, a tissue specific or a stage specific promoter is respectively preferred.

Constitutive promoters are active throughout the cell cycle and have been utilized to express heterologous genes in transgenic plants, such that the expression of traits encoded by the heterologous genes is effected throughout the plant at all time. Examples of known constitutive promoters often used for plant transformation include the cauliflower heat shock protein 80 (hsp80) promoter, 35S cauliflower mosaic virus promoter, nopaline synthase (nos) promoter, octopine (ocs) *Agrobacterium* promoter and the mannopine synthase (mas) *Agrobacterium* promoter.

Inducible promoters can be switched on by an inducing agent and are typically active as long as they are exposed to the inducing agent. The inducing agent can be a chemical agent, such as a metabolite, growth regulator, herbicide, or phenolic compound, or a physiological stress directly imposed upon the plant such as cold, heat, salt, toxins, or through the action of a microbial pathogen or an insecticidal pest. Accordingly, inducible promoters can be utilized to regulate expression of desired traits, such as genes that control insect pests or microbial pathogens, whereby the protein is only produced shortly upon infection or first bites of the insect and transiently so as to decrease selective pressure for resistant insects. For example, plants can be transformed to express insecticidal or fungicidal traits such as the *Bacillus thuringiensis* (Bt) toxins, viruses coat proteins, glucanases, chitinases or phytoalexins. In another example, plants can be transformed to tolerate herbicides by overexpressing, upon exposure to a herbicide, the acetohydroxy acid synthease enzyme, which neutralizes multiple types of herbicides [Hattori, J. et al., Mol. General. Genet. 246: 419 (1995)].

Several fruit-specific promoters have been described, including an apple-isolated Thi promoter (U.S. Pat. No. 6,392,122); a strawberry-isolated promoter (U.S. Pat. No. 6,080,914); tomato-isolated E4 and E8 promoters (U.S. Pat. No. 5,859,330); a polygalacturonase promoter (U.S. Pat. No. 4,943,674); and the 2AII tomato gene promoter [Van Haaren et al., Plant Mol. Biol. 21: 625-640 (1993)]. Such fruit specific promoters can be utilized, for example, to modify fruit ripening by regulating expression of ACC deaminase which inhibits biosynthesis of ethylene. Other gene products which may be desired to express in fruit tissue include genes encoding flavor or color traits, such as thaumatin, cyclase or sucrose phosphate synthase.

Seed specific promoters have been described in U.S. Pat. Nos. 6,403,862, 5,608,152 and 5,504,200; and in U.S. patent application Ser. Nos. 09/998,059 and 10/137,964. Such seed specific promoters can be utilized, for example, to alter the levels of saturated or unsaturated fatty acids; to increase levels of lysine- or sulfur-containing amino acids, or to modify the amount of starch contained in seeds.

Several promoters which regulate gene expression specifically during germination stage have been described, including the α-glucoronidase and the cystatin-1 barely-isolated promoters (U.S. Pat. No. 6,359,196), and the hydrolase promoter [Skriver et al., Proc. Natl. Acad. Sci. USA, 88:7266-7270 (1991)].

While reducing the present invention to practice, the present inventors have uncovered several regulatory sequences which exhibit a wide range of promoter activities in plants, as is further described hereinunder, such regulatory sequences can be used in a variety of commercial and research applications.

SUMMARY OF THE INVENTION

According to one aspect of the present invention there is provided an isolated polynucleotide comprising a nucleic acid sequence selected from the group consisting of SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202, 211, 210 and 213, wherein the isolated polynucleotide is capable of regulating expression of at least one polynucleotide sequence operably linked thereto.

According to another aspect of the present invention there is provided a nucleic acid construct which includes the isolated polynucleotide comprising the nucleic acid sequence selected from the group consisting of SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202, 203, 210 and 213.

According to yet another aspect of the present invention there is provided a transgenic cell which includes the isolated polynucleotide comprising the nucleic acid sequence selected from the group consisting of SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202, 203, 210 and 213.

According to still another aspect of the present invention there is provided a transgenic cell comprising the nucleic acid construct which includes the isolated polynucleotide comprising the nucleic acid sequence selected from the group consisting of SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202, 203, 210 and 213.

According to an additional aspect of the present invention there is provided a transgenic organism which includes the isolated polynucleotide comprising the nucleic acid sequence selected from the group consisting of SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202, 203, 210 and 213.

According to yet an additional aspect of the present invention there is provided a transgenic organism comprising a nucleic acid construct which includes the isolated polynucleotide comprising the nucleic acid sequence selected from the group consisting of SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202, 203, 210 and 213.

According to still an additional aspect of the present invention there is provided a transgenic plant which includes the isolated polynucleotide comprising the nucleic acid sequence selected from the group consisting of SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202, 203, 210 and 213.

According to a further aspect of the present invention there is provided a transgenic plant comprising a nucleic acid construct which includes the isolated polynucleotide comprising the nucleic acid sequence selected from the group consisting of SEQ ID NOS: 1, 6, 11, 16, 21, 26, 31, 36, 41,46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202, 203, 210 and 213.

According to yet a further aspect of the present invention there is provided a method of producing a transgenic plant comprising transforming a plant with an isolated polynucleotide which includes a nucleic acid sequence selected from the group consisting of SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202, 203, 210 and 213.

According to still a further aspect of the present invention there is provided a method of producing a transgenic plant comprising transforming a plant with a nucleic acid construct which includes the isolated polynucleotide comprising the nucleic acid sequence selected from the group consisting of SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202, 203, 210 and 213.

According to still a further aspect of the present invention there is provided a method of expressing a polypeptide of interest in a cell comprising transforming the cell with a nucleic acid construct including a polynucleotide sequence encoding the polypeptide of interest operably linked to a regulatory nucleic acid sequence selected from the group consisting of SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202, 203, 210 and 213 thereby expressing the polypeptide of interest in the cell.

According to still a further aspect of the present invention there is provided a method of co-expressing two polypeptides of interest in a cell comprising transforming the cell with a nucleic acid construct including two polynucleotide sequences encoding the two polypeptides of interest operably linked to a regulatory nucleic acid sequence selected from the group consisting of SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202, 203, 210 and 213 such that said two polynucleotide sequences flank said regulatory nucleic acid sequence, thereby expressing the two polypeptides of interest in the cell.

According to further features in preferred embodiments of the invention described below, the isolated polynucleotide includes at least one promoter region.

According to still further features in the described preferred embodiments the nucleic acid sequence is selected from the group consisting of SEQ ID NOS: 1, 6, 41, 46, 51, 61, 86, 121, 136, 171, 181 and 202, and whereas the at least one promoter region is capable of directing transcription of said at least one polynucleotide sequence in a constitutive manner.

According to still further features in the described preferred embodiments the nucleic acid sequence is selected from the group consisting of SEQ ID NOS: 1, 11, 16, 21, 26, 31, 36, 56, 66, 71, 76, 81, 91, 96, 101, 116, 126, 141, 146, 151, 156, 161, 166, 176, 186, 191, 196, 201, 203, 210 and 213, and whereas the at least one promoter region is capable of directing transcription of said at least one polynucleotide sequence in an inductive manner.

According to still further features in the described preferred embodiments the nucleic acid sequence is selected from the group consisting of SEQ ID NOS: 1, 11, 16, 21, 26, 31, 36, 56, 61, 66, 71, 76, 91, 116, 126, 141, 146, 151, 156, 161, 166, 176, 186, 191, 196, 201, 203, 210 and 213, and whereas the at least one promoter region is capable of directing transcription of said at least one polynucleotide sequence in a tissue specific manner.

According to still further features in the described preferred embodiments the nucleic acid sequence is selected from the group consisting of SEQ ID NOS: 81, 96, 101, 106 and 131, and whereas the at least one promoter region is capable of directing transcription of said at least one polynucleotide sequence in a developmental stage specific manner.

According to still further features in the described preferred embodiments the nucleic acid construct further includes at least one heterologous polynucleotide operably linked to the isolated polynucleotide.

According to still further features in the described preferred embodiments the at least one heterologous polynucleotide is a reporter gene.

According to still further features in the described preferred embodiments the nucleic acid construct further includes two heterologous polynucleotides each being operably linked to an end of the isolated polynucleotide such that the two heterologous polynucleotides flank the isolated polynucleotide.

The present invention successfully addresses the shortcomings of the presently known configurations by providing a plurality of isolated polynucleotide sequences which exhibit a wide spectrum of promoter function patterns. These polynucleotides can be used to generate nucleic acid constructs, such as expression vectors suitable for transforming an organism. Such nucleic acid constructs can be used to promote expression of desired traits or expression products in transgenic organisms, such as plants, in a constitutive, induced, tissue specific, or a developmental stage specific manner.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a shows the transgenic plant under normal light. FIG. 1b is an ultra-low light photograph of the same plant in the dark, illustrating a specific expression luciferase in flower tissue.

FIG. 2a shows the transgenic plant under normal light. FIG. 2b is an ultra-low light photograph of the same plant in the dark, illustrating a specific expression of luciferase in root tissue.

FIG. 3a shows the transgenic plant under normal light. FIG. 3b is an ultra-low light photograph of the same plant in the dark, illustrating a specific expression of luciferase in root and flower tissue.

FIG. 4a shows the transgenic plant under normal light. FIG. 4b is an ultra-low light photograph of the same plant in the dark, illustrating a specific expression of luciferase in young tissue.

FIG. 5a shows the transgenic plant under normal light. FIG. 5b is an ultra-low light photograph of the same plant in the dark, illustrating an expression of luciferase in leaf tissue.

FIG. 6a shows the transgenic plant under normal light. FIG. 6b is an ultra-low light photograph of the same plant in the dark, illustrating an expression of luciferase in stem tissue.

FIG. 7a shows the transgenic plant under normal light. FIG. 7b is an ultra-low light photograph of the same plant in the dark, illustrating an expression of luciferase in above ground tissue.

FIG. 8a shows the transgenic plant under normal light. FIG. 8b is an ultra-low light photograph of the same plant in the dark, illustrating an expression of luciferase in flower tissue.

FIG. 9a shows the transgenic plant under normal light. FIG. 9b is an ultra-low light photograph of the same plant in the dark, illustrating a specific expression of luciferase in root and flower tissue.

FIG. 10a shows the transgenic plant under normal light. FIG. 10b is an ultra-low light photograph of the same plant in the dark, illustrating a specific expression of luciferase in above ground tissue.

FIGS. 11a-b are photographs showing an *Arabidopsis thaliana* mature plant transformed with a nucleic acid construct comprising the nucleic acid sequence set forth in SEQ ID NO: 96 operably linked to a luciferase encoding sequence. FIG. 11a shows the transgenic plant under normal light. FIG. 11b is an ultra-low light photograph of the same plant in the dark, illustrating a specific expression of luciferase in above ground tissue.

FIGS. 12a-b are photographs showing seeds of an *Arabidopsis thaliana* plant transformed with a nucleic acid construct comprising the nucleic acid sequence set forth in SEQ ID NO: 111 operably linked to a luciferase encoding sequence. FIG. 12a shows the seeds under normal light. FIG. 12b is an ultra-low light photograph of the same seeds in the dark, illustrating a specific expression of luciferase in seeds.

FIGS. 13a-b are photographs showing an *Arabidopsis thaliana* plant transformed with a nucleic acid construct comprising the nucleic acid sequence set forth in SEQ ID NO: 111 operably linked to a luciferase encoding sequence. FIG. 13a shows the transgenic plant under normal light. FIG. 13b is an ultra-low light photograph of the same plant in the dark, illustrating a specific expression of luciferase in roots.

FIGS. 14a-b are photographs showing an *Arabidopsis thaliana* plant transformed with a nucleic acid construct comprising the nucleic acid sequence set forth in SEQ ID NO: 121 operably linked to a luciferase encoding sequence. FIG. 14a shows the transgenic plant under normal light. FIG. 14b is an ultra-low light photograph of the same plant in the dark, illustrating a specific expression of luciferase in meristematic tissue.

FIG. 15a shows the transgenic plant under normal light. FIG. 15b is an ultra-low light photograph of the same plant in the dark, illustrating a specific expression of luciferase in root meristematic tissue.

FIG. 16*a* shows the transgenic plant under normal light. FIG. 16*b* is an ultra-low light photograph of the same plant in the dark, illustrating a specific expression of luciferase in flower meristematic tissue.

FIGS. 17*a-b* are photographs showing an *Arabidopsis thaliana* plant transformed with a nucleic acid construct comprising the nucleic acid sequence set forth in SEQ ID NO: 131 operably linked to a luciferase encoding sequence. FIG. 17*a* shows the transgenic plant under normal light. FIG. 17*b* is an ultra-low light photograph of the same plant in the dark, illustrating a specific expression of luciferase in leaf tissue.

FIGS. 18*a-b* are photographs showing an *Arabidopsis thaliana* plant transformed with a nucleic acid construct comprising the nucleic acid sequence set forth in SEQ ID NO: 136 operably linked to a luciferase encoding sequence. FIG. 18*a* shows the transgenic plant under normal light. FIG. 18*b* is an ultra-low light photograph of the same plant in the dark, illustrating a non-specific constitutive expression of luciferase.

FIGS. 19*a-b* are photographs showing an *Arabidopsis thaliana* seedling transformed with a nucleic acid construct comprising the nucleic acid sequence set forth in SEQ ID NO: 156 operably linked to a luciferase encoding sequence. FIG. 19*a* shows the transgenic plant under normal light. FIG. 19*b* is an ultra-low light photograph of the same plant in the dark, illustrating a specific expression of luciferase in above ground tissue.

FIGS. 20*a-b* are photographs showing an *Arabidopsis thaliana* mature plant transformed with a nucleic acid construct comprising the nucleic acid sequence set forth in SEQ ID NO: 156 operably linked to a luciferase encoding sequence. FIG. 20*a* shows the transgenic plant under normal light. FIG. 20*b* is an ultra-low light photograph of the same plant in the dark, illustrating a specific expression of luciferase in above ground tissue.

FIGS. 21*a-b* are photographs showing seeds of an *Arabidopsis thaliana* plant transformed with a nucleic acid construct comprising the nucleic acid sequence set forth in SEQ ID NO: 161 operably linked to a luciferase encoding sequence. FIG. 21*a* shows the seeds under normal light. FIG. 21*b* is an ultra-low light photograph of the same plant in the dark, illustrating a specific expression of luciferase in seed tissue.

FIGS. 22*a-b* are photographs showing an *Arabidopsis thaliana* plant transformed with a nucleic acid construct comprising the nucleic acid sequence set forth in SEQ ID NO: 186 operably linked to a luciferase encoding sequence. FIG. 22*a* shows the transgenic plant under normal light. FIG. 22*b* is an ultra-low light photograph of the same plant in the dark, illustrating an expression of luciferase in stalk and stem tissue.

FIG. 23*a* shows the transgenic plant under normal light. FIG. 23*b* is an ultra-low light photograph of the same plant in the dark, illustrating a weak expression of luciferase in vegetative tissue.

FIG. 24*a* shows the transgenic plant under normal light. FIG. 24*b* is an ultra-low light photograph of the same plant in the dark, illustrating an above ground tissue specific expression of luciferase.

FIG. 25*a* shows the transgenic plant under normal light. FIG. 25*b* is an ultra-low light photograph of the same plant in the dark, illustrating a specific expression of luciferase in flower tissue.

FIG. 26*a* shows a plant transformed with a nucleic acid construct including the nucleic acid sequence set forth in SEQ ID NO: 210 operably linked to a GUS encoding sequence. FIG. 26*b* shows root tips of a plant, transformed with a nucleic acid construct comprising the nucleic acid sequence set forth in SEQ ID NO: 213 operably linked to a GUS encoding sequence.

FIG. 27 is a nucleic acid sequence alignment between DRE 6669 (SEQ ID NO: 61, QUERY) and a prior art sequence (SEQ ID NO: 214, SBJCT), revealing a different 5' sequence which is important for constitutive expression, as is exemplified in the Examples section hereinbelow.

DESCRIPTION OF THE PREFERRED EMBODIMENTS

Figure 1A:
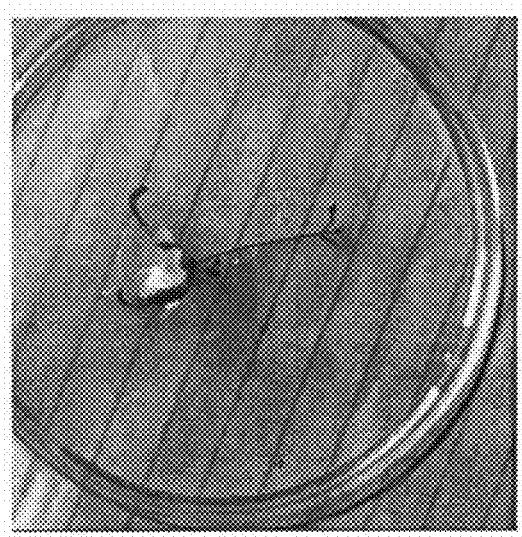
FIGS. 1a-b are photographs showing an *Arabidopsis thaliana* plant transformed with a nucleic acid construct comprising the nucleic acid sequence set forth in SEQ ID NO: 11 operably linked to a luciferase encoding sequence.
Figure 1B:
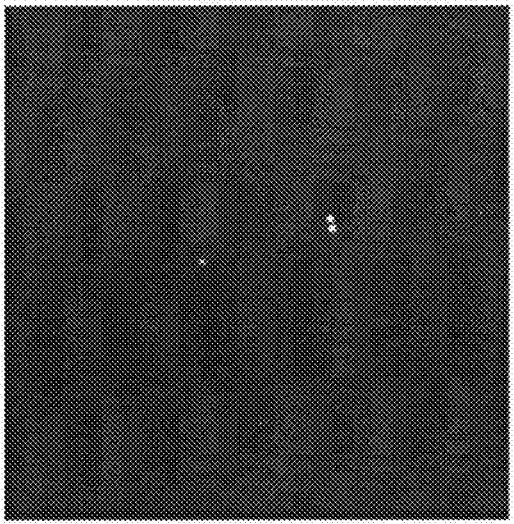
Figure 2A:
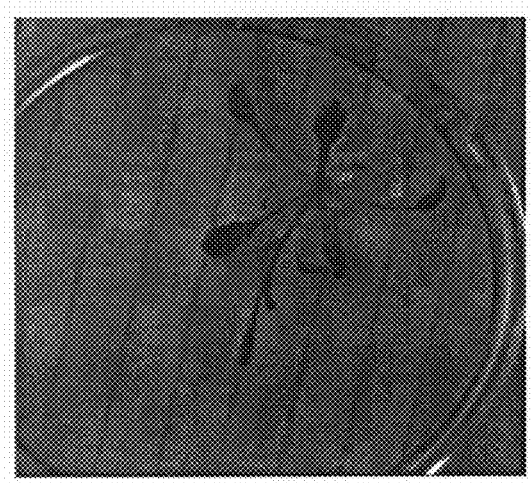
FIGS. 2a-b are photographs showing an *Arabidopsis thaliana* plant transformed with a nucleic acid construct comprising the nucleic acid sequence set forth in SEQ ID NO: 21 operably linked to a luciferase encoding sequence.
Figure 2B:
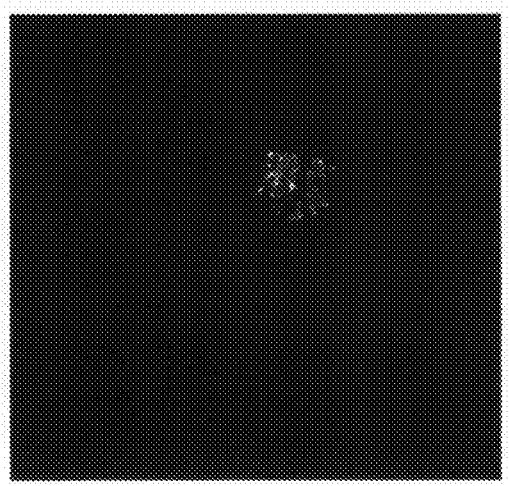
Figure 3A:
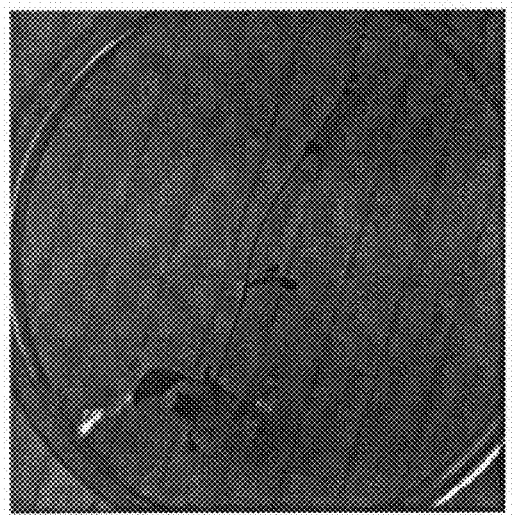
FIGS. 3a-b are photographs showing an *Arabidopsis thaliana* plant transformed with a nucleic acid construct comprising the nucleic acid sequence set forth in SEQ ID NO: 36 operably linked to a luciferase encoding sequence.
Figure 3B:
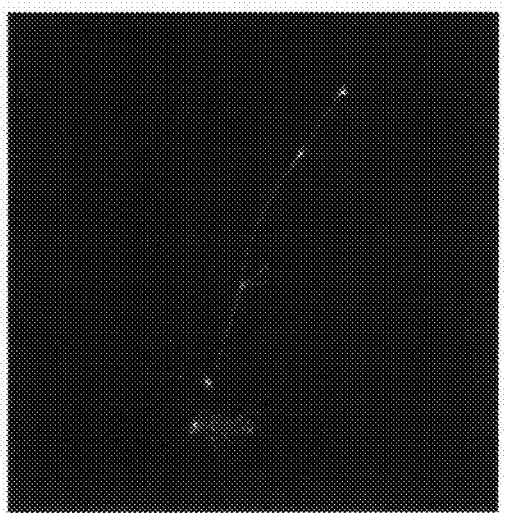
Figure 4A:
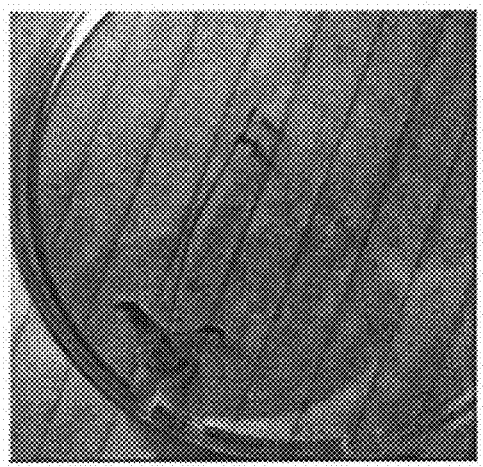
FIGS. 4a-b are photographs showing an *Arabidopsis thaliana* plant transformed with a nucleic acid construct comprising the nucleic acid sequence set forth in SEQ ID NO: 61 operably linked to a luciferase encoding sequence.
Figure 4B:
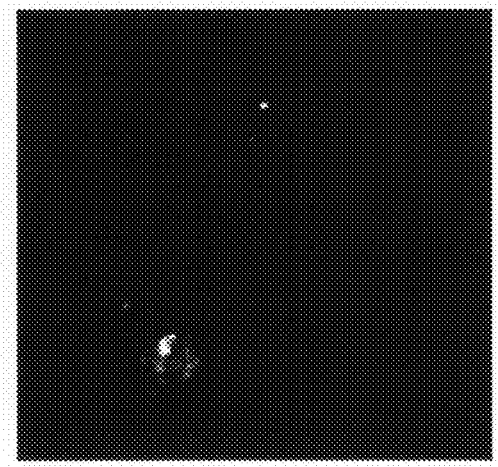
Figure 5A:
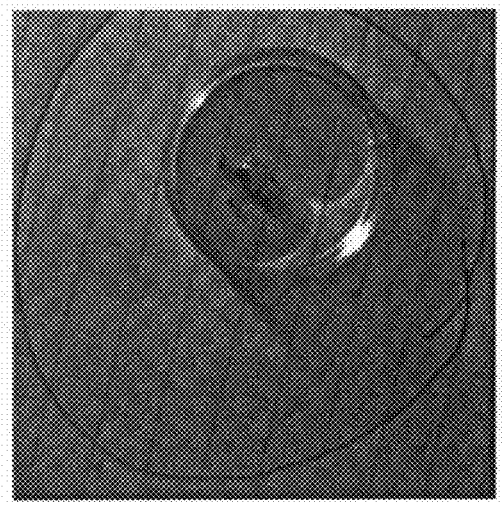
FIGS. 5a-b are photographs showing an *Arabidopsis thaliana* seedling transformed with a nucleic acid construct comprising the nucleic acid sequence set forth in SEQ ID NO: 66 operably linked to a luciferase encoding sequence.
Figure 5B:
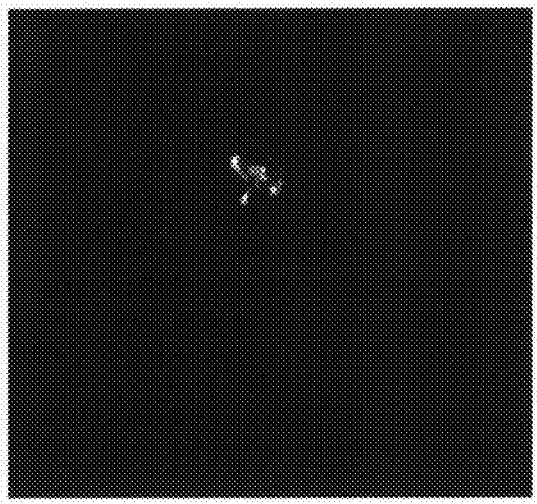
Figure 6A:
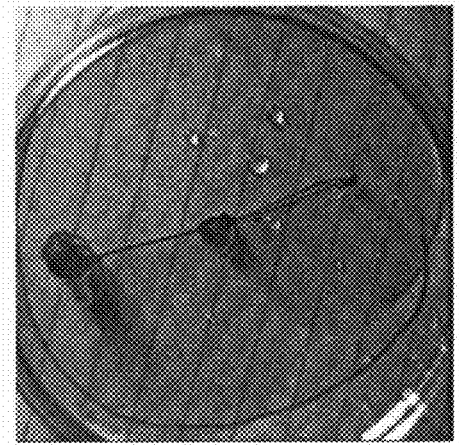
FIGS. 6a-b are photographs showing an *Arabidopsis thaliana* mature plant transformed with a nucleic acid construct comprising the nucleic acid sequence set forth in SEQ ID NO: 66 operably linked to a luciferase encoding sequence.
Figure 6B:
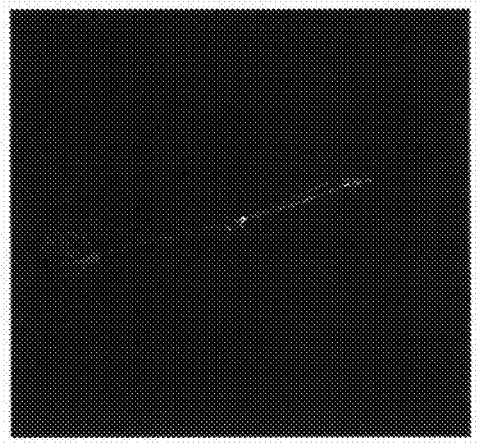
Figure 7A:
FIGS. 7a-b are photographs showing an *Arabidopsis thaliana* plant seedlings transformed with a nucleic acid construct comprising the nucleic acid sequence set forth in SEQ ID NO: 81 operably linked to a luciferase encoding sequence.
Figure 7B:
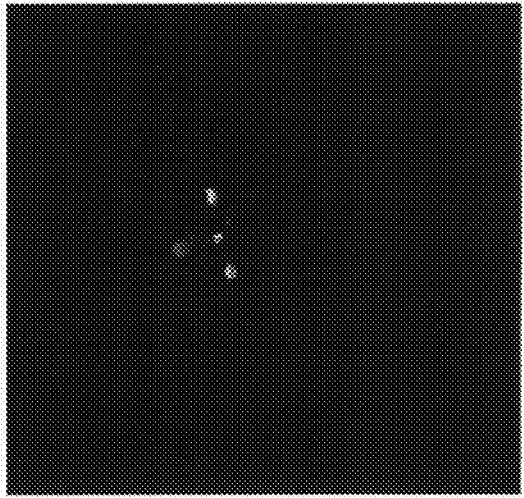
Figure 8A:
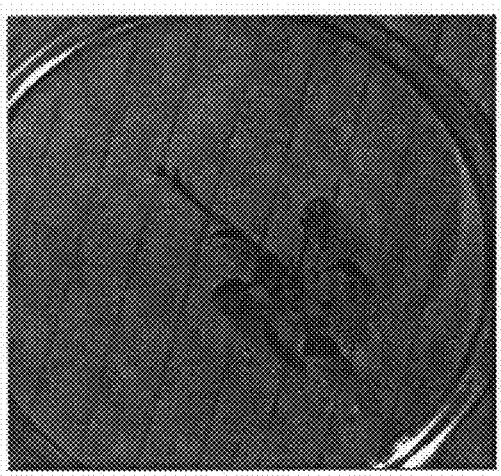
FIGS. 8a-b are photographs showing an *Arabidopsis thaliana* mature plant transformed with a nucleic acid construct comprising the nucleic acid sequence set forth in SEQ ID NO: 81 operably linked to a luciferase encoding sequence.
Figure 8B:
Figure 9A:
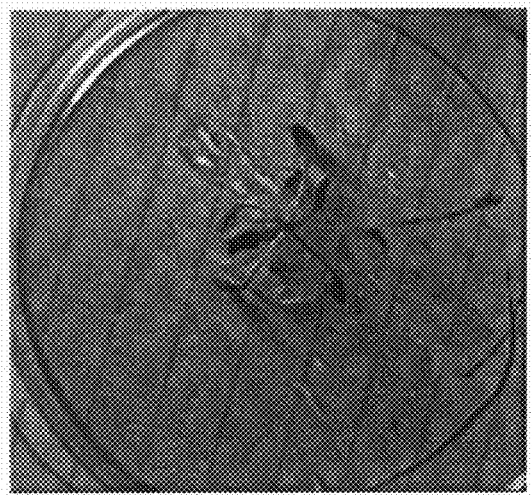
FIGS. 9a-b are photographs showing an *Arabidopsis thaliana* plant transformed with a nucleic acid construct comprising the nucleic acid sequence set forth in SEQ ID NO: 91 operably linked to a luciferase encoding sequence.
Figure 9B:
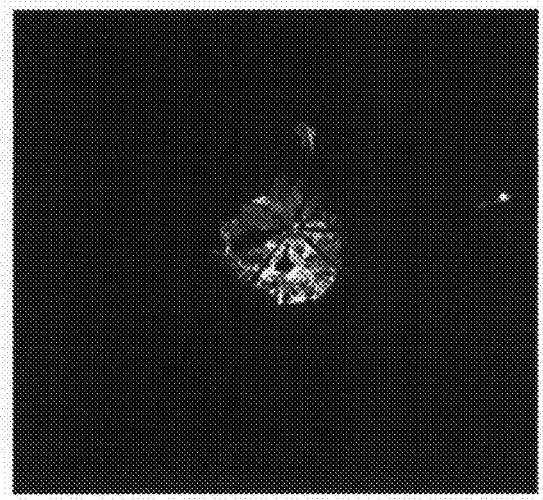
Figure 10A:
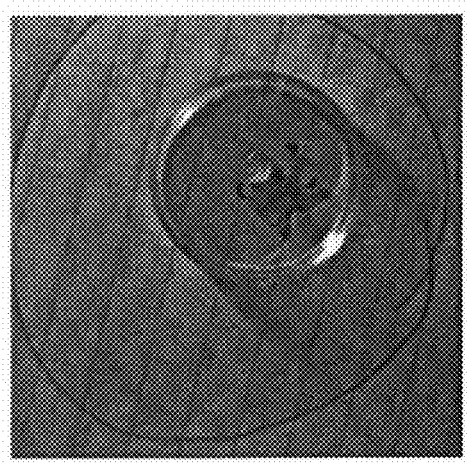
FIGS. 10a-b are photographs showing an *Arabidopsis thaliana* seedling transformed with a nucleic acid construct comprising the nucleic acid sequence set forth in SEQ ID NO: 96 operably linked to a luciferase encoding sequence.
Figure 10B:
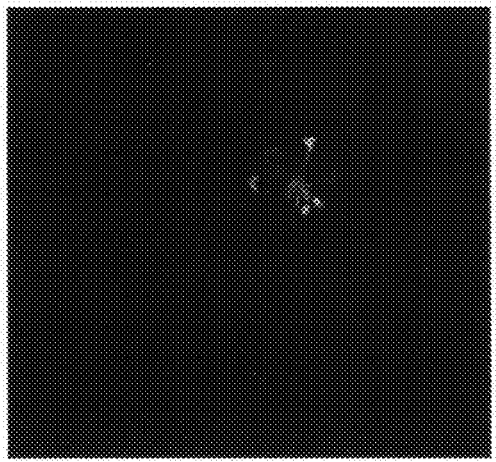
Figure 15A:
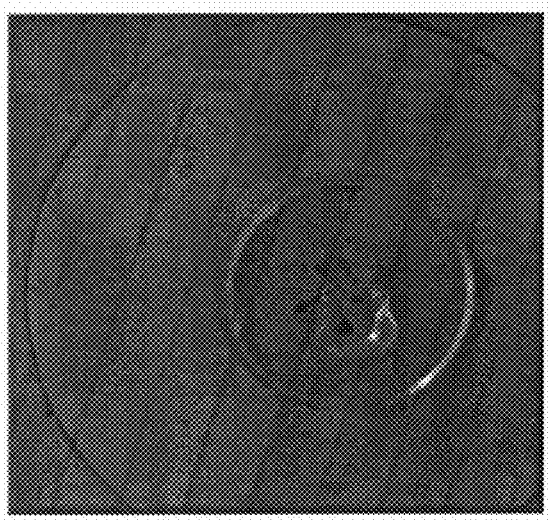
FIGS. 15a-b are photographs showing an *Arabidopsis thaliana* seedling transformed with a nucleic acid construct comprising the nucleic acid sequence set forth in SEQ ID NO: 126 operably linked to a luciferase encoding sequence.
Figure 15B:
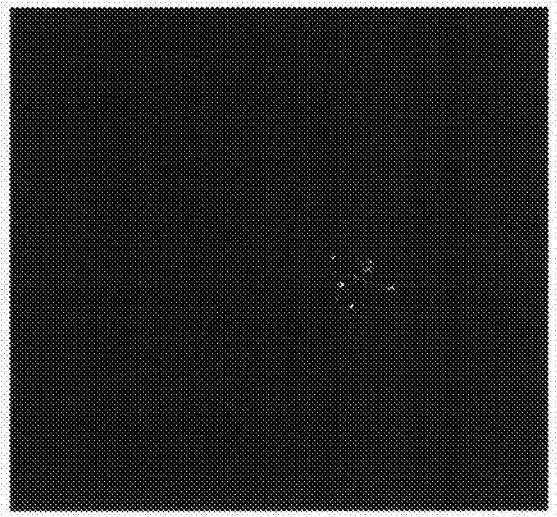
Figure 16A:
FIGS. 16*a-b* are photographs showing an *Arabidopsis thaliana* plant transformed with a nucleic acid construct comprising the nucleic acid sequence set forth in SEQ ID NO: 126 operably linked to a luciferase encoding sequence.
Figure 16B:
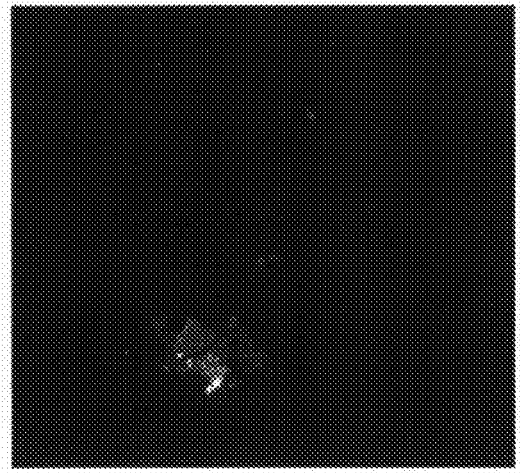
Figure 23A:
FIGS. 23*a-b* are photographs showing an *Arabidopsis thaliana* plant transformed with a nucleic acid construct comprising the nucleic acid sequence set forth in SEQ ID NO: 191 operably linked to a luciferase encoding sequence.
Figure 23B:
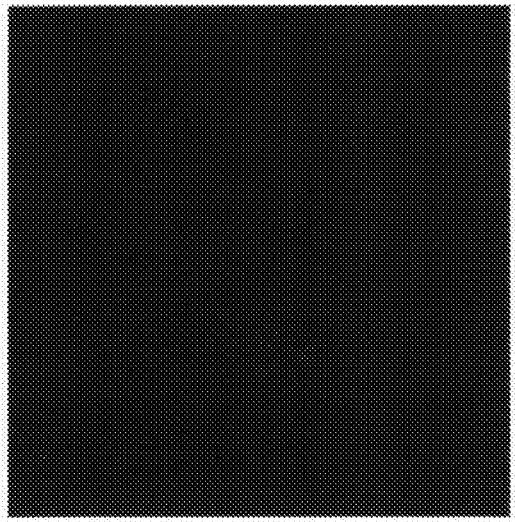
Figure 24A:
FIGS. 24*a-b* are photographs showing an *Arabidopsis thaliana* plant transformed with a nucleic acid construct comprising the nucleic acid sequence set forth in SEQ ID NO: 201 operably linked to a luciferase encoding sequence.
Figure 24B:
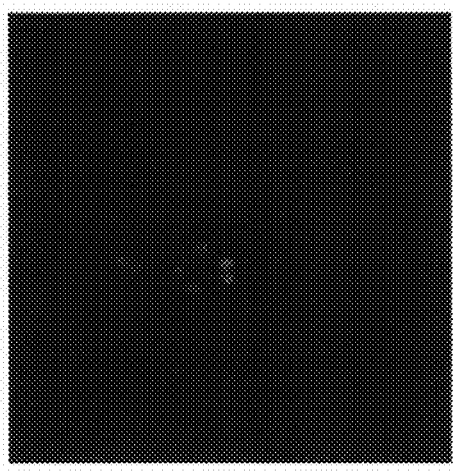
Figure 25A:
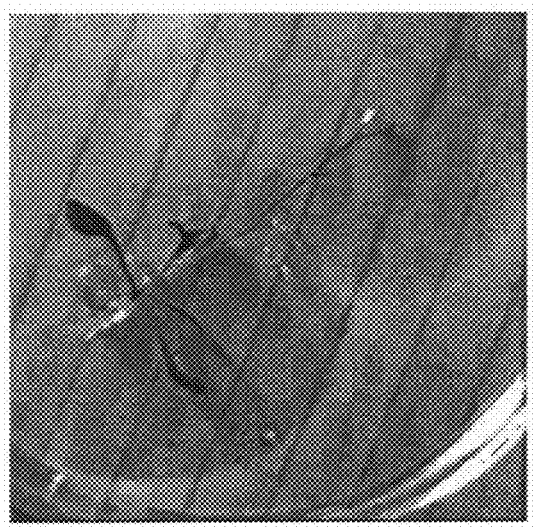
FIGS. 25*a-b* are photographs showing an *Arabidopsis thaliana* plant transformed with a nucleic acid construct comprising the nucleic acid sequence set forth in SEQ ID NO: 176 operably linked to a luciferase encoding sequence.
Figure 25B:

The present invention provides isolated polynucleotides capable of regulating the expression of operably linked heterologous polynucleotides, and more specifically, novel nucleic acid sequences which are capable of promoting gene expression in a constitutive, inductive, tissue specific and/or developmental stage specific manner. The present invention also provides nucleic acid constructs, as well transgenic organisms which carry the polynucleotides of the present invention and methods of producing thereof.

The principles and operation of the present invention may be better understood with reference to the accompanying descriptions.

Before explaining at least one embodiment of the invention in detail, it is to be understood that the invention is not limited in its application to the details of construction and the arrangement of the components set forth in the following descriptions or illustrated in the Examples section. The invention is capable of other embodiments or of being practiced or carried out in various ways. Also, it is to be understood that the phraseology and terminology employed herein is for the purpose of description and should not be regarded as limiting.

The term "polynucleotide" or the phrase "nucleic acid sequence" are used herein interchangeably and refer to a polymer of deoxyrebonucleotide (DNA) or ribonucleotide (RNA).

The phrase "heterologous polynucleotide" refers to a polynucleotide sequence which originates from a heterologous organism or to a polynucleotide sequence which is linked to a regulatory sequence of the same organism which does not normally regulate expression of the polynucleotide sequence in the organism.

PCT Publication WO 02/07989 describes a unique approach developed by the present inventors in order to uncover novel regulatory sequences in organisms such as plants. This approach combines molecular and bioinformatics techniques for high throughput isolation of DNA regulating elements (DREs), located within the non-transcribed (non-coding) regions of the genome and which include, for example, promoters, enhancers, suppressors, silencers, locus control regions and the like.

Utilizing this approach, the present inventors have uncovered several novel polynucleotide sequences which, as illustrated in the Examples section which follows, exhibit regulatory activity in plants.

Thus, according to one aspect of the present invention, there is provided isolated polynucleotides which are capable of regulating the expression of at least one polynucleotide operably linked thereto. As is further described in the Examples section which follows, these isolated polynucleotides are as set forth in SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202 and 203, or fragments (e.g., SEQ ID NOS: 210 and 213), variants or derivatives thereof.

A coding nucleic acid sequence is "operably linked" to a regulatory sequence if it is capable of exerting a regulatory effect on the coding sequence linked thereto. Preferably, the regulatory sequence is positioned 1-500 bp upstream of the ATG codon of the coding nucleic acid sequence, although it will be appreciated that regulatory sequences can also exert their effect when positioned elsewhere with respect to the coding nucleic acid sequence (e.g., within an intron).

As is clearly illustrated in the Examples section which follows, the isolated polynucleotides of the present invention are capable of regulating expression of a coding nucleic acid sequence (e.g., luciferase) operably linked thereto (see FIGS. 1-25).

The isolated polynucleotides of the present invention range in length from 174 to 3,348 nucleotides and include one or more sequence regions which are capable of recognizing and binding RNA polymerase II and other proteins (trans-acting transcription factors) involved in transcription.

Although most of the isolated polynucleotides described herein include one promoter region, some include two distinct promoter regions each positioned on a different strand of the same genomic sequence. Such bidirectional DREs are further described in the Examples section which follows (see for example, Tables 3-17).

As is further illustrated by the Examples section which follows, the isolated polynucleotides of the present invention exhibit a range of activities and tissue specificities.

Thus for example, the nucleic acid sequences set forth in SEQ ID NOS: 1, 6, 41, 46, 51, 61, 86, 121, 136, 171, 181 and 202 or fragment, variants or derivatives thereof, are capable of directing transcription of coding nucleic acid sequences operably linked thereto in a constitutive manner and thus include a constitutive promoter region.

In another example, the nucleic acid sequences set forth in SEQ ID NOS: 1, 11, 16, 21, 26, 31, 36, 56, 66, 71, 76, 81, 91, 96, 101, 116, 126, 141, 146, 151, 156, 161, 166, 176, 186, 191, 196, 201 and 203, or fragments (e.g., SEQ ID NOS: 210 and 213), variants or derivatives thereof, are capable of directing transcription of coding nucleic acid sequences operably linked thereto in an inductive manner and thus include an inductive promoter region.

In yet another example, the nucleic acid sequences set forth in SEQ ID NOS: 1, 11, 16, 21, 26, 31, 36, 56, 61, 66, 71, 76, 91, 116, 126, 141, 146, 151, 156, 161, 166, 176, 186, 191, 196, 201 and 203, or fragments (e.g., SEQ ID NOS: 210 and 213), variants or derivatives thereof, are capable of directing transcription of coding nucleic acid sequences operably linked thereto in a tissue specific manner and thus include a tissue specific promoter region.

In further yet another example, the nucleic acid sequences set forth in SEQ ID NOS: 81, 96, 101, 106 and 131, or fragment, variants or derivatives thereof, are capable of directing transcription of coding nucleic acid sequences operably linked thereto in a developmental stage specific manner and thus include a developmental stage specific promoter region.

Preferably, the polynucleotide of the present invention are modified to create variations in the molecule sequences such as to enhance their promoting activities, using methods known in the art, such as PCR-based DNA modification, or standard DNA mutagenesis techniques, or by chemically synthesizing the modified polynucleotides.

Accordingly, the sequences set forth in SEQ ID NOS: 1, 6, 11, 16, 21, 26, 31, 36, 41, 46, 56, 61, 66, 71, 76, 81, 86, 91, 96, 101, 106, 11, 116, 121, 126, 131, 136, 141, 146, 151, 156, 161, 166, 171, 176, 181, 186, 191, 196, 201, 202 and 203 may be truncated or deleted and still retain the capacity of directing the transcription of an operably linked DNA sequence (e.g., SEQ ID NOS: 210 and 213). The minimal length of a promoter region can be determined by systematically removing sequences from the 5' and 3'-ends of the isolated polynucleotide by standard techniques known in the art, including but not limited to removal of restriction enzyme fragments or digestion with nucleases. Consequently, any sequence fragments, portions, or regions of the disclosed polypeptide sequences of the present invention can be used as regulatory sequences. It will be appreciated that modified sequences (mutated, truncated and the like) can acquire different transcriptional properties such as the direction of different pattern of gene expression as compared to the unmodified element (e.g., SEQ ID NO: 61 as compared to SEQ ID NO: 213, see the Examples section which follows).

Optionally, the sequences set forth in SEQ ID NOS: 1, 6, 11, 16, 21, 26, 31, 36, 41, 46, 56, 61, 66, 71, 76, 81, 86, 91, 96, 101, 106, 111, 116, 121, 126, 131, 136, 141, 146, 151, 156, 161, 166, 171, 176, 181, 186, 191, 196, 201, 202 and 203 may be modified, for example for expression in a range of plant systems. In another approach, novel hybrid promoters can be designed or engineered by a number of methods. Many promoters contain upstream sequences which activate, enhance or define the strength and/or specificity of the promoter, such as described, for example, by Atchison [Ann. Rev. Cell Biol. 4:127 (1988)]. T-DNA genes, for example contain "TATA" boxes defining the site of transcription initiation and other upstream elements located upstream of the transcription initiation site modulate transcription levels [Gelvin In: Transgenic Plants (Kung, S.-D. and Us,R., eds, San Diego: Academic Press, pp.49-87, (1988)]. Another chimeric promoter combined a trimer of the octopine synthase (ocs) activator to the mannopine synthase (mas) activator plus promoter and reported an increase in expression of a reporter gene [Mm Ni et al., The Plant Journal 7:661 (1995)]. The upstream regulatory sequences of the polynucleotide sequences of present invention can be used for the construction of such chimeric or hybrid promoters. Methods for construction of variant promoters include, but are not limited to, combining control elements of different promoters or duplicating portions or regions of a promoter (see for example, U.S. Pat. Nos. 5,110, 732 and 5,097,025). Those of skill in the art are familiar with the specific conditions and procedures for the construction, manipulation and isolation of macromolecules (e.g., DNA molecules, plasmids, etc.), generation of recombinant organisms and the screening and isolation of genes, [see for example Sambrook et al., Molecular Cloning: A Laboratory Manual, Cold Spring Harbor Press, (1989); Mailga ei al., Methods in Plant Molecular Biology, Cold Spring Harbor Press, (1995); Birren et al., Genome Analysis: volume 1, Analyzing DNA, (1997); volume 2, Detecting Genes, (1998); volume 3, Cloning Systems, (1999); and volume 4, Mapping Genomes, (1999), Cold Spring Harbor, N.Y].

The polynucleotides of the present invention, or fragment, variants or derivatives thereof, can be incorporated into nucleic acid constructs, preferably expression constructs (i.e., expression vectors) which can be introduced and replicate in a host cell.

Thus, according to another aspect of the present invention there is a provided a nucleic acid construct which includes at least one of the polynucleotides of the present invention, or fragments, variants or derivatives thereof.

Preferably, the nucleic acid construct of the present invention includes at least one operably linked heterologous polynucleotide. More preferably, at least one operably linked reporter gene.

The phrase "reporter gene" used herein refers to a gene encoding a selectable, screenable or detectable phenotype.

Reporter genes which may be utilized in the present invention may include, but not limited to, LUX or LUC coding for luciferase, GUS coding for β-glucoronidase, GFP coding for green-fluorescent protein, or antibiotic or herbicide tolerance genes. A general review of suitable markers is found in Wilmink and Dons, Plant Mol. Biol. Reprt. 11:165-185 (1993).

Further preferably, the nucleic acid construct of the present invention includes at least one heterologous polynucleotide encoding a desirable trait or an expression product.

A desirable trait which may be utilized in this invention may include, but not limited to, any phenotype associated with organism's morphology, physiology, growth and development, yield, produce quality, nutritional enhancement, disease or pest resistance, or stress tolerance.

Alternatively, the heterologous polynucleotide can encode any naturally occurring or man-made recombinant protein, such as pharmaceutical proteins [e.g., growth factors and antibodies Schillberg Naturwissenschaften. (2003) April; 90(4):145-55] and food additives. It will be appreciated that molecular farming is a well-proven way of producing a range of recombinant proteins, as described in details in Ma Nat Rev Genet. 2003 Oct.; 4(10):794-805; Twyman Trends Biotechnol. 2003 Dec.; 21(12):570-8.

An expression product which may be utilized in this invention may include, but not limited to, pharmaceutical polypeptides, industrial enzymes, oils, dyes, flavors, biofuels, or industrial biopolymers.

In cases of bidirectional DREs, the nucleic acid construct of this invention may include two heterologous polynucleotides each being operably linked to an end of the isolated polynucleotide of this invention, such that the two heterologous polynucleotides flank the isolated polynucleotide of this invention.

The nucleic acid construct can be, for example, a plasmid, a bacmid, a phagemid, a cosmid, a phage, a virus or an artificial chromosome. Preferably, the nucleic acid construct of the present invention is a plasmid vector, more preferably a binary vector.

The phrase "binary vector" refers to an expression vector which carries a modified T-region from Ti plasmid, enable to be multiplied both in *E. coli* and in *Agrobacterium* cells, and usually comprising reporter gene(s) for plant transformation between the two boarder regions. A binary vector suitable for the present invention includes pBI2113, pBI121, pGA482, pGAH, pBIG, pBI101 (Clonetech), or a modification thereof such as pVER1 which is a modified pBI101 plasmid, where the GUS gene was replaced by the LucII gene from pGL3-Basic (Promega).

The nucleic acid construct of the present invention can be utilized to transform a host cell. Thus, according to another aspect of the present invention there is provided a transgenic cell, a transgenic organism or a transgenic plant which is transformed with an isolated polynucleotide of the present invention. Preferably the transgenic cell, the transgenic organism or the transgenic plant is transformed with the nucleic acid construct of the present invention.

As used herein, the terms "transgenic" or "transformed" are used interchangeably referring to a cell or an organism into which cloned genetic material has been transferred.

Methods of introducing nucleic acid constructs into a cell, an organism or a plant are well known in the art. Accordingly, suitable methods for introducing nucleic acid sequences into plants include, but are not limited to, bacterial infection, direct delivery of DNA (e.g., via PEG-mediated transformation, desiccation/inhibition-mediated DNA uptake, electroporation, agitation with silicon carbide fibers, and acceleration of DNA coated particles, such as described by Potrykus Ann. Rev. Plant Physiol. Plant Mol. Biol. 42:205-225 (1991).

Methods for specifically transforming dicots primarily use *Agrobacterium tumefaciens*. For example, transgenic plants reported include but are not limited to cotton (U.S. Pat. Nos. 5,004,863, 5,159,135, 5,518,908; and WO 97/43430), soybean [U.S. Pat. Nos. 5,569,834, 5,416,011; McCabe et al., Bio/Technology, 6:923 (1988); and Christou et al., Plant Physiol., 87:671, (1988)]; *Brassica* (U.S. Pat. No. 5,463,174), and peanut [Cheng et al., Plant Cell Rep., 15: 653, (1996)].

Similar methods have been reported in the transformation of monocots. Transformation and plant regeneration using these methods have been described for a number of crops including but not limited to asparagus [*Asparagus officinalis*; Bytebier et al., Proc. Natl. Acad. Sci. U.S.A., 84: 5345, (1987); barley (*Hordeum vulgarae*; Wan and Lemaux, Plant Physiol., 104: 37, (1994)]; maize [*Zea mays*; Rhodes, C. A., et al., Science, 240: 204, (1988); Gordon-Kamm, et al., Plant Cell, 2: 603, (1990); Fromm, et al., Bio/Technology, 8: 833, (1990); Koziel, et al., Bio/Technology, 11: 194, (1993)]; oats [*Avena sativa*; Somers, et al., Bio/Technology, 10: 1589, (1992)]; orchardgrass [*Dactylis glomerata*; Horn, et al., Plant Cell Rep., 7: 469, (1988); rice [*Oryza sativa*, including *indica* and *japonica* varieties, Toriyama, et al., Bio/Technology, 6: 10, (1988); Zhang, et al., Plant Cell Rep., 7: 379, (1988); Luo and Wu, Plant Mol. Biol. Rep., 6: 165, (1988); Zhang and Wu, Theor. Appl. Genet., 76: 835, (1988); Christou, et al., Bio/Technology, 9: 957, (1991); sorghum [*Sorghum bicolor*; Casas, A. M., et al., Proc. Natl. Acad. Sci. U.S.A., 90: 11212, (1993)]; sugar cane [*Saccharum* spp.; Bower and Birch, Plant J., 2: 409, (1992)]; tall fescue [*Festuca arundinacea*; Wang, Z. Y. et al., Bio/Technology, 10: 691, (1992)]; turfgrass [*Agrostis palustris*; Zhong et al., Plant Cell Rep., 13: 1, (1993)]; wheat [*Triticum aestivum*; Vasil et al., Bio/Technology, 10: 667, (1992); Weeks T., et al., Plant Physiol., 102: 1077, (1993); Becker, et al., Plant, J. 5: 299, (1994)], and alfalfa [Masoud, S. A., et al., Transgen. Res., 5: 313, (1996)]. It is apparent to those of skill in the art that a number of transformation methodologies can be used and modified for production of stable transgenic plants from any number of target crops of interest.

The transformed plants can be analyzed for the expression features conferred by the polynucleotides of the present invention, using methods known in the art for the analysis of transformed plants. A variety of methods are used to assess gene expression and determine if the introduced gene(s) is integrated, functioning properly, and inherited as expected.

Preferably, the promoters can are evaluated by determining the expression levels and the expression features of genes to which the promoters are operatively linked. A preliminary assessment of promoter function can be determined by a transient assay method using reporter genes, but a more definitive promoter assessment can be determined from the analysis of stable plants. Methods for plant analysis include but are not limited to Southern blots or northern blots, PCR-based approaches, biochemical analyses, phenotypic screening methods, field evaluations, and immunodiagnostic assays.

Preferably, the capacity of isolated polynucleotides of this invention to promote gene expression in plants is evaluated according to phenotypic expression of reporter genes using procedures as described in the Examples section that follows. Briefly, the expression of luciferase in transgenic *Arabidopsis* is determined and consistently classified by quantitatively scoring certain features of expression, such as the intensity, specificity, development stage and positioning of expression. Accordingly, a luciferase gene that is expressed in a constitutive manner would indicate a putative constitutive promoter activity of the isolated polynucleotide. Likewise, a luciferase gene that is expressed in an inductive, tissue specific or a development-stage specific manner, would respectively indicate a putative inductive, a tissue specific or a stage specific promoter activity.

Hence, the present invention provides a plurality of isolated polynucleotide sequences which exhibit a wide spectrum of promoter function patterns. These polynucleotides can be used to generate nucleic acid constructs, such as expression vectors suitable for transforming an organism. Such nucleic acid constructs can be used to promote expression of desired traits or expression products in transgenic organisms, such as plants, in a constitutive, induced, tissue specific, or a developmental stage specific manner.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" RL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Identification, Isolation and Characterization of DNA Regulating elements (DREs)

Novel DREs were identified by luciferase expression assay driven by bioinformatically identified DNA fragments from *Arabidopsis thaliana* genomic DNA. Positive DREs were fused upstream a reporter gene in a vector which was used to transform *Arabidopsis thaliana* plants. The reporter gene expression driven by these DREs was characterized.

Materials and Experimental Methods

Isolation of DREs: A high throughput method of cloning DNA regulating elements (DREs) using a single reaction tube, referred to herein as the "one-tube" method, was utilized in order to enable large scale production of DRE transformed plants. Accordingly, genomic DNA (gDNA) was extracted from leaves of *Arabidopsis thaliana* Col1 using DNAeasy Plant Mini Kit (Qiagen, Germany). Primers for PCR amplification of DREs were designed using PRIMER3© software and modified to contain restriction sites absent from the DRE sequence, for PCR product insertion into pVER1 binary plasmid, which is a pBI101 (clontech) modified plasmid, where the GUS reporter gene was replaced by LucII gene from pGL3-Basic (promega). Briefly, GUS gene was cut out of pBI101 using the blunt restriction enzymes Ecl136II and SmaI. The pGL-Basic plasmid [after eliminating the HindIII and BamHI sites, by digestion, fill-in using klenow fragment (Roche) and self ligating the plasmid, using T4 DNA ligase (Roche)] was cut SacI and XbaI and the LucII gene insert was inserted into pBluescript, digested with the same enzymes. The new plasmid was digested SmaI, as a result a blunt ends LucII gene was cut out. The LucII gene was inserted into The pBI plasmid instead of the GUS gene. To eliminate all possible read-through of the Nos-promoter, which regulates Kanamycin resistance gene on pBI101, a poly-A signal was added between the Nos-terminator and the LucII gene. Poly-A signal was amplified from pGL3-Basic using proof reading Taq polymerase PFU (Promega) and using primers 5'-aggtacttggagcggccgca-3' and 5'-tagagaaatgttctggcacctg-3'.

The Product was inserted into HindIII site on pVer1 after filling the overhang 5' ends, using Klenow fragment (Roche).

Polymerase chain reaction analyses were performed using Taq Expand Long Template PCR kit (Roche), according to the manufacturer's instructions, using as thermal cycle: 92° C./2 min→10×[94° C./10 min→55° C./30 sec→68° C./5 min]→18×[94° C./10 min 55° C./30 sec→68° C./5 min (+20 sec each cycle)]→68° C./7 min. PCR products were double-digested with restriction endonucleases according to the protocols described in Table 1.

were subsequently used for *Arabidopsis* plant transformation.

Plant transformation and cultivation: *Arabidopsis thaliana* Columbia ($T_0$ plants) were transformed using the Floral Dip procedure described by Clough S J and Bent A F [The Plant J. 16:735-743 (1998)] and by Desfeux et al. [Plant Physiology 123:895-904 (2000)] with minor modifications. Briefly, $T_0$ Plants were sown in 250 ml pots filled with wet peat-based growth mix. The pots were covered with aluminum foil and a plastic dome, kept at 4° C. for 3-4 days, then uncovered and

TABLE 1

DRE double digestion protocols

| Enzyme combination | First digest | Buffer (Roche) | Digest time (min) | Heat inactivation conditions | Second digest | Buffer | Digest time (min) | Heat inactivation conditions |
|---|---|---|---|---|---|---|---|---|
| HindIII, SalI | HindIII | M | 90 | 20 min, 70° C. | SalI | M + NaCl + Tris | 60 | 20 min, 70° C. |
| HindIII, BamHI | HindIII | B | 30 | No | BamHI | B | 60 | 20 min, 70° C. |
| SalI, BamHI | BamHI | M | 60 | 20 min, 80° C. | SalI | M + NaCl + Tris | 60 | 20 min, 70° C. |
| HindIII, EcoRV | HindIII | B | 30 | No | EcoRV | B | 60 | 20 min, 70° C. |
| SalI, ScaI | SalI, ScaI | H | 60 | 20 min, 80° C. | | | | |
| BamHI, SmaI | SmaI | A | 60 (30° C.) | 20 min, 70° C. | BamHI | A | 60 | 20 min, 80° C. |
| SalI, PvuII | PvuII | M | 60 | 20 min, 80° C. | SalI | M + NaCl + Tris | 60 | 20 min |
| HindIII, PvuII | HindIII | M | 30 | No | PvuII | M | 60 | 20 min, 80° C. |
| HindIII, StuI | HindIII, StuI | B | 90 | 20 min, 80° C. | | | | |
| BamHI, StuI | StuI | B | 30 | No | BamHI | B | 60 | 20 min, 80° C. |

Cloning of DREs in luciferase reporter gene expression: PCR amplified DREs were cloned into a luciferase reporter gene expression vector pVER1, derived from the binary vector pBI101 (Clontech), was double-digested using the same restriction endonucleases used to excise cloned DREs from vector, purified using PCR Purification Kit (Qiagen, Germany), treated with alkaline-phophatase (Roche) according to the manufacturer's instructions and re-purified using PCR Purification Kit (Qiagen, Germany). Insertion of DRE into vector pVER1 was performed by adding to DRE digests: 500 ng of double digested pVer1 plasmid, 1 µl of T4 DNA ligase (40 U/µl; Roche) and 6 µl of T4 buffer (Roche). Following overnight incubation of ligation mixes at 4° C., *Agrobacterium tumefaciens* GV303 competent cells were transformed using 1-2 µl of ligation reaction mixture by electroporation, using a MicroPulser electroporator (Biorad), 0.2 cm cuvettes (Biorad) and EC-2 electroporation program (Biorad). *Agrobacterium* cells were grown on LB at 28° C. for 3 h and plated on LB-agar plates supplemented with the antibiotics gentamycin 50 mg/L (Sigma) and kanamycin 50 mg/L (Sigma). Plates were then incubated at 28° C. for 48 h. Cloned DREs were identified by PCR analysis of bacterial colony DNA using the vector specific, insert flanking upstream and downstream primers 5'-AGGTACTTGGAGCGGCCGCA-3' and 5'-CGAACACCACGGTAGGCTG-3', respectively and the thermal cycle: 92° C./3 min→31×[94° C./30 sec→54° C./30 sec→72° C./X min (X=length (kb) of longest PCR product expected)] 72° C./10 min. Positive *Agrobacterium* colonies incubated in a growth chamber at 18-24° C. under 16/8 hr light/dark cycle. The $T_0$ plants were ready for transformation six days before anthesis.

Single colonies of *Agrobacterium* carrying plant DREs were cultured in LB medium supplemented with kanamycin (50 mg/L) and gentamycin (50 mg/L). The cultures were incubated at 28° C. for 48 hours under vigorous shaking and centrifuged at 4000 rpm for 5 minutes. The pellets comprising *Agrobacterium* cells were resuspended in a transformation medium which contained half-strength (2.15 g/L) Murashig-Skoog (Duchefa); 0.044 µM benzylamino purine (Sigma); 112 µg/L B5 Gambourg vitamins (Sigma); 5% sucrose; and 0.2 ml/L Silwet L-77 (OSI Specialists, CT) in double-distilled water, at pH of 5.7.

Transformation of $T_0$ plants was effected by inverting each plant into an *Agrobacterium* suspension such that the above ground plant tissue was submerged for 3-5 seconds. Each inoculated $T_0$ plant was immediately placed in a plastic tray, then covered with clear plastic dome to maintain humidity and kept in the dark at room temperature for eighteen hours to facilitate infection and transformation. Transformed (transgenic) plants were then uncovered and transferred to a greenhouse for recovery and maturation. The transgenic $T_0$ plants were grown in the greenhouse for 3-5 weeks until siliques were brown and dry then seeds were harvested from plants and kept at room temperature until sowing Generating $T_1$ and $T_2$ transgenic plants harboring DREs: Seeds collected from transgenic $T_0$ plants were surface-sterilized by soaking in 70% ethanol for 1 minute, followed by soaking in 5% sodium hypochloride and 0.05% triton for 5 minutes. The surface-sterilized seeds were thoroughly washed in sterile distilled water then placed on culture plates containing half-strength Murashig-Skoog (Duchefa); 2% sucrose; 0.8% plant agar; 50 mM kanamycin; and 200 mM carbenicylin (Duchefa). The culture plates were incubated at 4° C. for 48 hours then transferred to a growth room at 25° C. for an additional week of incubation. Vital $T_1$ Arabidopsis plants were transferred to a fresh culture plates for another week of incubation. Following incubation the $T_1$ plants were removed from culture plates and planted in growth mix contained in 250 ml pots. The transgenic were allowed to grow in a greenhouse to maturity. Seeds harvested from $T_1$ plants were cultured and grown to maturity as $T_2$ plants under the same conditions as used for culturing and growing the $T_1$ plants.

Evaluating DRE gene-promoting activity in transgenic plants: The ability of DREs to promote gene expression in plants was determined based on the expression of luciferase reporter gene. Accordingly, transgenic Arabidopsis plantlets at a development stage of 2-3 true leaves were subjected to luminescence assays using the procedure described by Messinner R. [Plant. J. 22:265 (2000)]. The imaging of luciferase was performed in a darkroom using ultra-low light detection camera (Princeton Instruments Inc., USA). Using the procedure described by Messinner R. [Plant. J. 22:265 (2000)].

Scoring promoter activity in transgenic plants: DREs promoting gene expression was characterized based luciferase expression in transgenic plants using quantitative values such as to enable consistent evaluations of a large volume of transgenic plants, as follows:

Scoring distribution and intensity of expression: The distribution of reporter genes' expression in transgenic plants was presented in a three variables functions, as follows: (i) plant ID (X axis), (ii) plant organ (Y axis), and (iii) development stage (Z axis). The intensity of expression, relevant to any of these three variables, was measured by a distribution function value (DF), referred hereinbelow as $f_{x,y,z}$ (Promoter). The DF received a value ranging from 0 to 5, representing no expression and the highest expression intensity, respectively.

Scoring specificity of expression: The specificity of reporter genes' expression in transgenic plants was calculated by summing two independent addends:

(a) the zero value/nonzero values ratio, as described in table 2 below and which further referred to as the Binary Function B( ); and (b) the variance of the nonzero values only.

TABLE 2

| No. of non zero values | No. of zero values | | | | |
|---|---|---|---|---|---|
| | 0 | 1 | 2 | 3 | 4 |
| 0 | | 0 | 0 | 0 | 0 |
| 1 | 0 | 0.7 | 1.5 | 2 | |
| 2 | 0 | 0.6 | 1 | | |
| 3 | 0 | 0.5 | | | |
| 4 | 0 | | | | |

The Organ Specificity expression value (SpOr) was calculated according to the following equation:

$$SpOr(\text{promoter})=Var_y(Av_{x,z}(f_{x,y,z}(\text{promoter}))|_{y>0})+B(Av_{x,z}(f_{x,y,z}(\text{promoter})))$$

Whereas Var is the variance, Av is the average and B is the Binary Function.

The development Stage Specificity expression value (SpDs) was calculated according to the following equation:

$$SpDS(\text{promoter})=Var_z(Av_{x,y}(f_{x,y,z}(\text{promoter}))|_{z>0})+B(Av_{x,y}(f_{x,y,z}(\text{promoter})))$$

Whereas Var is the variance, Av is the average and B is the Binary Function.

Scoring position effect: Similarly to the Binary Factor approach described above, position values were also classified as either zero or nonzero values. Accordingly, the reporter genes' expression in a given organ in a given development stage was measured by a Local Position Effect value (LoPoEf). The Position Effect value (PoEf) was the average of all the Local Position Effects, calculate in three steps as follows:

1) $h_{x,y,z}(\text{promoter}) = \begin{cases} 0 & f_{x,y,z}(\text{promoter}) = 0 \\ 1 & f_{x,y,z}(\text{promoter}) = 1, 2, 3, 4, 5 \end{cases}$ 2) $LoPoEf(\text{promoter, organ, development\_stage}) = \min\left(\frac{no\_of\_0s\_in(h_{x,y=Y,z=Z}(\text{promoter}))}{no\_of\_non\_0s\_in(h_{x,y=Y,z=Z}(\text{promoter}))}, \frac{no\_of\_non\_0s\_in(h_{x,y=Y,z=Z}(\text{promoter}))}{no\_of\_0s\_in(h_{x,y=Y,z=Z}(\text{promoter}))}\right)$ 3) $PoEf(\text{promoter})=Av(LoPoEf(\text{promoter},Y,Z))$.

Scoring expression level: The average expression level value (ExLe) and the ExLe variance (VrExLe) were calculated per each DRE promoter×plant organ×plant development stage combination, according the following equations:

$$ExLe(\text{promoter,organ,development\_stage})=Av_x(f_{x,y,z}(\text{promoter}))$$

$$VrExLe(\text{promoter,organ,development\_stage})=var_x(f_{x,y,z}(\text{promoter}))$$

Scoring evaluation reliability: The General Reliability value (Grel) was the number of independent plants that were used for evaluating a specific DRE promoter activity. Hence, $GRel(\text{promoter})=Count_x(f_{x,y,z}(\text{promoter}))$. The Development Stage Reliability value (Rel(DS)) was the number of independent plants that were used for evaluating a specific DRE promoter activity in any given plant developing stage. Rel(promoter, development\_stage)=$Count_{x|z=development\_stage}(f_{x,y,z}(\text{promoter}))$.

Creation of partial fragments from vDREs 4209 and 6669: Genomic DNA derived from Arabidopsis thaliana var Col0 was extracted and PCR-amplified using oligonucleotide primers complementary to sequences within vDRE 4209 (SEQ ID NO:36) [sense primer 5'-GTTGGTTCGTCGAC-TAGAGAAGGT-3' (SEQ ID NO: 208), antisense primer 5'-TTGGATCCGGGAGGCAATGATGCTTTAG-3' (SEQ ID NO: 209)], and vDRE 6669 (SEQ ID NO:61) [sense primer 5'-TTGTAAGCTTGCAGGGATACGGATGGG-TAG-3' (SEQ ID NO: 211), antisense primer 5'-AAATATTG-GATCCTTTGGGGTTCTC-3' (SEQ ID NO: 212)].

The above PCR amplifications resulted in a 470 bp fragment, containing bp 76-548 of the original vDRE 4209 (SEQ ID NO:210) and a 1569 bp fragment, containing bp 748-2316 of the original vDRE 6669 (SEQ ID NO:213), respectively.

PCR products were digested with HindIII and BamHI and ligated into the binary vector, pBI121 (Clontech, accession number: AF485783) upstream to the GUS gene, generating plasmids p4209short-GUS, and p6669short-GUS, respectively. *Arabidopsis* plants (var col0) were transformed with the binary constructs generated (p4209short-GUS and p6669short-GUS), and GUS activity was analyzed on 10 independent T1 transformed plants using standard GUS staining protocol [Jefferson R A, Kavanagh T A, Bevan M W. 1987. GUS fusions: beta-glucuronidase as a sensitive and versatile gene fusion marker in higher plants. EMBO J. 6(13): 3901-7]. Genomic DNA extraction, PCR amplification, DNA restriction, ligation and transformation of *Arabidopsis* plant were preformed according to the protocols described above.

Experimental Results

Various features of the isolated DREs of the present invention are described in Tables 3-17 which follow. As is clearly evident from the Table provided data, the DREs of the present invention exhibit a wide range of gene-promoting activities including: constitutive, inductive, tissue specific, and stage specific activities.

Characterization of DREs:

TABLE 3

| DRE number[1] | 1345 | 1495 | 2176 |
|---|---|---|---|
| Cluster reference[2] | Z18125 | Z17428 | ATBIBBI |
| Cluster position[2] | Upstream | Upstream | Upstream |
| DRE regulatory direction[3] | Bidirectional | Unidirectional | Unidirectional |
| DRE length (bp) | 1611 | 901 | 2192 |
| DRE sequence | SEQ ID NO: 1 | SEQ ID NO: 6 | SEQ ID NO: 11 |
| Internal forward primer sequence[4] | SEQ ID NO: 2 | SEQ ID NO: 7 | SEQ ID NO: 12 |
| External forward primer sequence[4] | SEQ ID NO: 3 | SEQ ID NO: 8 | SEQ ID NO: 13 |
| Internal reverse primer sequence[4] | SEQ ID NO: 4 | SEQ ID NO: 9 | SEQ ID NO: 14 |
| External reverse primer sequence[4] | SEQ ID NO: 5 | SEQ ID NO: 10 | SEQ ID NO: 15 |
| Position Effect Value[5] | 0.37 | 0.21 | 8.33 |
| Development Stage Specificity Value[5] | 1.09 | 0.32 | 0.62 |
| Organ Specificity Value[5] | 1.56 | 0.38 | 2.60 |
| Number of transgenic plants | 11 | 10 | 7 |
| Young roots score (No., Ave., Var)[6] | 10, 12, 3.36 | 6, 2.333, 1.555 | 4, 0, 0 |
| Mature roots score (No., Ave., Var)[6] | 7, 1.571, 3.387 | 7, 3, 2.285 | 5, 0, 0 |
| Young above-ground Tissue (No., Ave., Var)[6] | 10, 3.3, 2.21 | 6, 4.16, 0.13 | 4, 0, 0 |
| Mature above-ground tissue (No., Ave., Var)[6] | 7, 3, 2 | 7, 3.28, 1.06 | 5, 0, 0 |
| Siliques/Seed (No., Ave., Var)[6] | 3, 4.33, 0.88 | 3, 2, 2 | 3, 1.67, 5.56 |
| Flowers (No., Ave., Var)[6] | 7, 1.42, 3.10 | 7, 3.14, 4.40 | 5, 4.2, 2.56 |
| Description | Constitutive. Strong in seeds. | Constitutive. | Specific to flower tissue. Strong in flower buds. Lower expression in open flowers. |

[1]ID number of the DRE as assigned by the present inventors.
[2]Internal reference assigned by the present inventors to a cluster of *Arabidopsis* genes (contig) downstream or upstream of the DRE.
[3]Unidirectional implies that only the sense strand of the DRE is capable of regulating gene expression; Bidirectional implies that both the sense and antisense strands of the DRE are capable of regulating gene expression.
[4]A PCR primer for isolating the DRE from *Arabidopsis* genomic DNA.
[5]Position Effect Values (PoEf), Development Stage-Specificity Values (SpDs) and Organ Specificity Values (SpOr) were calculated as described in the materials and methods section hereinabove.
[6]No. = number; Ave. = average; Var. = variance.

TABLE 4

| DRE number[1] | 2524 | 3560 | 3583 |
|---|---|---|---|
| Cluster reference[2] | Z17778 | Z17937 | av558751 |
| Cluster position[2] | Upstream | Upstream | Upstream |
| DRE regulatory direction | Bidirectional | Bidirectional | Bidirectional |
| DRE length (bp) | 1975 | 3126 | 2501 |
| DRE sequence | SEQ ID NO: 16 | SEQ ID NO: 21 | SEQ ID NO: 26 |
| Internal forward primer sequence[4] | SEQ ID NO: 17 | SEQ ID NO: 22 | SEQ ID NO: 27 |

TABLE 4-continued

| | | | |
|---|---|---|---|
| External forward primer sequence[4] | SEQ ID NO: 18 | SEQ ID NO: 23 | SEQ ID NO: 28 |
| Internal reverse primer sequence[4] | SEQ ID NO: 19 | SEQ ID NO: 24 | SEQ ID NO: 29 |
| External reverse primer sequence[4] | SEQ ID NO: 20 | SEQ ID NO: 25 | SEQ ID NO: 30 |
| Position Effect Value[5] | 0.15 | 0.3 | 5.555 |
| Development Stage Specificity Value[5] | 0.69 | 0.77 | 1.5 |
| Organ Specificity Value[5] | 1.16 | 1.14 | 2 |
| Number of transgenic plants | 8 | 11 | 6 |
| Young roots score (No., Ave., Var)[6] | 5, 0, 0 | 6, 3.5, 1.92 | 5, 0, 0 |
| Mature roots score (No., Ave., Var)[6] | 5, 0, 0 | 7, 3.71, 1.63 | 4, 0, 0 |
| Young above-ground Tissue (No., Ave., Var)[6] | 5, 0.4, 0.24 | 6, 1.83, 2.14 | 5, 0, 0 |
| Mature above-ground tissue (No., Ave., Var)[6] | 5, 2, 0.8 | 7, 1.43, 1.10 | 4, 0.25, 0.19 |
| Siliques/Seed (No., Ave., Var)[6] | 3, 0, 0 | 3, 0.67, 0.89 | 3, 0, 0 |
| Flowers (No., Ave., Var)[6] | 5, 0.4, 0.64 | 7, 1.86, 1.55 | 4, 0, 0 |
| Description | Specific to above ground tissue. | Specific to root tissue. Strong expression, mainly in root meristems. Weak expression in above ground tissues. | Weak in above ground tissue. |

[1]ID number of the DRE as assigned by the present inventors.
[2]Internal reference assigned by the present inventors to a cluster of *Arabidopsis genes* (contig) downstream or upstream of the DRE.
[3]Unidirectional implies that only the sense strand of the DRE is capable of regulating gene expression; Bidirectional implies that both the sense and antisense strands of the DRE are capable of regulating gene expression.
[4]A PCR primer for isolating the DRE from *Arabidopsis* genomic DNA.
[5]Position Effect Values (PoEf), Development Stage-Specificity Values (SpDs) and Organ Specificity Values (SpOr) were calculated as described in the materials and methods section hereinabove.
[6]No. = number; Ave. = average; Var. = variance.

TABLE 5

| | | | |
|---|---|---|---|
| DRE number[1] | 3714 | 4209 | 5095 |
| Cluster reference[2] | Z25961 | Z29176 | AI996150 |
| Cluster position[2] | Upstream | Downstream | Downstream |
| DRE regulatory direction | Unidirectional | Bidirectional | Bidirectional |
| DRE length (bp) | 513 | 1022 | 1056 |
| DRE sequence | SEQ ID NO: 31 | SEQ ID NO: 36 | SEQ ID NO: 41 |
| Internal forward primer sequence[4] | SEQ ID NO: 32 | SEQ ID NO: 37 | SEQ ID NO: 42 |
| External forward primer sequence[4] | SEQ ID NO: 33 | SEQ ID NO: 38 | SEQ ID NO: 43 |
| Internal reverse primer sequence[4] | SEQ ID NO: 34 | SEQ ID NO: 39 | SEQ ID NO: 44 |
| External reverse primer sequence[4] | SEQ ID NO: 35 | SEQ ID NO: 40 | SEQ ID NO: 45 |
| Position Effect Value[5] | 0.3625 | 0.40 | 0.6 |
| Development Stage Specificity Value[5] | 0.11241 | 0.57 | 0 |
| Organ Specificity Value[5] | 0.377 | 0.40 | 0.85 |
| Number of transgenic plants | 11 | 18 | 3 |
| Young roots score (No., Ave., Var)[6] | 9, 0.611, 0.987 | 14, 3.46, 2.87 | 2, 0.5, 0.25 |
| Mature roots score (No., Ave., Var)[6] | 3, 0, 0 | 9, 2.11, 3.65 | 2, 1, 1 |
| Young above-ground Tissue (No., Ave., Var)[6] | 9, 2.38, 1.20 | 14, 2.89, 2.36 | 2, 1.5, 1.25 |
| Mature above-ground tissue (No., Ave., Var)[6] | 3, 1, 2 | 9, 2.44, 1.80 | 2, 2, 0 |
| Siliques/Seed (No., Ave., Var)[6] | 3, 1.66, 0.22 | 3, 1.33, 1.56 | Not available |

TABLE 5-continued

| | | | |
|---|---|---|---|
| Flowers (No., Ave., Var)[6] | 3, 1.33, 3.55 | 9, 2, 3.78 | 2, 0, 0 |
| Description | Weak in above ground tissue | Strong in roots, mainly roo tips, and flower buds. Lower expression in veins. Very low expression in seeds. | Constitutive, weak. |

[1] ID number of the DRE as assigned by the present inventors.
[2] Internal reference assigned by the present inventors to a cluster of *Arabidopsis* genes (contig) downstream or upstream of the DRE.
[3] Unidirectional implies that only the sense strand of the DRE is capable of regulating gene expression; Bidirectional implies that both the sense and antisense strands of the DRE are capable of regulating gene expression.
[4] A PCR primer for isolating the DRE from *Arabidopsis* genomic DNA.
[5] Position Effect Values (PoEf), Development Stage-Specificity Values (SpDs) and Organ Specificity Values (SpOr) were calculated as described in the materials and methods section hereinabove.
[6] No. = number; Ave. = average; Var. = variance.

TABLE 6

| | | | |
|---|---|---|---|
| DRE number[1] | 5311 | 5532 | 5587 |
| Cluster reference[2] | ATHCOL2A | ATASCO | Z26363 |
| Cluster position[2] | Upstream | Upstream | Upstream |
| DRE regulatory direction | Bidirectional | Unidirectional | Unidirectional |
| DRE length (bp) | 435 | 3348 | 1331 |
| DRE sequence | SEQ ID NO: 46 | SEQ ID NO: 51 | SEQ ID NO: 56 |
| Internal forward primer sequence[4] | SEQ ID NO: 47 | SEQ ID NO: 52 | SEQ ID NO: 57 |
| External forward primer sequence[4] | SEQ ID NO: (none) | SEQ ID NO: 53 | SEQ ID NO: 58 |
| Internal reverse primer sequence[4] | SEQ ID NO: 49 | SEQ ID NO: 54 | SEQ ID NO: 59 |
| External reverse primer sequence[4] | SEQ ID NO: (none) | SEQ ID NO: 55 | SEQ ID NO: 60 |
| Position Effect Value[5] | 0.36 | 0.25 | 8.33 |
| Development Stage Specificity Value[5] | 1.15 | 1.30932 | 1.5 |
| Organ Specificity Value[5] | 0.332 | 1.246 | 2 |
| Number of transgenic plants | 8 | 6 | 4 |
| Young roots score (No., Ave., Var)[6] | 7, 0.36, 0.48 | 5, 2.2, 1.36 | 4, 0, 0 |
| Mature roots score (No., Ave., Var)[6] | 4, 0.5, 0.75 | 4, 4.25, 0.187 | 3, 0, 0 |
| Young above-ground Tissue (No., Ave., Var)[6] | 7, 1.57, 1.74 | 5, 3.6, 1.84 | 4, 0, 0 |
| Mature above-ground tissue (No., Ave., Var)[6] | 4, 1.5, 2.25 | 4, 3.5, 0.25 | 3, 0, 0 |
| Siliques/Seed (No., Ave., Var)[6] | Not available | 3, 0.67, 0.22 | 3, 1.33, 3.55 |
| Flowers (No. Ave., Var)[6] | 4, 0.25, 0.18 | 4, 2, 4.5 | 3, 0, 0 |
| Description | Constitutive, weak. | Constitutive, mainly in vegetative tissue. | Siliques specific. High position effect. |

[1] ID number of the DRE as assigned by the present inventors.
[2] Internal reference assigned by the present inventors to a cluster of *Arabidopsis* genes (contig) downstream or upstream of the DRE.
[3] Unidirectional implies that only the sense strand of the DRE is capable of regulating gene expression; Bidirectional implies that both the sense and antisense strands of the DRE are capable of regulating gene expression.
[4] A PCR primer for isolating the DRE from *Arabidopsis* genomic DNA.
[5] Position Effect Values (PoEf), Development Stage-Specificity Values (SpDs) and Organ Specificity Values (SpOr) were calculated as described in the materials and methods section hereinabove.
[6] No. = number; Ave. = average; Var. = variance.

TABLE 7

| | | | |
|---|---|---|---|
| DRE number[1] | 6669 | 6762 | 7357 |
| Cluster reference[2] | Z26440 | Z17588 | F13952 |
| Cluster position[2] | Upstream | Upstream | Upstream |
| DRE regulatory direction | Unidirectional | Bidirectional | Unidirectional |
| DRE length (bp) | 2316 | 379 | 979 |
| DRE sequence | SEQ ID NO: 61 | SEQ ID NO: 66 | SEQ ID NO: 71 |
| Internal forward primer sequence[4] | SEQ ID NO: 62 | SEQ ID NO: 67 | SEQ ID NO: 72 |
| External forward primer sequence[4] | SEQ ID NO: 63 | SEQ ID NO: 68 | SEQ ID NO: 73 |

TABLE 7-continued

| | | | |
|---|---|---|---|
| Internal reverse primer sequence[4] | SEQ ID NO: 64 | SEQ ID NO: 69 | SEQ ID NO: 74 |
| External reverse primer sequence[4] | SEQ ID NO: 65 | SEQ ID NO: 70 | SEQ ID NO: 75 |
| Position Effect Value[5] | 0.28 | 9.72 | 0.32 |
| Development Stage Specificity Value[5] | 1.18 | 0.16 | 0.6 |
| Organ Specificity Value[5] | 1.32 | 1.42 | 0.64 |
| Number of transgenic plants | 4 | 11 | 7 |
| Young roots score (No., Ave., Var)[6] | 3, 2.67, 0.22 | 8, 1.25, 4.69 | 6, 0.5, 0.58 |
| Mature roots score (No., Ave., Var)[6] | 4, 4.75, 0.19 | 9, 0.33, 0.89 | 5, 0, 0 |
| Young above-ground Tissue (No., Ave., Var)[6] | 3, 3.67, 3.56 | 8, 4.19, 0.87 | 6, 0.43, 0.47 |
| Mature above-ground tissue (No., Ave., Var)[6] | 4, 1, 3 | 9, 3.61, 1.10 | 5, 0.8, 0.16 |
| Siliques/Seed (No., Ave., Var)[6] | 4, 0.75, 0.69 | 3, 3.33, 1.56 | 3, 0, 0 |
| Flowers (No., Ave., Var)[6] | 4, 3, 4.5 | 9, 3.11, 2.57 | 5, 1.2, 1.36 |
| Description | Specific to young and meristematic tissue. | Strong in above ground tissue. | Weak in above ground tissue. |

[1]ID number of the DRE as assigned by the present inventors.

[2]Internal reference assigned by the present inventors to a cluster of *Arabidopsis* genes (contig) downstream or upstream of the DRE.

[3]Unidirectional implies that only the sense strand of the DRE is capable of regulating gene expression; Bidirectional implies that both the sense and antisense strands of the DRE are capable of regulating gene expression.

[4]A PCR primer for isolating the DRE from *Arabidopsis* genomic DNA.

[5]Position Effect Values (PoEf), Development Stage-Specificity Values (SpDs) and Organ Specificity Values (SpOr) were calculated as described in the materials and methods section hereinabove.

[6]No. = number; Ave. = average; Var. = variance.

TABLE 8

| | | | |
|---|---|---|---|
| DRE number[1] | 7617 | 8463 | 9136 |
| Cluster reference[2] | Z17636 | Z26728 | F15462 |
| Cluster position[2] | Upstream | Downstream | Downstream |
| DRE regulatory direction | Bidirectional | Unidirectional | Unidirectional |
| DRE length (bp) | 665 | 2834 | 486 |
| DRE sequence | SEQ ID NO: 76 | SEQ ID NO: 81 | SEQ ID NO: 86 |
| Internal forward primer sequence[4] | SEQ ID NO: 77 | SEQ ID NO: 82 | SEQ ID NO: 87 |
| External forward primer sequence[4] | SEQ ID NO: 78 | SEQ ID NO: 83 | SEQ ID NO: 88 |
| Internal reverse primer sequence[4] | SEQ ID NO: 79 | SEQ ID NO: 84 | SEQ ID NO: 89 |
| External reverse primer sequence[4] | SEQ ID NO: 80 | SEQ ID NO: 85 | SEQ ID NO: 90 |
| Position Effect Value[5] | 0.42 | 0.16 | 0.48 |
| Development Stage Specificity Value[5] | 0.16 | 0.68 | 0.60 |
| Organ Specificity Value[5] | 0.41 | 2.02 | 0.53 |
| Number of transgenic plants | 3 | 12 | 13 |
| Young roots score (No., Ave., Var)[6] | 3, 0, 0 | 6, 0, 0 | 9, 0.778, 2.617 |
| Mature roots score (No., Ave., Var)[6] | 3, 0, 0 | 7, 1.14, 3.55 | 11, 0.73, 1.107 |
| Young above-ground Tissue (No., Ave., Var)[6] | 3, 0.17, 5.56 | 6, 3.33, 3.32 | 9, 0.778, 0.84 |
| Mature above-ground tissue (No., Ave., Var)[6] | 3, 0.33, 0.22 | 7, 2, 2.57 | 11, 1.18, 2.51 |
| Siliques/Seed (No., Ave., Var)[6] | 2, 1, 1 | 4, 0, 0 | 3, 0, 0 |

TABLE 8-continued

| | | | |
|---|---|---|---|
| Flowers (No., Ave., Var)[6] | 3, 0.33, 0.22 | 7, 3.57, 3.96 | 11, 0.55, 0.98 |
| Description | Very weak in above ground tissue. | Strong in above ground tissue of seedlings. Strong in flower tissue of mature plants. | Constitutive, weak. |

[1]ID number of the DRE as assigned by the present inventors.
[2]Internal reference assigned by the present inventors to a cluster of *Arabidopsis* genes (contig) downstream or upstream of the DRE.
[3]Unidirectional implies that only the sense strand of the DRE is capable of regulating gene expression; Bidirectional implies that both the sense and antisense strands of the DRE are capable of regulating gene expression.
[4]A PCR primer for isolating the DRE from *Arabidopsis* genomic DNA.
[5]Position Effect Values (PoEf), Development Stage-Specificity Values (SpDs) and Organ Specificity Values (SpOr) were calculated as described in the materials and methods section hereinabove.
[6]No. = number; Ave. = average; Var. = variance.

TABLE 9

| | | | |
|---|---|---|---|
| DRE number[1] | 10826 | 12582 | 13257 |
| Cluster reference[2] | Z30896 | Z33953 | Z17541 |
| Cluster position[2] | Upstream | Downstream | Upstream |
| DRE regulatory direction | Bidirectional | Unidirectional | Bidirectional |
| DRE length (bp) | 1840 | 1665 | 807 |
| DRE sequence | SEQ ID NO: 91 | SEQ ID NO: 96 | SEQ ID NO: 101 |
| Internal forward primer sequence[4] | SEQ ID NO: 92 | SEQ ID NO: 97 | SEQ ID NO: 102 |
| External forward primer sequence[4] | SEQ ID NO: 93 | SEQ ID NO: 98 | SEQ ID NO: 103 |
| Internal reverse primer sequence[4] | SEQ ID NO: 94 | SEQ ID NO: 99 | SEQ ID NO: 104 |
| External reverse primer sequence[4] | SEQ ID NO: 95 | SEQ ID NO: 100 | SEQ ID NO: 105 |
| Position Effect Value[5] | 0.27 | 0.19 | 0 |
| Development Stage Specificity Value[5] | 0.50 | 0.32 | 1.5 |
| Organ Specificity Value[5] | 8.19 | 1.38 | 1.14 |
| Number of transgenic plants | 5 | 20 | 2 |
| Young roots score (No., Ave., Var)[6] | 3, 1.67, 2.89 | 18, 0.56, 1.36 | 2, 0, 0 |
| Mature roots score (No., Ave., Var)[6] | 4, 3.38, 4.17 | 10, 0.5, 1.05 | 2, 0, 0 |
| Young above-ground Tissue (No., Ave., Var)[6] | 3, 2, 2.67 | 18, 2.39, 3.90 | 2, 0, 0 |
| Mature above-ground tissue (No., Ave., Var)[6] | 4, 3.12, 1.55 | 10, 3.2, 0.36 | 2, 2.5, 0.25 |
| Siliques/Seed (No., Ave., Var)[6] | Not available | 3, 1, 0 | 2, 0, 0 |
| Flowers (No., Ave., Var)[6] | 4, 3.25, 3.06 | 10, 4.4, 1.84 | 2, 2, 1 |
| Description | Strong in root and flower tissue. | Strong in above ground tissue of seedlings. Lower expression in mature plants. | Specific to above ground tissue of mature plants. |

[1]ID number of the DRE as assigned by the present inventors.
[2]Internal reference assigned by the present inventors to a cluster of *Arabidopsis* genes (contig) downstream or upstream of the DRE.
[3]Unidirectional implies that only the sense strand of the DRE is capable of regulating gene expression; Bidirectional implies that both the sense and antisense strands of the DRE are capable of regulating gene expression.
[4]A PCR primer for isolating the DRE from *Arabidopsis* genomic DNA.
[5]Position Effect Values (PoEf), Development Stage-Specificity Values (SpDs) and Organ Specificity Values (SpOr) were calculated as described in the materials and methods section hereinabove.
[6]No. = number; Ave. = average; Var. = variance.

TABLE 10

| | | | |
|---|---|---|---|
| DRE number[1] | 13277 | 15980 | 16665 |
| Cluster reference[2] | Z18392 | BE522497 | T04806 |
| Cluster position[2] | Upstream | Downstream | Downstream |
| DRE regulatory direction | Bidirectional | Unidirectional | Bidirectional |
| DRE length (bp) | 3297 | 2183 | 1358 |
| DRE sequence | SEQ ID NO: 106 | SEQ ID NO: 111 | SEQ ID NO: 116 |
| Internal forward primer sequence[4] | SEQ ID NO: 107 | SEQ ID NO: 112 | SEQ ID NO: 117 |
| External forward primer sequence[4] | SEQ ID NO: 108 | SEQ ID NO: 113 | SEQ ID NO: 118 |

TABLE 10-continued

| | | | |
|---|---|---|---|
| Internal reverse primer sequence[4] | SEQ ID NO: 109 | SEQ ID NO: 114 | SEQ ID NO: 119 |
| External reverse primer sequence[4] | SEQ ID NO: 110 | SEQ ID NO: 115 | SEQ ID NO: 120 |
| Position Effect Value[5] | 0.22 | 0.38 | 0.33 |
| Development Stage Specificity Value[5] | 1.5 | 1.18 | 4.44 |
| Organ Specificity Value[5] | 1 | 1.45 | 1.5 |
| Number of transgenic plants | 5 | 16 | 5 |
| Young roots score (No., Ave., Var)[6] | 5, 0.6, 0.24 | 10, 2.1, 1.49 | 5, 0, 0 |
| Mature roots score (No., Ave., Var)[6] | 3, 0, 0 | 13, 2.46, 0.86 | 2, 0, 0 |
| Young above-ground Tissue (No., Ave., Var)[6] | 5, 0.4, 0.24 | 10, 12, 1.76 | 5, 0.6, 0.34 |
| Mature above-ground tissue (No., Ave., Var)[6] | 3, 0, 0 | 13, 0.46, 0.86 | 2, 0.5, 0.25 |
| Siliques/Seed (No., Ave., Var)[6] | 3, 0, 0 | 4, 3.75, 1.69 | Not available |
| Flowers (No., Ave., Var)[6] | 3, 0, 0 | 13, 0.92, 1.76 | 2, 0, 0 |
| Description | Weak in seedlings. | Root tissue, mainly root tips; and seeds. | Above ground vegetative tissue of mature plants. |

[1]ID number of the DRE as assigned by the present inventors.
[2]Internal reference assigned by the present inventors to a cluster of *Arabidopsis* genes (contig) downstream or upstream of the DRE.
[3]Unidirectional implies that only the sense strand of the DRE is capable of regulating gene expression; Bidirectional implies that both the sense and antisense strands of the DRE are capable of regulating gene expression.
[4]A PCR primer for isolating the DRE from *Arabidopsis* genomic DNA.
[5]Position Effect Values (PoEf), Development Stage-Specificity Values (SpDs) and Organ Specificity Values (SpOr) were calculated as described in the materials and methods section hereinabove.
[6]No. = number; Ave. = average; Var. = variance.

TABLE 11

| | | | |
|---|---|---|---|
| DRE number[1] | 16900 | 17109 | 17809 |
| Cluster reference[2] | Z25996 | Z17897 | Z18103 |
| Cluster position[2] | Upstream | Upstream | Upstream |
| DRE regulatory direction | Bidirectional | Bidirectional | Bidirectional |
| DRE length (bp) | 824 | 2927 | 3165 |
| DRE sequence | SEQ ID NO: 121 | SEQ ID NO: 126 | SEQ ID NO: 131 |
| Internal forward primer sequence[4] | SEQ ID NO: 122 | SEQ ID NO: 127 | SEQ ID NO: 132 |
| External forward primer sequence[4] | SEQ ID NO: 123 | SEQ ID NO: 128 | SEQ ID NO: 133 |
| Internal reverse primer sequence[4] | SEQ ID NO: 124 | SEQ ID NO: 129 | SEQ ID NO: 134 |
| External reverse primer sequence[4] | SEQ ID NO: 125 | SEQ ID NO: 130 | SEQ ID NO: 135 |
| Position Effect Value[5] | 4.17 | 0.26 | 0.21 |
| Development Stage Specificity Value[5] | 0.21 | 0.63 | 0.60 |
| Organ Specificity Value[5] | 0.22 | 1.85 | 1.38 |
| Number of transgenic plants | 5 | 10 | 10 |
| Young roots score (No., Ave., Var)[6] | 4, 3.5, 0.75 | 6, 4, 1.25 | 5, 0.8, 0.56 |
| Mature roots score (No., Ave., Var)[6] | 5, 3.2, 0.56 | 7, 3.07, 2.60 | 7, 1.5, 1.5 |
| Young above-ground Tissue (No., Ave., Var)[6] | 4, 4, 0 | 6, 0.42, 0.37 | 5, 4, 0.8 |
| Mature above-ground tissue (No., Ave., Var)[6] | 5, 3.8, 0.56 | 7, 1.05, 1.07 | 7, 3.07, 1.03 |
| Siliques/Seed (No., Ave., Var)[6] | 3, 4.67, 0.22 | 3, 0, 0 | 3, 0, 0 |
| Flowers (No., Ave., Var)[6] | 5, 4, 4 | 7, 1.07, 2.89 | 7, 2.71, 2.99 |

TABLE 11-continued

| Description | Constitutive pattern. Strong in meristematic tissue and seeds. | Strong in root, flower and meristematic tissue. | Strong in leaf tissue of seedlings. Variable in mature plants. |
|---|---|---|---|

[1] ID number of the DRE as assigned by the present inventors.
[2] Internal reference assigned by the present inventors to a cluster of *Arabidopsis* genes (contig) downstream or upstream of the DRE.
[3] Unidirectional implies that only the sense strand of the DRE is capable of regulating gene expression; Bidirectional implies that both the sense and antisense strands of the DRE are capable of regulating gene expression.
[4] A PCR primer for isolating the DRE from *Arabidopsis* genomic DNA.
[5] Position Effect Values (PoEf), Development Stage-Specificity Values (SpDs) and Organ Specificity Values (SpOr) were calculated as described in the materials and methods section hereinabove.
[6] No. = number; Ave. = average; Var. = variance.

TABLE 12

| DRE number[1] | 19672 | 19678 | 19827 |
|---|---|---|---|
| Cluster reference[2] | Z25683 | BE523552 | Z17577 |
| Cluster position[2] | Upstream | Upstream | Upstream |
| DRE regulatory direction | Unidirectional | Bidirectional | Bidirectional |
| DRE length (bp) | 1155 | 2877 | 578 |
| DRE sequence | SEQ ID NO: 136 | SEQ ID NO: 141 | SEQ ID NO: 146 |
| Internal forward primer sequence[4] | SEQ ID NO: 137 | SEQ ID NO: 142 | SEQ ID NO: 147 |
| External forward primer sequence[4] | SEQ ID NO: 138 | SEQ ID NO: 143 | SEQ ID NO: 148 |
| Internal reverse primer sequence[4] | SEQ ID NO: 139 | SEQ ID NO: 144 | SEQ ID NO: 149 |
| External reverse primer sequence[4] | SEQ ID NO: 140 | SEQ ID NO: 145 | SEQ ID NO: 150 |
| Position Effect Value[5] | 0.03 | 5.55 | 0.37 |
| Development Stage Specificity Value[5] | 9.78 | 1.5 | 0.60 |
| Organ Specificity Value[5] | 3.99 | 2 | 0.64 |
| Number of transgenic plants | 17 | 5 | 12 |
| Young roots score (No., Ave., Var)[6] | 15, 4.33, 0.76 | 5, 0, 0 | 10, 0, 0 |
| Mature roots score (No., Ave., Var)[6] | 17, 4, 1.76 | 4, 0, 0 | 5, 0.1, 0.04 |
| Young above-ground Tissue (No., Ave., Var)[6] | 15, 4.53, 0.38 | 5, 0, 0 | 10, 2.9, 2.29 |
| Mature above-ground tissue (No., Ave., Var)[6] | 17, 3.12, 2.22 | 4, 0.25, 0.18 | 5, 0.8, 1.36 |
| Siliques/Seed (No., Ave., Var)[6] | 3, 4.33, 0.22 | 3, 0, 0 | 3, 0, 0 |
| Flowers (No., Ave., Var)[6] | 17, 4.06, 2.17 | 4, 0, 0 | 5, 0.8, 1.36 |
| Description | Strong, constitutive. Lower expression in mature leaf tissue. | Very weak. High position effect. | Above ground tissue. Weak. |

[1] ID number of the DRE as assigned by the present inventors.
[2] Internal reference assigned by the present inventors to a cluster of *Arabidopsis* genes (contig) downstream or upstream of the DRE.
[3] Unidirectional implies that only the sense strand of the DRE is capable of regulating gene expression; Bidirectional implies that both the sense and antisense strands of the DRE are capable of regulating gene expression.
[4] A PCR primer for isolating the DRE from *Arabidopsis* genomic DNA.
[5] Position Effect Values (PoEf), Development Stage-Specificity Values (SpDs) and Organ Specificity Values (SpOr) were calculated as described in the materials and methods section hereinabove.
[6] No. = number; Ave. = average; Var. = variance.

TABLE 13

| DRE number[1] | 20607 | 22397 | 22604 |
|---|---|---|---|
| Cluster reference[2] | AI998130 | ATHD12A | ATHFEDAA |
| Cluster position[2] | Upstream | Upstream | Downstream |
| DRE regulatory direction | Bidirectional | Unidirectional | Bidirectional |
| DRE length (bp) | 2819 | 1313 | 2080 |
| DRE sequence | SEQ ID NO: 151 | SEQ ID NO: 156 | SEQ ID NO: 161 |
| Internal forward primer sequence[4] | SEQ ID NO: 152 | SEQ ID NO: 157 | SEQ ID NO: 162 |
| External forward primer sequence[4] | SEQ ID NO: 153 | SEQ ID NO: 158 | SEQ ID NO: 163 |
| Internal reverse primer sequence[4] | SEQ ID NO: 154 | SEQ ID NO: 159 | SEQ ID NO: 164 |

TABLE 13-continued

| | | | |
|---|---|---|---|
| External reverse primer sequence[4] | SEQ ID NO: 155 | SEQ ID NO: 160 | SEQ ID NO: 165 |
| Position Effect Value[5] | 0.25 | 0.38 | 9.72 |
| Development Stage Specificity Value[5] | 2.50 | 0.89 | 0.71 |
| Organ Specificity Value[5] | 0.916 | 1.33 | 1.10 |
| Number of transgenic plants | 5 | 12 | 17 |
| Young roots score (No., Ave., Var)[6] | 5, 0, 0 | 12, 1.13, 2.09 | 15, 0, 0 |
| Mature roots score (No., Ave., Var)[6] | 3, 0, 0 | 12, 1.67, 4.22 | 13, 0, 0 |
| Young above-ground Tissue (No., Ave., Var)[6] | 5, 2.2, 2.16 | 12, 3.33, 0.89 | 15, 0.2, 0.16 |
| Mature above-ground tissue (No., Ave., Var)[6] | 3, 2, 2 | 12, 2.63, 2.69 | 13, 0, 0 |
| Siliques/Seed (No., Ave., Var)[6] | Not available | 3, 4, 0.67 | 4, 0.75, 1.69 |
| Flowers (No., Ave., Var)[6] | 3, 1, 2 | 12, 1.21, 3.06 | 13, 0, 0 |
| Description | Above ground tissue. | Above ground tissue and seed. | Above ground tissue and seed. High position effect. Very weak. |

[1]ID number of the DRE as assigned by the present inventors.
[2]Internal reference assigned by the present inventors to a cluster of *Arabidopsis* genes (contig) downstream or upstream of the DRE.
[3]Unidirectional implies that only the sense strand of the DRE is capable of regulating gene expression; Bidirectional implies that both the sense and antisense strands of the DRE are capable of regulating gene expression.
[4]A PCR primer for isolating the DRE from *Arabidopsis* genomic DNA.
[5]Position Effect Values (PoEf), Development Stage-Specificity Values (SpDs) and Organ Specificity Values (SpOr) were calculated as described in the materials and methods section hereinabove.
[6]No. = number; Ave. = average; Var. = variance.

TABLE 14

| | | | |
|---|---|---|---|
| DRE number[1] | 24136 | 24291 | 24728 |
| Cluster reference[2] | Z34788 | Z17960 | AV530349 |
| Cluster position[2] | Downstream | Upstream | Upstream |
| DRE regulatory direction | Unidirectional | Bidirectional | Unidirectional |
| DRE length (bp) | 174 | 2096 | 1617 |
| DRE sequence | SEQ ID NO: 166 | SEQ ID NO: 171 | SEQ ID NO: 176 |
| Internal forward primer sequence[4] | SEQ ID NO: 167 | SEQ ID NO: 172 | SEQ ID NO: 177 |
| External forward primer sequence[4] | SEQ ID NO: none | SEQ ID NO: 173 | SEQ ID NO: 178 |
| Internal reverse primer sequence[4] | SEQ ID NO: 169 | SEQ ID NO: 174 | SEQ ID NO: 179 |
| External reverse primer sequence[4] | SEQ ID NO: none | SEQ ID NO: 175 | SEQ ID NO: 180 |
| Position Effect Value[5] | 0.17 | 0.56 | 5.71 |
| Development Stage Specificity Value[5] | 1.5 | 7.76 | 0.17 |
| Organ Specificity Value[5] | 2 | 6.93 | 1.75 |
| Number of transgenic plants | 5 | 12 | 9 |
| Young roots score (No., Ave., Var)[6] | 1, 0, 0 | 9, 1.56, 3.14 | 8, 0, 0 |
| Mature roots score (No., Ave., Var)[6] | 2, 0, 0 | 8, 2.37, 1.48 | 8, 0.5, 1.75 |
| Young above-ground Tissue (No., Ave., Var)[6] | 1, 0, 0 | 9, 2.33, 3.11 | 8, 2.63, 0.48 |
| Mature above-ground tissue (No., Ave., Var)[6] | 2, 0.25, 0.06 | 8, 1.62, 2.33 | 8, 2.5, 1.5 |
| Siliques/Seed (No., Ave., Var)[6] | 3, 0, 0 | 4, 2, 1.5 | Not available |
| Flowers (No., Ave., Var)[6] | 2, 0, 0 | 8, 1.37, 1.98 | 8, 3.38, 2.73 |

TABLE 14-continued

| Description | Above ground tissue. Very weak. | Constitutive. | Strong in flower tissue. Low expression in veins. |
|---|---|---|---|

[1] ID number of the DRE as assigned by the present inventors.
[2] Internal reference assigned by the present inventors to a cluster of *Arabidopsis* genes (contig) downstream or upstream of the DRE.
[3] Unidirectional implies that only the sense strand of the DRE is capable of regulating gene expression; Bidirectional implies that both the sense and antisense strands of the DRE are capable of regulating gene expression.
[4] A PCR primer for isolating the DRE from *Arabidopsis* genomic DNA.
[5] Position Effect Values (PoEf), Development Stage-Specificity Values (SpDs) and Organ Specificity Values (SpOr) were calculated as described in the materials and methods section hereinabove.
[6] No. = number; Ave. = average; Var. = variance.

TABLE 15

| DRE number[1] | 24811 | 4209 | 5095 |
|---|---|---|---|
| Cluster reference[2] | H36200 | H36237 | Z29720 |
| Cluster position[2] | Upstream | Upstream | Upstream |
| DRE regulatory direction | Bidirectional | Bidirectional | Bidirectional |
| DRE length (bp) | 428 | 1022 | 1056 |
| DRE sequence | SEQ ID NO: 181 | SEQ ID NO: 186 | SEQ ID NO: 191 |
| Internal forward primer sequence[4] | SEQ ID NO: 182 | SEQ ID NO: 187 | SEQ ID NO: 192 |
| External forward primer sequence[4] | SEQ ID NO: none | SEQ ID NO: 188 | SEQ ID NO: 193 |
| Internal reverse primer sequence[4] | SEQ ID NO: 184 | SEQ ID NO: 189 | SEQ ID NO: 194 |
| External reverse primer sequence[4] | SEQ ID NO: none | SEQ ID NO: 190 | SEQ ID NO: 195 |
| Position Effect Value[5] | 0.53 | 0.60 | 0.33 |
| Development Stage Specificity Value[5] | 8.11 | 0.28 | 0.61 |
| Organ Specificity Value[5] | 0.23 | 0.49 | 1.35 |
| Number of transgenic plants | 4 | 5 | 3 |
| Young roots score (No., Ave., Var)[6] | 4, 0.75, 1.69 | 5, 0.4, 0.34 | 3, 0.33, 0.22 |
| Mature roots score (No., Ave., Var)[6] | 3, 1, 2 | 4, 1.2, 2.16 | 2, 1, 1 |
| Young above-ground Tissue (No., Ave., Var)[6] | 4, 1, 3 | 5, 2.4, 1.84 | 3, 1.33, 1.56 |
| Mature above-ground tissue (No., Ave., Var)[6] | 3, 1.33, 3.56 | 5, 2, 2.8 | 2, 2, 0 |
| Siliques/Seed (No., Ave., Var)[6] | Not available | 5, 0.4, 0.24 | 2, 0, 0 |
| Flowers (No., Ave., Var)[6] | 3, 2, 4 | 5, 1.6, 3.44 | 2, 0, 0 |
| Description | Constitutive, weak. | Leaf-stalk and stem tissue. | Vegetative tissue, weak. |

[1] ID number of the DRE as assigned by the present inventors.
[2] Internal reference assigned by the present inventors to a cluster of *Arabidopsis* genes (contig) downstream or upstream of the DRE.
[3] Unidirectional implies that only the sense strand of the DRE is capable of regulating gene expression; Bidirectional implies that both the sense and antisense strands of the DRE are capable of regulating gene expression.
[4] A PCR primer for isolating the DRE from *Arabidopsis* genomic DNA.
[5] Position Effect Values (PoEf), Development Stage-Specificity Values (SpDs) and Organ Specificity Values (SpOr) were calculated as described in the materials and methods section hereinabove.
[6] No. = number; Ave. = average; Var. = variance.

TABLE 16

| DRE number[1] | 17109 | 20607 | 24811 |
|---|---|---|---|
| Cluster reference[2] | R29912 | R90407 | T22055 |
| Cluster position[2] | Downstream | Downstream | Downstream |
| DRE regulatory direction | Bidirectional | Bidirectional | Bidirectional |
| DRE length (bp) | 2027 | 2834 | 428 |
| DRE sequence | SEQ ID NO: 196 | SEQ ID NO: 201 | SEQ ID NO: 202 |
| Internal forward primer sequence[4] | SEQ ID NO: 197 | SEQ ID NO: 168 | SEQ ID NO: 48 |
| External forward primer sequence[4] | SEQ ID NO: 198 | SEQ ID NO: 170 | SEQ ID NO: none |
| Internal reverse primer sequence[4] | SEQ ID NO: 199 | SEQ ID NO: 183 | SEQ ID NO: 50 |
| External reverse primer sequence[4] | SEQ ID NO: 200 | SEQ ID NO: 185 | SEQ ID NO: none |
| Position Effect Value[5] | 0.46 | 0.26 | 0.24 |

TABLE 16-continued

| | | | |
|---|---|---|---|
| Development Stage Specificity Value[5] | 0 | 0.60 | 0.61 |
| Organ Specificity Value[5] | 0.49 | 1.16 | 0.51 |
| Number of transgenic plants | 5 | 5 | 5 |
| Young roots score (No., Ave., Var)[6] | 5, 0.6, 0.64 | 5, 0, 0 | 4, 0.75, 1.69 |
| Mature roots score (No., Ave., Var)[6] | Not available | 5, 0, 0 | 5, 0.6, 1.44 |
| Young above-ground Tissue (No., Ave., Var)[6] | 5, 2, 2 | 5, 2.2, 2.16 | 4, 1, 3 |
| Mature above-ground tissue (No., Ave., Var)[6] | Not available | 5, 1.8, 2.16 | 5, 0.8, 2.56 |
| Siliques/Seed (No., Ave., Var)[6] | Not available | 4, 0, 0 | 3, 0, 0 |
| Flowers (No., Ave., Var)[6] | Not available | 5, 1.2, 1.36 | 5, 0.8, 2.56 |
| Description | Above ground tissue, weak | Above ground tissue, mainly in leaves. | Constitutive, weak |

[1]ID number of the DRE as assigned by the present inventors.
[2]Internal reference assigned by the present inventors to a cluster of *Arabidopsis* genes (contig) downstream or upstream of the DRE.
[3]Unidirectional implies that only the sense strand of the DRE is capable of regulating gene expression; Bidirectional implies that both the sense and antisense strands of the DRE are capable of regulating gene expression.
[4]A PCR primer for isolating the DRE from *Arabidopsis* genomic DNA.
[5]Position Effect Values (PoEf), Development Stage-Specificity Values (SpDs) and Organ Specificity Values (SpOr) were calculated as described in the materials and methods section hereinabove.
[6]No. = number; Ave. = average; Var. = variance.

TABLE 17

| | |
|---|---|
| DRE number[1] | 16665 |
| Cluster reference[2] | Z26101 |
| Cluster position[2] | Upstream |
| DRE regulatory direction | Bidirectional |
| DRE length (bp) | 1358 |
| DRE sequence | SEQ ID NO: 203 |
| Internal forward primer sequence[4] | SEQ ID NO: 204 |
| External forward primer sequence[4] | SEQ ID NO: 206 |
| Internal reverse primer sequence[4] | SEQ ID NO: 206 |
| External reverse primer sequence[4] | SEQ ID NO: 207 |
| Position Effect Value[5] | 0.51 |
| Development Stage Specificity Value[5] | 8.82 |
| Organ Specificity Value[5] | 0.403 |
| Number of transgenic plants | 12 |
| Young roots score (No., Ave., Var)[6] | 10, 0, 0 |
| Mature roots score (No., Ave., Var)[6] | 5, 0.6, 0.64 |
| Young above-ground Tissue (No., Ave., Var)[6] | 10, 1.5, 3.05 |
| Mature above-ground tissue (No., Ave., Var)[6] | 5, 2, 2.08 |
| Siliques/Seed (No., Ave., Var)[6] | 3, 1, 0.66 |
| Flowers (No., Ave., Var)[6] | 5, 1.8, 3.76 |
| Description | Above ground tissue |

[1]ID number of the DRE as assigned by the present inventors.
[2]Internal reference assigned by the present inventors to a cluster of *Arabidopsis* genes (contig) downstream or upstream of the DRE.
[3]Unidirectional implies that only the sense strand of the DRE is capable of regulating gene expression; Bidirectional implies that both the sense and antisense strands of the DRE are capable of regulating gene expression.
[4]A PCR primer for isolating the DRE from *Arabidopsis* genomic DNA.
[5]Position Effect Values (PoEf), Development Stage-Specificity Values (SpDs) and Organ Specificity Values (SpOr) were calculated as described in the materials and methods section hereinabove.
[6]No. = number; Ave. = average; Var. = variance.

Deletion analysis of DREs 4209 and 6669:

The ability of partial DRE sequences to modify in vivo gene expression pattern, was tested by comparing reporter gene expression driven by unmodified DREs (SEQ ID NO:36 and 61) with that of deletion mutants thereof (SEQ ID NO:210 and 213, respectively).

Figure 26A:
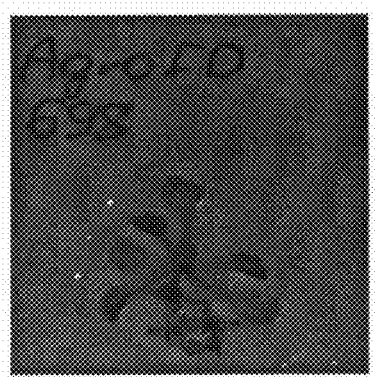
FIGS. 26*a-b* are photographs showing transformed *Arabidopsis thaliana* plants transformed with nucleic acid constructs including partial DREs operably each linked to a GUS encoding sequence.

GUS expression pattern in p4209short-GUS (including the DRE 4209 partial sequence set forth in SEQ ID NO:210) transformed plants was similar to that driven by the full length promoter sequence, DRE 4209 (SEQ ID NO:36). As is shown in FIG. 26a, expression was strong in roots, mainly root tips, as well as in flower buds. Insterstingly, p4209short-GUS transformed plants exhibited lower reporter gene expression in veins, while leaves exhibited higher expression. Note, expression in seeds was not examined.

Figure 26B:
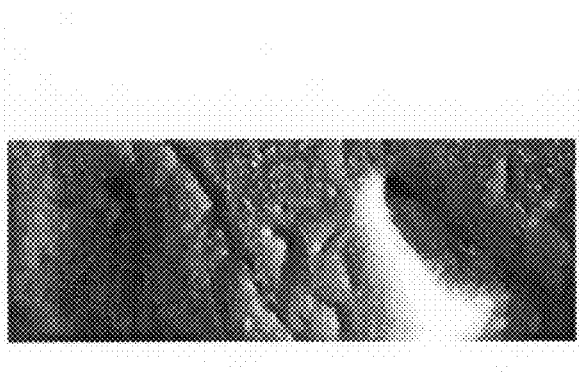

GUS expression pattern in the p6669short-GUS (comprising the DRE 6669 partial sequence set forth in SEQ ID NO:213) transformed plants was restricted to the root tips (FIG. 26b) while expression in other young or meristematic tissues, as was obtained by the full length DRE 6669 promoter (SEQ ID NO:61), was lost.

These results demonstrate that the 5' nucleic acid sequence of SEQ ID NO: 61 (e.g., nucleotide coordinates 1-747), is important for constitutive gene expression. Indeed, a DNA sequence (SEQ ID NO: 214, see FIG. 27 WO 02/16655) which does not include the 5' first 400 nucleotides of SEQ ID NO: 61 has been implicated in stress regulated gene expression.

These results indicate that the promoters of the present invention may be modified by partial deletions, to generate inductive or tissue specific expression pattern as demonstrated for DRE 6669 (SEQ ID NO:61).

As is clearly illustrated by Tables 3-17 and FIGS. 1-26, the DREs isolated according to the teachings of the present invention exhibit a wide range of activities as well as a wide range of tissue and developmental stage specificities. The DREs of the present invention were classified according to function as determined using the *Arabidopsis* assay described hereinabove.

The luciferase gene was expressed in a constitutive manner in *Arabidopsis* when functionally linked to SEQ ID NOS: 1, 6, 41, 46, 51, 61, 86, 121, 136, 171, 181 and 202 (illustrated in FIG. 18), thus the promoters of these DREs are putatively classified herein as constitutive promoters.

The luciferase gene was expressed in an inductive manner in *Arabidopsis* when functionally linked to SEQ ID NOS: 1, 11, 16, 21, 26, 31, 36, 56, 66, 71, 76, 81, 91, 96, 101, 116, 126, 141, 146, 151, 156, 161, 166, 176 and 203, thus the promoters of these DREs are putatively classified herein as inductive promoters.

The luciferase gene was expressed in a young or meristematic, tissue-specific manner in *Arabidopsis* when functionally linked to SEQ ID NOS: 61, 121, 126, 213 (illustrated in FIGS. 4, 14, 15, 16 and 26*b*), thus the promoters of these DREs are putatively classified herein as young or meristematic, tissue-specific promoters.

The luciferase gene was expressed in root tissue specific manner in *Arabidopsis* when functionally linked to SEQ ID NOS: 21, 36, 91, 111, and 126 (illustrated in FIGS. 2, 3, 9, and 13), thus the promoters of these DREs are putatively classified herein as root tissue-specific promoters The luciferase gene was expressed in an above ground tissue-specific manner in *Arabidopsis* when functionally linked to SEQ ID NOS: 16, 26, 31, 66, 71, 76, 81, 96, 106, 101, 116, 131, 146, 151, 156, 161, 166, 196, 201 and 203 (illustrate in FIGS. 10, 11, 17, 19 and 20), thus the promoters of these DREs are putatively classified herein as above ground tissue-specific promoters.

The luciferase gene was expressed in a stem tissue specific manner in *Arabidopsis* when functionally linked to SEQ ID NO: 186 (illustrated in FIG. 22), thus the promoter(s) of this DRE are putatively classified herein as stem tissue specific promoter(s).

The luciferase gene was expressed in a flower tissue specific manner in *Arabidopsis* when functionally linked to SEQ ID NOS: 11, 36, 81, 91, 126, 176 and 210 (illustrated in FIGS. 1, 3, 9 and 26*a*), thus the promoters of these DREs are putatively classified herein as flower tissue-specific promoters.

The luciferase gene was expressed in a fruit (silique) tissue specific manner in *Arabidopsis* when functionally linked to SEQ ID NO: 56, thus the promoter(s) of this DRE are putatively classified herein as fruit (silique) tissue specific promoter(s).

The luciferase gene was expressed in a seed tissue specific manner in *Arabidopsis* when functionally linked to SEQ ID NOS: 1, 156, and 161 (illustrated in FIGS. 12 and 21), thus the promoters of these DREs are putatively classified herein as seed tissue specific promoters.

The luciferase gene was expressed in a developmental stage specific manner in *Arabidopsis* when functionally linked to SEQ ID NOS: 81, 96, 101, 106, and 131 (illustrated comparatively in FIGS. 5-6, 7-8, 10-11 and 15-16), thus the promoters of these DREs are putatively classified herein as developmental stage specific promoters.

The GUS gene was expressed in an inductive manner in *Arabidopsis* when functionally linked to SEQ ID NOS: 210 and 213 (illustrated in FIG. 26*b*), thus the promoters of these partial DREs sequences are putatively classified herein as inductive promoters.

The GUS gene was expressed in a root, as well as in a flower bud tissue specific manner in *Arabidopsis* when functionally linked to SEQ ID NO: 210 (illustrated in FIG. 26*a*), thus the promoter of this partial DRE sequence is putatively classified herein as a root as well as a flower tissue-specific promoter.

The GUS gene was expressed in a root-tip tissue specific manner in *Arabidopsis* when functionally linked to SEQ ID NO: 213 (illustrated in FIG. 26*b*), thus this promoter is putatively classified herein as a root tissue-specific promoter.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

What is claimed is:

1. An isolated polynucleotide consisting of the nucleic acid sequence set forth in SEQ ID NO: 61.

2. A nucleic acid construct, comprising an expressed nucleic acid sequence operably linked to a regulatory sequence consisting of SEQ ID NO :61.

3. The nucleic acid construct of claim 2, wherein said expressed nucleic acid sequence is a reporter gene.

4. A transgenic cell comprising the isolated polynucleotide of claim 1.

5. A transgenic cell comprising the nucleic acid construct of claim 2.

6. A transgenic non-human organism comprising the isolated polynucleotide of claim 1.

7. A transgenic non-human organism comprising the nucleic acid construct of claim 2.

8. A transgenic plant comprising the isolated polynucleotide of claim 1.

9. A transgenic plant comprising the nucleic acid construct of claim 2.

10. A method of producing a transgenic plant, comprising transforming a plant with the polynucleotide of claim 1.

11. A method of producing a transgenic plant, comprising transforming a plant with the nucleic acid construct of claim 2.

12. A method of expressing a polypeptide of interest in a cell comprising transforming the cell with a nucleic acid construct including a polynucleotide sequence encoding the polypeptide of interest operably linked to the regulatory nucleic acid sequence set forth in SEQ ID NO: 61 thereby expressing the polypeptide of interest in the cell.

* * * * *

SEQUENCE LISTING

```
<160> NUMBER OF SEQ ID NOS: 214

<210> SEQ ID NO 1
<211> LENGTH: 1611
<212> TYPE: DNA
<213> ORGANISM: Arabidopsis thaliana

<400> SEQUENCE: 1
aagcttatag cgtatacgtg tgtatatttt tagtgaggaa cagctggatt ttgtggaaag      60
caaaataaaa gaagaagttt gtgttgtctt tgtttttcat gtgcgtcggc ttaaatttag     120
gccgttgtaa attattgaaa aagtggattt tgttgtgacc gtggaaactt tagttaatta    180
atttggctaa ttatagagtc tgcttttgtt tggataatca atttgtcatc tttttcttta    240
atggtttttg gctggtaaat actcatacta tccaagttta atctaaaaat atacctcttt    300
cttgttaatc gtaattttac aatcctaatt ttatccagat acggatgaac tatatttgaa    360
```

-continued

```
aaaaaggaac taaagtgaag ttaagaaaac aaaagagaga tcgagtgttg ttttttcttg    420
gatacgttta ttaaaagatg ttcttaatga ggtcaaagga gactatctga gtttttactg    480
ctaaacttaa aactaaaaaa aaaatcgatt agtaatattg atgtatcaac gaatgtata     540 tggttaaata ttaagtgaaa agaaaaagaa gagagatcga cgcggtttgg gataatgcca    600
ttggcccatt ggacacgtgt ttgtaggagg aatagtttgg agtttgaaca ctacggacca    660
aagtcaaaga gattcgaagt atgaagatgt tgttgaggaa gctgattcga agtaacttt     720 accgacacgc tttagccatt tgttatgctt tctttgggaa aagaagatcc gcgtccatgt    780
ctcattgtta acagtttatt gtcattttca atgacatggt tacactcatt gcacacacac    840
acaaaccacg taattttgta tttttttaat taaatcccat ccttatttt tgcaataaca     900 aattaccatt gttactttt aatgatatca cataaaataa tcgatgccac tcgatagccc     960
tttagactaa caatatgttt gttgaagtat gccacaatgt ttgaagtgag ccggctcaat   1020
gctctcatgg tggtttagta gtttaacttg agaacttaca acagttttct ccttctccac   1080
actatttgta tccaagaagg ggcattacaa tatagaattg cataatacga tttaaacttt   1140
taccaaaaaa aaaaaagaaa aaaaaagaaa gaattgcgta atacagaatt tatctttaag   1200
ggaatacaaa tataatttgg tttcagaatc atctcaatag gctttccttt aaccaaactt   1260 gggtttatt gatgtgcttg ctttaatggg cctaaagccc atacaacagc atcactatcc    1320
acgccgttgt ctattcttat tattcacccc acccggtaca ccgaccaaac cttggccaac   1380
acgtccataa tatttcatcc tccctcctaa tttactttaa tatcctcaac tttcctaatc   1440
gttcagggaa tattctcata taccctagac atatgcgtct tttccaatct aaaatgttga   1500
gagtatattt ttatttatat atatatgagt gaccccctgcg agagacaacg gccactgaac   1560
actatcgatc taatcttttc agctctctcc atcgtcgtcg tatctgtcga c            1611
```

```
<210> SEQ ID NO 2
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 2
ccgttttgta aagcttatac gtgt                                            24

<210> SEQ ID NO 3
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 3
gtgtcttgat aaagttagcc ac                                              22

<210> SEQ ID NO 4
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 4
gatcacgaga gtcgacagat acg                                             23
```

```
<210> SEQ ID NO 5
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 5
caattgagat gctacacata cc                                               22

<210> SEQ ID NO 6
<211> LENGTH: 901
<212> TYPE: DNA
<213> ORGANISM: Arabidopsis thaliana

<400> SEQUENCE: 6
aagcttctat aagtaaaaag tgatccatcg ttcataagct ctactatagc aattgacggg      60
acaggactca taagtaacaa caaagtacac ttcgaaacaa atttcacatg taatacttgt     120
ttttttttcc cgtttaaatt cacatgtaat aatttaattc acgtaaatac taaagtgatt     180
cacccatcac gaagtatttt ttgaattaaa tacatcaact aatcgagttt ttgatatggga    240 cttttgcttt tttgaatatt gcttatcaaa tcaaaatttt caaattcttg tccatatacg     300
cctatcaaat atcttctttt aaagaaagtc tcctaaagag ttgaaaactt gaaatatata     360
cttttctaaa atataatttt atttgggcgt tacgttctag aaaatggaac ccgtctacta     420
aaatgggccg ctcgtgaact cgtggcagtc aaacactggt cggcgcataa aagcatatcc     480
aaatacgctg cgtttcatgc ttacccgacc cgtcttaaat atttaaagaa tattccagat     540
tagcgcgtga gatgcagttg ccatgtctcg cctcaggaat gacgcatttt gccaaaataa     600
cagagctaca acggtaaata aggaaaatga ttaagggcaa tttggtcttt taggttaaga     660
aaagtattga atcagatctg acttttggc caagaaaaac tctcagccac tagatcattc      720 cgaccctcc tccacgttct tctctctttt aaataacctc ttcacggaac ccttctcact      780 caccatctc actctaaaat ctctctctgc caatctcatc ttcaacctct ctctaactct      840
cgttttcgat tctacaatgg gttagtctct cgcttttact aatctctcgt cccgtggatc     900
c                                                                    901

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7
tcatacgcgt caagaggtat ca                                              22

<210> SEQ ID NO 8
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 8
tggagaacaa ctctagcaac c                                               21

<210> SEQ ID NO 9
<211> LENGTH: 23
```

```
<212> TYPE: DNA
<213> ORGANISM: Artificial sequence
<220> FEATURE:
<223> OTHER INFORMATION: Single strand DNA oligonucleotide

<400> SEQUENCE: 9
acgtaaaata ggatccacgg gac                                             23

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
gatcattggg aatgttgaaa gg                                              22

<210> SEQ ID NO 11
<211> LENGTH: 2192
<212> TYPE: DNA
<213> ORGANISM: Arabidopsis thaliana

<400> SEQUENCE: 11
aagcttaaaa agtcggtgaa tgaatgggtc agctctctcc actttcatta tctctctatg     60
ctctatctct ccaatcataa aacttgctat tccaattaaa cttatacact atccattagt    120
attttatgta gtattcttat taagatattt taacgtggtc catcattcta cttaataagt    180
ttttctcttc ttttaaattt attggcagca gtttgagaaa acgattagat tgattaagaa    240
tgcaacgaat gtcaaatccc aaaccattat cttataccag ttatattatg agtgcttcat    300
atttatatat taacttgcca aagttttgaa gattatacta tgaaggctac tcaaagggac    360
attgattcct agaagatgat tttatgatgt taagccgttg actttggtaa ctaaatcatt    420
tgacctttga tgtttctgcc cccttttagca aatagaaact taataagaaa attttcattg    480
aaatttagca tcccaaagaa aggtgtagaa aagttatagt gtaatgtgat tggtgaggtg    540
catgttcgac actcttcaaa tgttgattga aacttttttt tgtgtgcaaa gttgattgaa    600
actttaatat tttttcatta atcgcttaaa gtgtagtagt gtcaaaatat tgagatgtca    660
agtatagaac atactatcat tttcaaaaca attgtgcaat ttcagtataa tcagtattta    720
aatcattaat aacctcatgt gtaattaact ctattatatt atcgatttta aaacacaagc    780
cccaagacaa tgtccctcat tctatctcat caaatgctca actttttttt tttagtaaga    840
acattaattg ggtgcattaa tgaaggtcac agaaaagaag ggttatagag ggtaaattaa    900
aggtgattgc acacaaaagt atgtctttca gttttttcaca gaggaagctc atgcacactca    960
ccaaagcagc acgaatgaag ttcaagttct taattaggct tcacatactc tacatcatct   1020
cctcaaaatt tatatcattt catatgttcg atcttgtttt catgtgactc tctcctcttc   1080
tctaccgtga gtctcttcaa tttcctaacc ctttgttaac gatcatatat accttgtttc   1140
tcgccgtact atttcatccc aaatttact tttaccactt gcgataatat atcatgaagt    1200
ctcttcttct ccttgccttt ttcctctctt tcttcttgg ctctctcttg gctaggcatt    1260
taccaacatc ctcccatcca agtatgtatc tatgcacatc tttcttactc cagctctttc   1320
actatcttca agatctctaa cttgttcatg tctgcgtgca tgtgcaggtc atcatcatgt   1380
aggaatgacc ggggcattga agcgtcagag gaggaggccg gacacggtgc aggtggctgg   1440
gtctaggttg ccagattgct cacacgcgtg tggctcgtgt tctccatgcc gtcttgtgat   1500
```

-continued

```
ggttagcttt gtgtgtgcat ccgtcgaaga ggctgagact tgtccaatgg cttataaatg    1560
catgtgcaac aataagtcct accctgtccc ttgatcagcc tcttctacac ttattctatg    1620
cattcaaccg ttttgttttc cttttgcttc tccgggacat gaccatgtgt acgtatacaa    1680
tgcatcttta attagtttct ttcttattat taataggaat cttaaacaca gtttgatccg    1740
agattaatta atcagaaaat atatggatat caaaaaatga aagccactca cctatttggg    1800
ctctctcgct gtattatggt ccatgaggcc gtatttaaga cagcaacaac aaaagttgta    1860
gacagaatta tatttaaaag gcaacaacaa aagtacgtat acgttgttac caccaaactt    1920
tggaggctcg ctaataataa ccacactacc catttgttac acacccttta ttttcaacca    1980
tatcatctca ccttcgttaa atgttcccac aattagctca gtattttact atatacatac    2040
acacacattc cctccacagg atcaaacaaa cacacgagct ttctcctcta caacaaaata    2100
aaataaaatt aatggcttct tcacttatca cctccgcagt cattgtcgtg gtttttaagcc   2160 tagtgcttgg atctgtagag caagtgagtg ga                                  2192
```

```
<210> SEQ ID NO 12
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 12
atgcacatcg tcgacagtat ggtc                                            24

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 13
gactcaagac accaaaacag ac                                              22

<210> SEQ ID NO 14
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 14
ggaacgtgac gggatccact cac                                             23

<210> SEQ ID NO 15
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 15
tggggcttaa ctaagatgtt g                                               21

<210> SEQ ID NO 16
<211> LENGTH: 1975
<212> TYPE: DNA
<213> ORGANISM: Arabidopsis thaliana

<400> SEQUENCE: 16
```

```
aagctttact ttgtttgaaa aaatatcaaa ttgtttataa gtacagaaaa ctaaaccta        60
agaatggtag ggaacccaaa caacaaaatc tgaaaccccc aatttagatt ttgtaaaatt      120
tgaagttttg cctctgtaaa tcaaaacccc aattcaattt aatcaaaaac cctataagtc      180
acttcaggaa attaattgca ttgcttccat cgtcaatata cctctgctga ttgttggcaa      240
aattagaagt ttcagaaaag gtggactgca acttattaga gctaaaactc tgtttgaaag      300
ttaacagttg gtgaaagaga agaattgggt tcctgcgaaa agaagaagat gatgagcgtg      360
tttctcaaac aaggataatg ttgccattat tacaaaaaat acaaacaata tacgttactt      420
ttttgtggag tgttagtttc ttaaatataa tatttttgta gattataagc ccaaatttct      480
ctaaaattta catacttcta tctaataata gagttacata cttctatcta aaaagtataa      540
tagagtcaca tacttctatc taatatgtaa caatataaca taacacgtaa tttgttttat      600
tatgaaataa aaatcatgta attataaaat aaaaatacat gtgataaaat tgtctagtga      660
ttaatcaatg gttcctacac aatgttctaa atattttagt aaattttact agctaataga      720
tggaaactta tcgcatgtta caggagtagt tcatcgtggc cttagtaagt tattgataaa      780
gttgtccatt ttatgtgttg ttgtcaaatt gttttttgttt tttgtatttt tttttgaata     840
agttgttatc aaattataat gtctaatact actatagaaa tttatcactt ttatcctctc      900
tttttgttat gtcttttttcc tttcaaaatt gcataccatt ttgtattctt ttctcaccaa     960
acttattcaa actaaatttc caaacatatt atagagaact atcaaaatac aaatagttac     1020
ataaacaaca taagtacaaa caaaatcacg agaaaaagtg aaattatatt acaaaatgct     1080
atatttttt ctcacactct atattaatgt caaatatgag taattcaat caaaagccat       1140
ttttcttttg cataattcat gtttatttt ttattttttt catcttgcat aattcatgtt      1200
taaaaggata tatacatggg tctactacat tcacctgaca ttacgtttta tgtgtttgtc    1260
ttctgaaaat aatcatcaaa atatttcagg acttgtttac gttttcagga gaaaaaaaat    1320
aactgtaccc ttttcaatat agaaataaca tttgtagaaa tcgtggattt tccttaataa    1380
acaatccaaa acacgaccac cgttgtctcc tcgactcggt aacacccgat cgccgacttg    1440
aaaattagaa gaaaatgaa aagaataata aaaaaaaaa aggaatgatt attgaagctg      1500
tcatatatgt cgaccctatc acagtcaatc caatagccta tattcgccaa ctgatatatc    1560
caacggctca caaattttca caaactttc aaaaagtat aaataaaaga ggctgtctga      1620
cagccatgtc acgttatact ttttccgtat gatcgaaatg attcgtcttt gtcgaattta    1680
attatttcca aaattgatga ctctaaagaa aaaaaatag ttttcagat aaacccgcct      1740
atataaatag ttcaacactc ggttttatttc ttctcccctc tttgaattgc ctcgtcgtct   1800
tcagcttcat cggccgttgc atttcccggc gataagagag agaaagagga gaaagagtga    1860
gccagatctt catcgtcgtg gttcttgttt cttcctcgat ctctcgatct tctgcttttg    1920
cttttccgat taaggtaatt aaaacctccg atctacttgt tcttgtgttg gatcc         1975
```

<210> SEQ ID NO 17
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 17

```
acaatgaaga gctgaggtga gc                                                22
```

```
<210> SEQ ID NO 18
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 18
ggatcgattt caaatacaac g                                               21

<210> SEQ ID NO 19
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 19
cgtaatcggg atccaacaca ag                                              22

<210> SEQ ID NO 20
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 20
tcaaagcgaa cagctaaaat c                                               21

<210> SEQ ID NO 21
<211> LENGTH: 3126
<212> TYPE: DNA
<213> ORGANISM: Arabidopsis thaliana

<400> SEQUENCE: 21
aaaagtcaga aactctcata cctccccaac ttgaatttct tttgcccccT cctcctttac       60
tatcttggcg agaaaaccct cttccatgca ttccatttcg actgttgctt tgtcctaaaa     120
tattaagatt gagataagtg ttttattcct ggcataagaa tcaatacagg aagagattca     180
atcaggatta tcattacagt ttcaacttca caaagcactt caccaggagc aactttatca     240
ccttctttct tcagccacct ggcaatgtta ccctgaagtt tcaacagata tctttagtag     300
aatgataaaa caataaacca tgttaatttt cgtaagaggt attcagaggt acatgcctca     360
gtcattgttg gcgaaagaga aggcattcca atctcttgat gaggaggaag atctgaaaca     420
tattttaaaa agttatcagt aaaacaaacc atgtatgctg catatacaca gtgacagaaa     480
tatgatggcc gcaaaggca caaaaccaa gtcagatgct cacaaaaaaa agtacaattc      540
aagtgaaaat atatgttaga caagcggga agttacaata agaactaaa tacctgaact      600 ggatgaaaat cctctcactg atcgcatctg ggagctaaaa gcaagaaaag aagcttacag     660
ttaggataga agtattcata caggaaggta gcaagttgta ttctcatcgg taaatggatt     720
acataccttA taaattcttt aaatagtttt ggtcctgcca ttgggctgct tagttttgtg     780
ctcgttgttg aaataccact aagcattgtt acctatataa tgcagctaat gacattacga     840
ccaaaaaaac acagacgatt acgtgacaaa gcaaagacga gaaggaaac tgaacagcag      900 ggacttacat tgccagtacc acattttgaa attctctcta cagaggaata attcaggcgg     960
gccttgaaga tatctgaaga ccaaataaaa atagaaaaat aaatgcttaa gcgagaagca    1020
taatatatac tcaaaacata ccaactttca attaattaaa gttggaacgt tgttatgttc    1080
```

```
ttcatgttga aaacgatgtg aaagtcaaac ttggactatt catcccagag tactgtgtgg   1140
tgcttgttac cgtatcaaat aaaagaaacc accacacatt tctacataaa atgaacttaa   1200
ggatagcaat gaagaggaca ctaagaaagc tgactggatt accttctctt ccaacgagag   1260
aggggtgggt actgttggag aaacagcgga ctgccacagc atggtcacgc cgcagtaaag   1320
cggaaacatg tttcaactgg tcagataaca caacaatcgt caaatagtg tttacaaaga   1380 gcaacataca attactctgc tgtaaaagta gagtcttctt gtactaataa aatgaatagc   1440
taataccaca attgaatcat aaagcgaagc tactacatta atcacaattc agattacaag   1500
gaggttacta aagctctcaa tagcaaaatg cagaattgcc catgatcaaa ttaaaaatac   1560
caaattcatg attagattaa gtcaaacccg gaaacgaac ctcagttcag aaaaaaatga   1620
ttggcagagc aaaacacata agaacgaatg cataaactca gttttacaag atcaaaaatg   1680
gtagtcaaac cacagaaaaa aatgaaaaat agagaaagag aaaccttttt ggaatgattg   1740
atgatacgag aagccattgt tgtgcaatcg gagctgcgtc agccgatccg aattcgcaac   1800
tgcaaataac aaaaaaaatg gtgggaatgt tgttagggg gtttctcctt tttccctcgg   1860
caactatatc agagatcgag atcgatgaat ttgacttgta ctcaatccaa ttttgaaaca   1920
gtaaatatgt ggatggaaga taggattcga tctagaactc accaagagtc agaagaacgg   1980
taaatcgcag tatagagagt gaaggatcac ttggaagaaa gctgggattt gatgatgatg   2040
atgaagatag ttttgtgttt aggtttttca gaaatggcaa aatgctgcct tacatgtacc   2100
agattgtatc gtaccaacac caattctacc ataaccgata taaagtatt taaaccgact   2160 aattaagctt cacaaatttc ggtttgtact ttattatatt gggccctatt attattctct   2220
gagcttttgc gtctcaccaa aagacagaga tcatcaggtg cgttagtgat tacgtaggca   2280
tctaatgaac ggcagggatt agtcaaactt attaatgggc ctaatctttg gcccatcgtt   2340
ttccctcgat tcctgtcaca caaaaaactc ctagctcttc ctctacctac acaagctaaa   2400
tacatatttt ttgcttatcc taagcatcat gattatgttt tgccctctcc agcttttttct  2460 tcaatggcaa cagattctaa gaaagtctct tgaggctaaa atcaaagcat tttttgttga   2520
agatagatag caacttgctg cttcttcata ctagctagtt accttcttct tactcaatgt   2580
gttttgcttc gtttcaagga ttcttcatat cacttgtgga acaattacat gattaaacat   2640
tcaacataga gagatagatg tgttaataag taaagacatt ttcagataaa acgttcttat   2700
cagtcacttt attcttctaa tatcctcgtt gtaatcggga aaatgctttg taacgtcaaa   2760
aagcaataaa agttgcagga gaaagaaagc tttggaaaag aaaataaaat aaatgaagaa   2820
tattttcttt gctagtcaca aaataaatga agaatttatg ttcctaattt cccactagat   2880
atttgtttat ttatttttgc caaaatcaag ttaagacaat gagctaagtg ttggaaaacc   2940
ttgtccgagc caaagagta aaagaaagg gaataaggg gtaaaccgg aaatccgaaa   3000 aagaaaagga gaagatttcc aaaggagaaa accctaaaga cggagtatat aaacaaggta   3060
acgcgttttc tctcagcctc tttcggatat tccaccagtc tctcgcaatc ttcgctcttc   3120
tctttg                                                              3126
```

<210> SEQ ID NO 22
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 22
taattaacaa gtcgacaaaa gtcag                                           25

<210> SEQ ID NO 23
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 23
agagactaac ctagccgtaa c                                               21

<210> SEQ ID NO 24
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 24
gagagaggga tccaagagaa gagc                                            24

<210> SEQ ID NO 25
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 25
cttcatcttc aactgtgata gc                                              22

<210> SEQ ID NO 26
<211> LENGTH: 2501
<212> TYPE: DNA
<213> ORGANISM: Arabidopsis thaliana

<400> SEQUENCE: 26
ggtacgttat attcggggta ttttggcctg agaaatttgg agatagtaag aatggttgca      60
tcatgagagg aacaaatata acgtcccttg gcggctgctt gttcgtataa gaagatatga     120
gcgttgcata agtcgtccaa atgcacatac tgtccttgtc ttatgatcga gtaatgcgcc     180
tcgttcccta aaacattata atatattcaa cgtttagat ttaacatttt cacatttcca     240 acaaagaag aagcacacac acgtacgagt gataggagag agcgcggtga taaggctagg     300
cggcatagac gttgtgatga atggaccgac caccaatgtt ggaataatac taatgaaatc     360
taatcctttc tcttcggcga aatcccacgc tgctttctcc gctaacgttt ttgacacgaa     420
atacatctgc cacacaaata tatatgaact ttaaattact tcaaaaaacc gtaacttgag     480
tttaattaat atgtatattc ttacccatcc tgtcatcttt ttggacatga taaactcaag     540
atcactccaa tcattttcat catagacatt cttctgatgt tcttctacat taacggttcc     600
ggcagatgaa gtaaatacga atcttcgtac ggtctttgcc ttaacacatg ctttcattat     660
ccccaacatt ccattcactg tcggctttat cacttcgttc tgattcgcaa atacaaaagt     720
caagttaagc taggttgacg caaaaaccaa aagaagtttc ctaatataga gaaactcacc     780
tcaggatctt ttgattcaaa atccatgggt gttgccacgt ggaaaacacc gtcacatccg     840
tttatggcat catcgtagct tccttcctca gataaatcag ccttccataa agtgagtagc     900
gtcttggcgt ttggcaaatc aagaagatgt tgtactttct tcaaattacc ttgacaatcc     960

-continued

```
aaaaaaaccc gtaaataaac gttatattaa tatacataat cttaggagaa atgagtttgt    1020
aagaacatat agatatgtac cgggatctcg aacggtggca cgaacaaagt aaccacgttc    1080
tagtaatcgc atcactagcc atgaaccgat gaaacccgaa gcgccggtta cacacacggt    1140
ctctttctga ctaaccattt tgtggttat atgatagatt gtgctttggg aaagattcaa     1200
ctatgtatgt tcggtacaaa tctttgtgat gtgaagacat tataaataag acactagaga    1260
ttatgaatcg ttattgaaga aaacagataa taagaacgag aagctgccgg tcacgtgagt    1320
accaaccgga gaagcacgtg gggaacgttg gttgacgaag gactaaagag atgtgtggta    1380
cgtaacaatc tggtaagttg attttattat ttccttaggt gtgtattttg ttgttgtacc    1440
ggtgggtgaa atacgttgac ttcgatttgt ttggtgagac gtgtgggtga cttcagttca    1500
gtttgttttt gttttgttc cccacccact tttacgaaat aaatcaaaat ttgtctaaac     1560
aaattaacat tttgatagaa tatatacaga aatacatttt acttaagtaa tattttaatt    1620
ttaattgaaa tctaaaaatc agacacctaa aataattata aatcttggaa aagcttaaat    1680
gaaaaatatg tttatatttt agatttatga attaggagtt tcttattaca aaattgtaaa    1740
attataaaac atattaattt ataaatatga cttctagatt tattgcaatc taaatattat    1800
aagcatttac ataaaataca taaactaaaa ctttaaaaga tgtaattatc caattgtgtc    1860
ccatgtcagc tttttcatta ttatttcacg aattattata aaaataattg atatgttaaa    1920
atattgtttt caaaaattta tttatttcca gttttcgcaa agaaaataaa ataaaattag    1980
aaggacagtg aatcacttaa tctcataaag taagaaataa cacgtggtgg ttacctcgtc    2040
cacgtggatt ctaaaacaca gaatcaatat aactcttgta ttttcaattt gttgtatcgt    2100
aagacgtcag agaagaggtc agcttaattt tgactctcct ccaaacagag agacaaagta    2160
agccaagcgt ctttggtgta gtccaccacc acgtttgagc tcgacgcaga gagagaagaa    2220
tacttcaaag ctctccttct tcttcttcaa ccactagaaa tcttcgttct ctattcaatt    2280
gcattgcgtt agcaaaattc tggtgaattg atttgatcag atcttcgctt gatttcgatt    2340
ttaaaaatcg aagaattttg tatcgcatgg agatgatttt ggaggagaaa gatgcatcag    2400
attggattta cagaggcgaa ggtggtgcca atctcgttct tgcttacgct ggatcttctc    2460 cacttttgt tagtctcttc ttcttcgatc tctcttcctt t                          2501
```

<210> SEQ ID NO 27
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 27
aaaggaagag aggtcgacga ag    22

<210> SEQ ID NO 28
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 28
ataccatcgg ttaaaccatc tcaag    25

<210> SEQ ID NO 29

<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 29
ggtacgttgg atccggggta ttttg        25

<210> SEQ ID NO 30
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 30
tcttcataga agaagagagc cac          23

<210> SEQ ID NO 31
<211> LENGTH: 513
<212> TYPE: DNA
<213> ORGANISM: Arabidopsis thaliana

<400> SEQUENCE: 31
gtctctctga ttctttcgta tggttggttg caggcaacgg tgggatttac tttgtttggg    60
aaggagacac tagtggaaat tgacatcaat gaacttgttc ctgagattca atcttaaata   120
gtttgttcac tagaatgtga atttttggt ttgaaatata aatccatgat cacttcacat   180
gttttggaag ttttggtgtg tttgttctgt taaattcgcc aaacgattgc aacgacgacg   240
ttctatcttc atttgaaaga tgagagcctt tactggttaa atgggcctaa tttgtgaaaa   300
ggcccaacaa acaagagccg tcagatcaga atgaagcaaa caggcacgaa ccgttagatt   360
aagattcaca agaaaaccc tagaggttcc cttatcctca ggccaaatcg tgaactataa   420
aacggctgat accaaaaccc taatttcttt acgtcaaact ctctctatac acagagttaa   480
attgagtttg tgtctcgtaa cttatcctgt gag                                513

<210> SEQ ID NO 32
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 32
gtctctctga agctttcgta tgg          23

<210> SEQ ID NO 33
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 33
tatccgaagc tataatcaca ca           22

<210> SEQ ID NO 34
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 34
ctcacaggat aagtcgacga gaca                                    24

<210> SEQ ID NO 35
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 35
caagagaaag cagatagtga gta                                     23

<210> SEQ ID NO 36
<211> LENGTH: 1022
<212> TYPE: DNA
<213> ORGANISM: Arabidopsis thaliana

<400> SEQUENCE: 36
tagagaaggt ccggagaatg gaagaaagca gatctatctc cggcgcttct ccattgtttt     60
tttttttgctg ctctgaagct tagaagctaa aagaagccgc gaagaattgt gaagaagaag   120
gaaagtttcc attattgcct tttattttat tttatttaat aatttaaggg ttttgatttt    180
taaaatgaat aataataata aatacaaaaa agaaaggaca gaaggaagga gtgatgtgtg    240
gtagagagag acagttcacc gtcggcgagt ccagctggcg gtggtgggag cccaccgtgt    300
caccttaatc atcgctgcgc tgccctgtct ttttccatt attaatttt agcaagaaga      360
agactgggct ttctaaatta gttattaatg gctttgggc tttcgtggtt agggttgtgt     420
aggggcttaa tcgtcattc ggagataaga taaaccctaa tctccatgga tgggctctcc     480
gatgtttgtc tttttgattt ttgaaatttg attttcaaaa ataaactaaa gcatcattgc    540
ctcccattat cgtcacgcac gcagatcaat gattctctca ctctgcttct cattcacgct    600
tcttcttga attcactttt ctattccttt cttttctcc gtccgagaga gtatagagag       660
acccatttct tcgatccatc cgctgagaaa aaaaaggtac cgtcgtattg ttctctcatg     720
tttctgggtt tcttttttgtt tcgaaatata ttcttctcgt ttgcagtgtg attttgaggg   780
tttccttgtc taaaaaatgc agtttttaat taatggattt acaatagaaa tgtagttaga    840
ttcttcgaca ccatcttcgt tttcgattgg atctacatgt tatgctctct ctttttcctt    900
ggaatactat gtcagattga gtaatggttg tccttgtatt gaattacaga agaaaaccaa    960
gcagtagtag aatggatcat tcagcgaaaa ccacacagaa ccgtgttttg tcagtgaaga   1020
tg                                                                  1022

<210> SEQ ID NO 37
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 37
gttggttcgt cgactagaga aggt                                    24

<210> SEQ ID NO 38
<211> LENGTH: 21
<212> TYPE: DNA
<213> ORGANISM: Artificial sequence
<220> FEATURE:

<223> OTHER INFORMATION: Single strand DNA oligonucleotide

<400> SEQUENCE: 38
gcaatgaaga tgatgatgtg c                                        21

<210> SEQ ID NO 39
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 39
cttactcggg atccacatct tcac                                     24

<210> SEQ ID NO 40
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 40
aactcctgtt gctaaaacgg a                                        21

<210> SEQ ID NO 41
<211> LENGTH: 1056
<212> TYPE: DNA
<213> ORGANISM: Arabidopsis thaliana

<400> SEQUENCE: 41
gtcgaccctc ttttggattt atatttctct tcagatcagt tatttgaggt tcttgtgacc      60
ttgccaataa tattccgcca cctggaccgt aatcttgtat tactctcaat tcaagaaata    120
tacatacact ccaattttta tcttttttttt tttctccgaa taggaaatcg atactctttt    180
tatgcccgtc gttacataat aatcgtttgc ctttacacgg ataaaaatcg aataaaatcg    240
aataagtaca gaaatagtta agattcgttc aagatactgt ttctttaaga aaaaacaaat    300
tataacgtta ggctacaata ttaaaagcat attagcatgt agaaaagatg tataaaacca    360
tcaagagtta atatgtagca ccgtggacca taatattaat tagtttataa gttttttttct    420
tgaattgcaa acgtcttgta tatcactaat ttactataca tattgtcata atgttgaact    480
ccaggacaga aaacataaga caaacgcatc attttcaatt aaaaatagtg gcaacaggct    540
tataaagata caaagatggt gttttgataa gagaaagaaa aattatgagg ttcgtatcat    600
ttctaatttt taattttttaa gagctgccga gattattgat cagattagct aatgtctaaa    660
tttgacggta gagagtttac cacgtcaact acacaagagg acctttggat ccggaaagag    720
gtttcgttag tctgggtctc aagtttctca accatagact tatatgctaa tccagtgaac    780
ccatgattat gaaaacctat taaaattttc cttttagaa tttagagcca agatgcgtc    840
tgaaagttac actcaaagag aaagattttg tgaggacgta gttccctgcg ttttcttaag    900
gctgaggtta agtactggga tttttaagag attgtgaagt ctacatcatc agtcgagaga    960
cactgcaatc tcatcgtcat cattgcacaa caggtggcca agtggatgtg taggcaccaa   1020
attgacccag taaaccttc ggtctggtct aagctt                             1056

<210> SEQ ID NO 42
<211> LENGTH: 23
<212> TYPE: DNA
<213> ORGANISM: Artificial sequence

```
<220> FEATURE:
<223> OTHER INFORMATION: Single strand DNA oligonucleotide

<400> SEQUENCE: 42
cccttatctc tcagtcgacc ctc                                            23

<210> SEQ ID NO 43
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 43
gaagagagga tatgtgtgaa g                                              21

<210> SEQ ID NO 44
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 44
ttcaaaataa gcttctagac cagac                                          25

<210> SEQ ID NO 45
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 45
aagagatttt caaagtgtgg                                                20

<210> SEQ ID NO 46
<211> LENGTH: 435
<212> TYPE: DNA
<213> ORGANISM: Arabidopsis thaliana

<400> SEQUENCE: 46
aagcttatta cttaccatgt atgttccaat aagaaaagtt tccatctttg cttaaaagca    60
aaaaactaaa ataccaaaag attcaaaaaa aaaccaaaac agtaaaagta aatagcaatc   120
tctgagaatc ttatccacgt cagctcacgg gtcctacaga gaaagctaca ataggaagag   180
atgttttcac ttacagaaga tttacttggt ctagatttgt tctcctttgt gaaggttatg   240
agaaaaaaac tttttttgatg attcatgacc ttgttcaaaa ctcagacagc cacaagatga   300
tccaactact tttaacaacc actaactctg cgccacgtgt atatctccaa agattctatc   360 tttccccctct caccacctag atatagtctc attagccttc cctcctttct aattacaatc   420
tctccttttg tcgac                                                   435

<210> SEQ ID NO 47
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 47
gcaatgattg tcgacaaaag g                                              21
```

```
<210> SEQ ID NO 48
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 48
ccggagaggg atcctacgaa agt                                          23

<210> SEQ ID NO 49
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 49
ttggtcacaa gcttattact tacca                                        25

<210> SEQ ID NO 50
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 50
gggaggagga tccagccac                                               19

<210> SEQ ID NO 51
<211> LENGTH: 3333
<212> TYPE: DNA
<213> ORGANISM: Arabidopsis thaliana

<400> SEQUENCE: 51
aagcttgcca agtacggctg cttcaatgct tcatccactg tcaaattaaa acatattgtt    60
agtatatttc acattccatt tatagcatca caaagtagta aaacaacgtg ataagcacct   120
gtgatgcgct ttgaaggatc gaaaactagc atcttttcag caagatctag agccattggg   180
gaaatgtttg gaaacttttc tctgaatgat tgttttttgaa catgtgggag ttgttttacg   240
tacttccgcg cattatcgct tctcaagaag tcgagatccg agtcatctgg tgaccctaag   300
agctaaaaac aacccaaaac aaaacagaga aatgcttcca acaaccaaca cacacacaca   360
cacaaaccaa aatgatagat tttggattaa ggttttaatt tgcttacctc agtaataagt   420
ttcagctgct gaacgtaatc tttaccaggg aaaagcgtct ctcttctaag tatctccatg   480
aaaatgcaac caacagacca aatgtcaata gctcctgtgt attcagagct gttgagaagc   540
aattcaggtg cacggtacca tctcgtcaca acatactcag tcattatctc tgtctcattc   600
gacgttcttg ctagcccaaa atcacagatt ttcaggtcac agttcgtatt cagaaccaag   660
ttgctcggtt tcagatcgcg gtgaagaaca tttgcagagt gtatgtactt aaggcctctc   720
aaaatttggt aaaggaagta ctggagacaa caaaaaagta tatcaaacaa tgctaaatgt   780
taggaaacat tatgtaaaag ctctaattag gaatgtgtcc actgatcatc acctgacaat   840
ggtcatcagt tagagtttga gtggatctaa tgatctggtg caaatctgta tccatcaact   900
cataaacaat atatacatct tcgaaccttt cttttctctgg tagctcaatt atatctttaa   960
ttttgataac ctgtgtagca atatgaacgt aataagccaa ctatatgagt gttcatcaaa  1020
gtgaagaaga agagattaca ttgtcatgat ccatgtggga aaggagcttg atctctcgga  1080
```

-continued

```
gagttctttt agcatcaact ctgttgtcaa acgcgtttgc tatcttcttt atagcaacct   1140
cttcatttgt ctctgagttt gtagcacagc tgtaatcata aaaaaggatt tgagattaag   1200
attgtattca agaatggtat gttttttat tgaaagtgat aaagacttac cagacaatac    1260
cataagcacc tcggccgatg ggttcaatag gagggatgta ttttgaagat agctcgaaaa   1320
tgttaccgag tacattgtac ataacatatc taccatcata tgtcaagatc cctccatctt   1380 ccctttctc catctcttct ttggaagaag aactcggatc aagacaggtt ttaagattaa    1440
aaaaggaagc aagttttaaa agactgtttc tcaagtagct gttgttgccg ttaaaaaggc   1500
aaagcagtga gtaagaggag agaaaatggt ggcacctttt gcttttggtg ggccaaatga   1560
agacaaactt ttttatttga tccgttgaac ttcgaaattt gaatgagaat tattattaca   1620
aggttaaaac ttgacttctg catcattaaa gaaaaattca aaagaaacaa aagagaagta   1680
tactatagaa aaagctatct cattgtggat caataggtcc ctaggaacca atagtaagta   1740
aaaagcaaag tggtaaacat acaaaagcga gattattctc aagtctcatt tcaatgtcaa   1800
aactctctct tgtgtgctaa gtaaacagaa cctgtgtgaa agtaaaacac ctctgaactc   1860 atttcacta tctcacaaac ctgcattatc gatccaattc tcccatctta tatcttctta   1920
catattaagg atcagagaag gtgatcaaac ctgataatta tgtagatgta gctgaagcta   1980
agatataagg ctcaggaacc acaaaaacat atcactgaat atttcaaatt agcttcagca   2040
ttttatgagt caaaatacta agaaacaatg caaattctct catgaaaagg ctctcacatt   2100
gcttttgcat tctccgcaat tatgatccaa accttaacca aaaacaacta ccctataaga   2160
gtataagacc atgtctgcag aaatcagtag taacacaaga atttcatgag atattaaaga   2220
agaagaaaag taggccacac aatagaattg aggaatcaag aaaacagata catacacttg   2280
ggaaggacca gcacagcaga cgtctgttac tactaactaa ctcagacttg tcattgaact   2340
atattatata cggctcactt gttttgctgc agtaactggc ttatcttctt ttctggcttg   2400
cgttaataac atgagtagag agaaaacacg acttccgtcg agtagattcc tatcaaacaa   2460
caccggttct cgaatctttc gacaagccaa gcaaaagtag gtgggcatga aaatttgttc   2520
cccatgaaac agaggacatt cgttgttacc tattctaata accgattcaa aattccgaat   2580
cgcagactta ataaatgtgg acaattaacc aaaccgtgca ttgctaggtc taaaccgcat   2640
tggtttatga cccaccaatc aaggagcgat gggtgagaaa cctaataaca ctgctgctgt   2700
gactttatca tatccttagt ccaattggga tcttcgtctg cgtgagacgc gttcacacct   2760
gcgacagatg aaatcacgga ataccactg cccaacgtgt tcgcaataaa agtcctctga   2820
tgcctaattt cgtcaattta ctgaagaaaa ttcaacatca acgcccttt tgataatttc    2880 cccaaagtta gtgggccctc cacacgaagc atgtatcctc caattgcata ttgccaatta   2940
tttcctaata atattgaagg attattcttt tcccatctat ataccaccaa ccctaagatc   3000
cgaacgtcca ttttaaagcc gtgcgtttaa tcatgatcgt caattatatt ggcaaatttg   3060
accacacgat atccgtcatc taacggcatc tacagatcta ccagaacgtt ctcattcatg   3120
actctatata tttcgcattt cttctcctca acgctctcat aaaaagtagt actcgtgtct   3180
tactcgtgcc agccactcgc atttctccag attttattat ccttcctcga aacaaggtat   3240
gacggaaact ctctctctcc ctctctgatc cgtcgttgct gcttccattt tcatcttgac   3300
tcgatcggat cattgttatg cttggctgga tcc                               3333
```

<210> SEQ ID NO 52

<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 52
gatctcatgg aagcttgcca agt                                           23

<210> SEQ ID NO 53
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 53
aaaacagctt catacgagtg g                                             21

<210> SEQ ID NO 54
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 54
cattaagcac ggatccagcc aagc                                          24

<210> SEQ ID NO 55
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 55
tcactattcc ccacagctta g                                             21

<210> SEQ ID NO 56
<211> LENGTH: 1331
<212> TYPE: DNA
<213> ORGANISM: Arabidopsis thaliana

<400> SEQUENCE: 56
gtcgacttgg tacgacttgt aatatgaaat aataatgtac aaagaagttc tacgcttaag    60
ggaactgttt tgttttgagc tttgtattag gacgtctagt gtacaacaac gaacgtcgtg   120
tataagcgat cgttgactct gcacatgtaa ctctttcctg aataaaaat ctttaagtct    180 ttaatttcta catcttttag gattatataa acgttactat ataaataaaa aagaaaaaaa   240
aatcagttca ctaacatgcg agactttggg ctaaatatag tgattccaaa gaaaatgagt   300
tataatatta attaatataa agctcatttt ctttggaata tcgttataag aatattttaa   360
cttggatata actgggctta cgccatttgc atctcgagga ttttttgttt tgttttttgt   420
ttttttaata cattctcgca cttacacact aaaaatcata atgatcttct taattcttta   480
gcggaaccac caattaatct ttttattaag aactttatta cttatttcac ttatttgtgc   540
atacgtgcat tattttggca gtaacaaata tcgcgttata tatactgaaa tccggacgca   600
ttaataatag ggatatgatt atatgaacca ctatctagct ttggtagaaa cccaattata   660
atcaaataat ttaccattat tgaataaatt aggctatata agttcattaa tagatgctat   720 aggttttttct tacaaggcac acatttgatt gttatttct ttcatataca ctgaatgtac   780

-continued

```
atgtgtacac ttggcataca tggcaagatt atgtgttaca atatagactg tgccattgcc    840
atgcaatgtg actcctgtgg ccatttctat cacaatgtgt caatcttgga gtatccgttg    900
tttatcctct aatttactga ttaatttatg aacatgtata attatttata tcatatgatc    960
tcgtaagata tcttagcatt ttccaccata tgttattagt aaatcatcta gatggattga   1020
tgtaaatagg aaagttaaat taacacacca aaaaagtaac tgattaaaag catcaacttt   1080
aatattcaga ttatggtaac taaatcagtc tcatgcaaac tccaaaaaat tatacgagtc   1140
acaactcttg atttttttcc ggttaaacaa aatacatatt ttcatttgta tgcaaccaga   1200
ataaaacact aactatctcc tttaaatacc attttcccta cgagtctacg acgctctcta   1260
aacttcttat acaaaacaaa acacacccaa atatgcataa gcttttgttt tctcttctct   1320
ccgtcggatc c                                                        1331
```

<210> SEQ ID NO 57
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 57
tctaaaggtc gacttggtac gact                                            24

<210> SEQ ID NO 58
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 58
ttaggtcttg atcaaaaagc gt                                              22

<210> SEQ ID NO 59
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 59
agaaatgaga gggatccgac gga                                             23

<210> SEQ ID NO 60
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 60
gcggacagtt actagtcgtg g                                               21

<210> SEQ ID NO 61
<211> LENGTH: 2316
<212> TYPE: DNA
<213> ORGANISM: Arabidopsis thaliana

<400> SEQUENCE: 61
aagctttaag ctccaagccc acatctatgc acttcaacat atctttttct agatgagttg    60

```
gtaaaagtag aaaaagatat gatgatttta aatttgtttc tatttatatg tgttcatcga    120
aacttcattt tttttagttt taatagagag tttatatgac tttaaaaat tgatttaaaa      180 ctgtgtcaaa aattaaaagg acaataaaaa atttgcatac aaccgaaaat acttatattt     240
agacaagaaa aataatact tgtgatgctg attttatttt attatatatc atgaatcatg      300
atcatccaat tttccggata agccaaagtc aaaatgatgg gttcccccta atcttttatg    360
ctgagaaata gatgtatatt cttagatagt aatataaaat tgggttaaag aatgatgatt    420
cgattatagc ctcaactaga agatacgtgt agtgcaggtg tgtagttaac tggtggtagt    480
ggcagacaac cagattagga gttaaataaa gcctttagat ttgagagatt gaaatattcg    540
attggaacct ttctagattt ttacagccat ctaaaattag atgcagatca cctactacca    600
ttcaaaaatg aacaaaataa tttcatttac attttcctag cataagatat aataataaaa    660
tagtgctcat tttaattact ttttctaaat attttcgtta ttttaaattt tgcttgtcta    720
tactctacag ctcattaat aacggaaaca aaaataattg cagggatacg gatgggtagc    780
tttcaaaact tacatcatct tctgtttctt gagatcaact attttggag ctttgtctca     840 atcgtaccaa aggataatgg tcctacctcc ttttgcattc ttaactttat cttctctact    900
tatttctttt ttgggatttt tgggggtatt attttatctt ttgtagatat acacattgat   960
ttactacaaa cgtatactac tatccatctt caactcttcg gaatatgatt tcgaaaaaac   1020
tatgaagatt aacgggtatc ttaaacatgt taagatacac cggacaattt tcatttagaa   1080
gaattgatat gcaattaaca ataaatagtt gatgatcttt tagttttgaa gatgtgcgtt   1140
aagacttaag cgtgtggtaa caaggtggga ctcgggcaac gcaaagcctt gtagagtcca   1200
cttgctcaac ttgtctttct tttatctctt ttccaagtct caagattcaa tgaactccgt   1260
gtaacacaaa cacgcccata gatgagctca ttttggtat ttccaatatt gccactccat    1320
gataatatca tctagggatg gggttcattt attttgaaat ctcaacaaat ctcgtcgatt   1380
ctaacacaca tgattgattt gtttacttac ttgaaagttg gcaactatct gggattaaaa   1440
tttatctttt tctactgcta gctagaagca tctatatatg ttagcctaat acgtggaaga   1500
tgtcattgct aataatggct aaagatgtgt attaattttt cttcttttt ccttgaattt     1560 ttgttctttg acataaacta tgctgtcaaa atgtgtagaa tctttttaca taaatcattc   1620
cctgttacac actaaaaggt tcacaacgga cgattgtatt ggacttccag atcataaacc   1680
atgcaaaact gaaaaccaca agaataatta gttctaactt tagaacgttc gtacgtgttt   1740
catgttcaaa aagcgtcaat tataaaagtt gggaaattac ttttgagttt tgacatttct   1800
aaggacagtc aaatatgaca acattgggat gcaacttacc ttgtattaac ttattttgtt   1860 ataaaccat atattacata ttttaaaggg ttgataaata atcaaatata ccaaaacata    1920
gcttttcaat atatttgtaa aacacgtttg gtctactagc taattatgag aacatttgtt   1980
caatgcatga ttatctagta tctactagtg gattatgaaa attagatatt ttcattgcat   2040
gattatcttc catatatagt gataacatca aaagaatcta caccaattat tgcattttt    2100 cattatataa taagcactaa actgtaaaat tatattcagc cacccaaacc atgacaaatc   2160
accttaaagg cttaaacaca taacagccat tacgagtcac aggtaagggt ataatagtaa   2220
agaatcaatc tatataatat acgacccacc ctttctcatt ctttctggag agtaacatcg   2280
agacaaagaa gaaaaactaa aaaagagaac cccaaa                             2316
```

<210> SEQ ID NO 62
<211> LENGTH: 22

```
<212> TYPE: DNA
<213> ORGANISM: Artificial sequence
<220> FEATURE:
<223> OTHER INFORMATION: Single strand DNA oligonucleotide

<400> SEQUENCE: 62
tagtttggtc agatgggaaa cg                                              22

<210> SEQ ID NO 63
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 63
tataccagtg gagacgaaag c                                               21

<210> SEQ ID NO 64
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 64
aaatattgga tcctttgggg ttctc                                           25

<210> SEQ ID NO 65
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 65
taaactaccc gtcgttctct g                                               21

<210> SEQ ID NO 66
<211> LENGTH: 379
<212> TYPE: DNA
<213> ORGANISM: Arabidopsis thaliana

<400> SEQUENCE: 66
ttcatatgta tcaagacctg taatattgag ttttacaac acaagttata aataaaatac      60
aaacacttta tgagaaaaaa gactattaaa gtgtagatta tggactaaat cttttaaaaa    120
aaagatagta ggttcttcaa agtgtatcct actaaattac aagggtttga acgcaaatat    180
ttctttgaaa atctcataat ccagaaagaa ccaacgagag aatgccacat catccatccg    240
taatcgtatc ctcacaaaca aaatcttctt ctgcttcttc tcctgcttgc cagaatccaa    300
aaccaaacct tcagatcata aatccaaaac cactcatttt tctattactg aaattttcct    360
tagagaagaa gaagaagaa                                                 379

<210> SEQ ID NO 67
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 67
gtcgggaatt attaagctta ctt                                             23
```

<210> SEQ ID NO 68
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 68
actgacgtac tccttagcac                                              20

<210> SEQ ID NO 69
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 69
ggccattttg cgtcgacttc ttct                                         24

<210> SEQ ID NO 70
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 70
gaattatgga ctcttattgg ct                                           22

<210> SEQ ID NO 71
<211> LENGTH: 979
<212> TYPE: DNA
<213> ORGANISM: Arabidopsis thaliana

<400> SEQUENCE: 71
ggatccgaaa cgaagacgat acagtagagt aagagtagcg agcaaaaatg caaacgcatg    60
gtgtttgtga ttgaaccaac aagttgagga aattattgaa cccaaaaaaa gacatatcaa   120
agatttgcta tatatatgtt attttaagcc gcctttacta aatatgtggg gtttaaatgt   180
cacgtgaaat gtctacgagt cacatttgtt catgaagtaa attccacgtg gacatctctg   240
actatataac tgggagttat agttgactgt taaaattggc ttcaaaattt agcaacaaga   300
ggaaatcaac actcagcaat ttactctcat tggatcaaat gaacgcacat taatatgacg   360
taacgatgat gacaattctg tttaatagta tcttattgtt tacagataca gaaaaataaa   420
ttaagtgggc ctttcaataa ttaataggtt ggtgaaatgt taccttctct tgatattttt   480
ttaattttca tttattatga gtatgttgcg ttatgaaaca actcgcatta atttggttat   540
agattggaga aagaagaagt catggtcaaa actcaaaaat gtaaaggaa caagacgtg     600
tatgacgacg tgattgataa tctgaggaga tacctttggg ccttataaga tgggccgaaa   660
aagtaatagt attagcctct attcggcccg attaatttca ggggaaattt tggtaataaa   720
gtggaaacga cgtcgtgaca aaactactgt gtagactgag aaataaagaa gcccttgatt   780
ttgcccattg cagtcatctc tctcgaatct ctctctataa tccgatctga gaaatttcgc   840
cggagctagg ttttgttgtt taccgatcaa tcctttaatc aatggcaatg ctgttttcc    900
gtcgcgaagg gaggcgtctc ctcccttcaa tcgccgctcg cccaatcgct gctatccgat   960
ctcctctctc ttcggatcc                                               979

<210> SEQ ID NO 72
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 72
acactgcttt ccactcaatc ac                                          22

<210> SEQ ID NO 73
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 73
taggaaattc aacgaaacga gc                                          22

<210> SEQ ID NO 74
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 74
gatctcacgg atccgaagag aga                                         23

<210> SEQ ID NO 75
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 75
tgaagaatca gagaagaacc gg                                          22

<210> SEQ ID NO 76
<211> LENGTH: 665
<212> TYPE: DNA
<213> ORGANISM: Arabidopsis thaliana

<400> SEQUENCE: 76
aagctttact ggaacataca tgtaccttac catcaccctc acttacaacg gtgcaacatt    60
cacgattgat tttttgaaac aagttaccac aaaacttaga ttcaattcga ttcttttctt   120 cttttccaaaa tgttataatt agcttcattc tttaaacgat tcttgtgta aatctttgtt    180 cttttttgaca caacacacaa aattctcaga gcagaatatc agatatagtt cacagcaaca   240
taggtgttgt tcgttctttg ggttgttata tattgcaatc tggatgcagt ttattatgat   300
gtatcagtag agaagagaga aaaagattgt gttggaggga aagagatgaa atatgacacg   360
tggagggcgt cgattggtgg agtatggata gaagcatatc caagttagat ggcttgtgtt   420
ggttcgaaca gatttttttat ccaccacata tttatgtttg atccaaaagc caacacaagc   480
aaagaaatta aaagtgttct tgttgctgta gaacacaaac agaacaaaca aaaaatcaat   540
tgaagagtct ctcagtcgtt aggggaagca aatagagaaa tggctagctt tactgcctcc   600
gcttccaccg tctccgccgc tcgtccggct ctccttctca gcctaccgt cgccatctcg    660 gatcc                                                              665

```
<210> SEQ ID NO 77
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 77
gacaagtaca agctttactg gaac                                            24

<210> SEQ ID NO 78
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 78
acttcttgtt gattcaccac c                                               21

<210> SEQ ID NO 79
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 79
ccaagaacag gatccgagat ggc                                             23

<210> SEQ ID NO 80
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 80
gtggcttatg tccgtcaata g                                               21

<210> SEQ ID NO 81
<211> LENGTH: 2834
<212> TYPE: DNA
<213> ORGANISM: Arabidopsis thaliana

<400> SEQUENCE: 81
ttgaaagtgg gcatttgagt gtgtataaaa aattggtttg gtgagttgaa taatgtaaga      60
atcttttgta tttttctaat taaactgttt atgatcatta ggagaacaat atatggggat     120
gtgttggaat catgaatcgt aggttaaatc ctacaagagg aaaagcttca ggagacagag     180
aagatgaaga gaagagaaga aaggaagaag aagaagaagt cgtgacaaag aaagtcagct     240
aatagacata tctccgctat ttaaagtcga gtctaagcct ttatacactt aaaggttgag     300
ggttcgaacc cttgttatgt cttttttgccc taaaagaaaa aaactttctc atgaaattcc    360
gtgagatgat tcttccattc taagcatttg gttctgttag attgataaag aagtctccta     420
cagtaccaag gcaatgtgcc atccatctac aatttgtata actatatctt ttggtaacat     480
gttcccatca agtgggaatc taattcccct gttattcttt tcacgttcta agcatttttc     540
aagctgttta ccattttgaa acttagtaac gatcaaaaag aataagggat ttcgtcacgt     600
aaattaaata gaatctgtat acaggtcatt taaaaaaata ttttagtaag atacacaggc     660
acagctcaac gtctgatctt ggtttgtcat aaacagcaga gaattctacc acaaggaagc     720
```

-continued

```
tctggtacta tctttctcat taagcatccg cgactacaat attccccaat ttattaaata      780
aacttttcca tgatgcaaaa gtaccttta ttaaacacta cgaataaata aataaaggtg      840
aaacacccat ttcaaagaaa tggtaacgtg tcttttcat taggcgagac tagccaatct      900
aagcaaacag agtcgtcttt atatctaaac gaacatttg tgaagaaag agagactaag      960
gtgaatccat ggcgtccaag attgtctcag ccatagtatt tgtgtttaac ctcattgcct     1020
ttggtttagc cgttgctgct gaacaaagaa gaagcactgt gagtcacatc tccacagcga     1080
tatctaattt gaacaagatg ataattatgt gatctatctt aatattttgg agttaaatat     1140
ttttggtgg ggcaggcaag ggttgtgcag gacactgagg tgcaatataa ctactgtgtg     1200
tatgactcgg acagagctac agggtatgga gttggagcct ttttgttctc agtggctagt     1260
caaatcctta tcatgctcgt tagccgttgc ttctgttgtg gaaagcctct caagcctggc     1320
ggttcacgcg ctcttgccct cattctcttc attgttagct ggtttgttat tataactcaa     1380
ttagtacatc acatatatat ccctagctta agctagctta gacatatctg gcgtttttat     1440
ttcgttcaaa gatgattcaa aactcacaat caaacattta caatagatct tagtttatag     1500
aactagaatt atcattaatc tatcatggta tcaaaatcgc agtaaatctt attatcagct     1560
tacacattt cattctcttt tcaatgcaca gttataatt caaatctaac atgcgtctct     1620
taatccgtta tgaagctaaa cgtgcttatt aaacaaccga cattgtgcta atattttac     1680
aacttgaatg ttgttttgtt ggcgaaaaaa aggatgttct tcttgatagc ggagatatgt     1740
ctattagctg gatcggtaga gaatgcatac cacacaaagt acaggacaat gttcatggac     1800
aatcctcctg attgtcaaac tctacgtaaa ggcgtctttg cagcaggcgc ctcattcgtc     1860
ttcttcaacg ccattgtctc tcagttctac tatttcttct atttctctgc tgctgaggcc     1920
tctcttcac cttactagag gttcttaacc aacaaataag ttttatttt tttctctcta     1980
aatgtgctat ttgatatgct aatatcatat tttgaggtgg gttttctatg tacaactatg     2040
atgaaatgtt acaactatga caaaattatt tgaaagtgat ggtacacatg agatttgtag     2100
atttatttgt atggttatta gatcgagttg aaatgttgtt ttaaaaagag tggatgtaat     2160
ttgacgattt tgtgacatat gacataatgc tcttattcat tgaataaggt ttgagctatt     2220
ctcgtgaatg cgtaaattca aattcgtata atgcatactt tgacagagt aacaattgtt     2280
tattactgga gaaacttatc caaacatgag aacgtccata caactagta gcaagcaact     2340
agctctatct atctccttct cccatgccaa agggtatgga atcccatcaa caccaatcag     2400
caatcaccat ccctttattg caactgttcc atttgttaac ccaaaaaaat agtttaaaga     2460
cattaaaata aaatatctaa ggagaaggaa atctaattct caaattctca ttggatatta     2520
aacgacgacg tggcagatac ttagttcaag ataatgctat ccacacatct tcggtgacct     2580
ctgtggggac caatcttcct ttgtccgaat atctcatttg ctagtacata aacgcacata     2640
ctctctttcg caaaatatcc actacgatag ttttcttcag caatcacact ctctctttgt     2700
tcgagtacca acaatggccc ttcaagctgc ttctttggtc tcctctgctt tctctgttcg     2760
caaagatgcg aagttgaatg cttcttcatc atctttcaag gactcgagtc tttttggtgc     2820
ctccattacc gacc                                                       2834
```

<210> SEQ ID NO 82
<211> LENGTH: 24
<212> TYPE: DNA
<213> ORGANISM: Artificial sequence
<220> FEATURE:

<223> OTHER INFORMATION: Single strand DNA oligonucleotide

<400> SEQUENCE: 82
gttgtttaaa gctttgaaag tggg    24

<210> SEQ ID NO 83
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 83
tattatttct caccagcggt c    21

<210> SEQ ID NO 84
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 84
tcggattgga tccggtcggt aatg    24

<210> SEQ ID NO 85
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 85
ctttaaggaa gtctctgcac g    21

<210> SEQ ID NO 86
<211> LENGTH: 484
<212> TYPE: DNA
<213> ORGANISM: Arabidopsis thaliana

<400> SEQUENCE: 86
aagcttctta ttgaatgata acacacatat gtgatgagaa taaaaagaa aagaatacag    60
aatttatgtg acatatatct tattcacaac catagtattg atccattgat taacatatca    120
aggaaagtaa ttataaagtt aaaggaaaaa aaaaaaaaa aaaagctaa acaaaaaaca    180
aaaaaggaag agacaactaa gcgcgtgtag ttcacaaacc agaagccgag agtcggttaa    240
gaaaccgtct taagctgttc ttggacacgc tgaagcaaat ttaatcgtgt ataaaactat    300
ccttcttcca ccttctcatt atattcattt ccatctttct aatttatctt ccatttccg    360
agccgttgag aattttttct gagagataat ttaacaaatt tcttcttctt cttctgtttc    420
tgaaccacca aatctgcctt tctcaattag ctatgggcgt cgctgttcta aatccccagg    480
attg    484

<210> SEQ ID NO 87
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 87
tcaaatttgt aagcttatct atcgc    25

<210> SEQ ID NO 88
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 88
agtgatatgg tcagcacaga ac                                          22

<210> SEQ ID NO 89
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 89
gaatggatct gtcgaccaat cctg                                        24

<210> SEQ ID NO 90
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 90
aaccagatct gaagtctcct tg                                          22

<210> SEQ ID NO 91
<211> LENGTH: 1840
<212> TYPE: DNA
<213> ORGANISM: Arabidopsis thaliana

<400> SEQUENCE: 91
aagctttcaa gttcatttcc caaagctgtt tttatgatat tttgtcttgt gtattctcag    60
ttctccggtt ccatatttct acccgatata ccttctgata ctattgatat ggagagaacg   120
aagagacgag gttcgatgtg cagagaagta caaggagata tgggcagagt atcttagact   180
tgtcccctgg agaatacttc cttatgttta ttagatgtgc caagagccaa gtcatgaatc   240
ctttcagatt catcctcttg tgtcttattt tttcataatc ttgttttatt ttagcaatgc   300
tcgagtgaaa ctttgtagta cacgtttgag aataacttca gtccttatta ttattttagc   360
attgatatca gcattttcgg attttatttt ttgggttgtt taaaaaccag agattttaca   420
aaagacattt gtttgatgta aaatgtcatg ataaagtaat attgtactta tgtaaaactg   480
agaaaaatac taatagagga acagagtggt gttgataaat gataatgctg atggatatgt   540
ttataggaga aaatggaaaa ttatcacaaa aatagaaatt gacgattacg aagtttctag   600
atgtaccatc ttaatcgact tggagacaat ttaaatggac catacacatc cgtgtttcta   660
tttacatgtc aatatacata tattctttgt ctttttagta tatttccttc ttttcccta    720
ttttcttttt aaatattgta tgttctatat cagtttcttt cttaagatat tatggcatat   780
cgtaacagtt gtttccattt ataatcatat tttattttta gtatgtcata gagttttta   840
aaatttattt atttgtcaac gaggttttat taaaaaatta tatacacata ttaaaaaaat   900
gttgaaaata cgtgtaaaaa tctcataatt tgttataata ataagatgtt tcattttata   960
atcacttgaa cctaaaagat aagaaacaat aaaaccattg aagatcctaa aagacacctt  1020

-continued

```
taaaacttca aaatgtatac aacaacaata gcaacaaaaa agttctagac tacatacata    1080
ctgtgtcggt agaaagcaaa agactttgat agttttgat tattcatgcg tttgaagagt     1140
cgcagctgtt ttccggttat atgtctctat ctaaatctaa gatcttaatt ttctatgttc    1200
ggagatatca aagtcgcact ttttctgtga atctagaaac acataacatt tccaataaga    1260
atattctatt gagattcgta gtcaactatt aagtgtttat tacgattaaa aaactactat    1320
aatcaatgat taatgtaatt tattatctta cgatctcaat tatacaattc gtctgacggt    1380
ttgggccgtc gtaaggccga agtcatgctt ttccttaaat aacactacga gttaccaaat    1440 taccctcag ctaatttgct gagaatccac gctattaagg ggtagaatta agattagcca     1500
acattgccaa ttagagatcc aacggctgaa aaagctattt cttggggaac atgcaaagat    1560 ctgacccta attaatattt tcaccaacca atagactctc atccgcagct ataaaaccaa     1620
cccttttcct ctactggtcc accactcgtc tgccttcttc cgcatctctt ttcatttctc    1680
tctgatttct cgatctctcc gtccaactat gtctgccttc acaagcaaat tcgccggtaa    1740
gatctcgatc tctatctctc ttaagttctt tattcatgtt tagattcgtg tattggattc    1800
gattcgttat cccgtgtttt gattcttatt agcgtgttta                         1840
```

<210> SEQ ID NO 92
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 92
acttatctct tccaaacaac tg                                              22

<210> SEQ ID NO 93
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 93
caccataaga gaacaacaac ag                                              22

<210> SEQ ID NO 94
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 94
actagatcta gtcgactaaa cacgc                                           25

<210> SEQ ID NO 95
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 95
gagtaatttc tcctagaacg g                                               21

<210> SEQ ID NO 96
<211> LENGTH: 1665

```
<212> TYPE: DNA
<213> ORGANISM: Arabidopsis thaliana

<400> SEQUENCE: 96
aagcttatat aaaaaattta aagtttaaaa attataaaat atgtcaacaa tattttagta      60
cttaaaatta ttatgcgaaa tatttagatc aatggactac tcatctaata tatttgcacc     120
taattttaaa gtataaattc aaccaataat tagaaaatga tagcttatac tcaaattcaa     180
caaattatat ataaatgtat agatactaca atatcattaa caaaagtcac cttaaataaa     240
tacacatatc ttttatgttc tctattgttt tgcgtacgct aacacaattt ctcatatgca     300
aaaggatgaa tgagtaacaa attacctcat aagaacaatc atctttgctt acatactaat     360
acaataatca ctcaatcaac caataacatc aatcacatag gtttacatac aataatcact     420
caatcaactt cataagaaga atcatgttta cttaattcat caattatccc caaaaacact     480
actattaagt ataaactata acatatttgt agtgatgggt caacatttttt atcatattta     540
aactcgggtt tcctcaaatc gagaaatagt gaacatgtaa tattaatttt aaatcgcaat     600
tacagaaatt aattgaattt ggtcaaatgg acagaatttt ataaattggg tggaactaga     660
aaaaaaaaaa aaagagtat agggtgaatt gagtacatga aagtacatgg taatcctagt     720
taaacgcata atacatgtgg gttcatttgt attttttttgt aacttacgag taaactggct     780
acaacaaaaa aaaattagaa gatttttttg ttttgtagaa accctaatt ttagttatag     840
ttgtataact ttgataaaat tataaaattg tattacgaaa aaagtaataa gatattcaaa     900
aaagcctaga ataacgtata tgactatgag catgaaactg caagtcaaat gctgacagac     960
aaccataaac aaaagaaatt aaatagagat accttttaaaa taagtaaaat ttcatttata    1020
aaaaatctac tttcttgtga atctgtcacg ttcaataatt tgaagaccac tcaacataca    1080
aggtaaataa tgaaaaataa aatctaccaa aatttcaatt attattatct tccaaaaaaa    1140
caaaattata cagatgatga tggtgatatg gaacttcgat tggctaatat tcactgtgtc    1200
tctaaaaacc atccacttat caagataaga tggaccctac actcatccaa tctaaaccag    1260
tatctcaaga ttcttatcta attacatcat tctctaccgt tagatgaaat tgaccattaa    1320
ccctaccata actccataca ccgcgagata ctggattaac caaatcgaga tcatcgtagc    1380
cgtccgatca acaagtacca tctcttgaaa tactcgaaat cctcataagt ccgtccctct    1440
ttgctctcac tatcaaaact ctgaatttcg atttcaatgg agtcacgcgt gctgttacgc    1500
gccaccgcga atgtcgttgg aattccgaaa ttgagacgac caatcggagc gatccaccgt    1560
caattcagca ctgcatcgtc ttcctcgttc tcggttaaac caatcggagg aatcggagag    1620
ggagcgaatc tgatctccgg tcgtcagctt cgtccaattc ttctt                    1665

<210> SEQ ID NO 97
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 97
cgactaattg aacagctttc tg                                               22

<210> SEQ ID NO 98
<211> LENGTH: 22
<212> TYPE: DNA
<213> ORGANISM: Artificial sequence
<220> FEATURE:
```

<223> OTHER INFORMATION: Single strand DNA oligonucleotide

<400> SEQUENCE: 98
ctaatcttcc atgcactaaa ct                                              22

<210> SEQ ID NO 99
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 99
ccgacgagtc gacaagaaga att                                             23

<210> SEQ ID NO 100
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 100
cataagaatc tgctaaagtg cg                                              22

<210> SEQ ID NO 101
<211> LENGTH: 807
<212> TYPE: DNA
<213> ORGANISM: Arabidopsis thaliana

<400> SEQUENCE: 101
aagcttttag ttttctagat aagatcttag ctttggtcac gtaaaaaaaa ttaaaagtga      60
attggttaac aatataggag tactttgtat ccaaaggtca ttgcaataaa taaacactta     120
agtactctgt agtcacacat ctctaggagc ttaatattgg ataatcgctt gtagacttgt     180
attaaaatat ttagtaggtc aaatccctat cttctacagt ttctactctc gtccgtacag     240
actacagaca ctatgctata gttttgtgtt gaattctaca agtacaaat tcttctttcg      300 gtgccaataa caaataaaca caattctcaa attacatttg tctaaatttt tatttgattc     360
ggtataaatg taacgctatg ttgggaatca tatgataaat ccagattaag acttcttatt     420 taatttatt ttgtatatat aaaatataat atccaaccat aaagtttttt taccgatcga      480
tgataatgtg aatccaaata ttttaacagg atgataaata attgatgtgg cttttataac     540
cgcagcaatt ctggcgtgac tctctccgca gcatttattt ttctctctat aaattaaaaa     600
cattacttac tctttctctc ttccacttaa ctcatatcaa ccttcgccgg aaataatggc     660
tttcccgcga tttcttttctc tcctcgccgt cgtcactctc tctcttttcc tcaccaccac     720
tgatgcttcc tctcgctctc tatccactcc acctaaaacg aacgtactcg acgtcgtttc     780
atctctccag caaacacaaa ctatcct                                         807

<210> SEQ ID NO 102
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 102
aaagttgcac cagtaatcag cc                                              22

<210> SEQ ID NO 103
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 103
cactcaagtt ttgagcatgt g                                            21

<210> SEQ ID NO 104
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 104
aagaaggggg aaggatccgt tct                                          23

<210> SEQ ID NO 105
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 105
tcttgtagct tcctccacaa ct                                           22

<210> SEQ ID NO 106
<211> LENGTH: 3297
<212> TYPE: DNA
<213> ORGANISM: Arabidopsis thaliana

<400> SEQUENCE: 106
gtcgactcca agattcccgg acgttggtcc aagggtatca ctctacaaaa taattataaa    60
aaatgacgag gcatttcatt ttctaatcaa tgtattttct gataaggat gtcatataaa    120 cttggtatct cataaataaa gtatctaaac ttcaaaacga caactacta ttacttgatg    180 aaataacaa cactattata attaatggtt agttgagaaa caatacataa aaaatttgat    240
ggaactatga gagccagcca gttactatcc ttctcacctt ccaatgggtt gcggcaagaa    300
ccttcacaac ctccttata tttgcgatgt gtatctagtc ttttgcaatg gtctcaaaac    360
actttgggtt tcataagttt aactataatg gtgtccctga tattccggt ctaatatctc    420 ttaaaaaga aaatactta tgattcattt caattaatca aggttcaaga agatatataa    480
acactagccc tgacacatga aacttcgatg ccgaaaagct ctaagatcaa agccgaatct    540
ttttaaaaca tacacgtgat ttttgtgtct cccaagacca tcttaaccgg tccatgtttt    600
catgttttag ttagaaatct agattaagtc attaaactaa tccgtatcag taattaccag    660
cttgcatctc agaagtccat tattatttac atatcatcat cacatgctag acacaatcaa    720
taccttatgt caatatctaa aataagtcta taatcattaa tacttgtatt tataccaata    780
gtatatcgtt tattaaatat tattcatact ttatacataa atattccact aggttctgaa    840
cttgtagtac tactattaat aactccgtca aataactact caaaagaacc tctttatctc    900
tctcgtttta tgatctctct cgtctatcat tcaaagaaac aaaaagaatg agaaagaaag    960
taagtagtag tggtgacgaa ggaaacaatg agtacaagaa aggtttgtgg acagtagaag   1020
aagacaaaat cctcatggat tatgtcaaag ctcatggcaa aggtcactgg aatcgtattg   1080

```
ccaaaaagac tggtctcttt cctctctatc tctctctcta atcgtattga cataattat      1140 gaattctttg tcacatgatt ttcttttacg aatggtttaa agttaaggtt ctatatatta     1200
tatatgttat tttagattta acttttaatc tatgttaata gagtccatat atcgcaaaag     1260
caacttgaat caggatattt atctagggtc acctttttgt tgttttatt tttatgaatt      1320 aaggtcctca gttaaataat tgtatatgtg tgttaggttt aaagagatgt ggaaagagtt     1380
gtagattgag gtggatgaat tatctcagcc ctaatgtgaa aagaggcaat ttcaccgagc     1440
aagaagagga tcttatcatt aggctccaca agttgcttgg taataggtat aacttcattt     1500
gctcaaaatt agtttctcta ctcaattaat cataaaaaca gctatttcta tccatttgt     1560 atcaagttaa ataatcataa atattcgtga ttgtcttcac aaacttgctt ggtaacacat     1620 gttttattc tcaaaatttc aatacattat atttcacatg ataattatat tgtttatctg     1680
tgtgtttaat taggtggtct taattgcta aagagtgcc gggtcgaacg ataatcaag        1740 tgaagaacta ttggaacacg catcttagta agaaactcgg aatcaaagat cagaaaacca     1800
aacagagcaa tggtgatatt gtttatcaaa tcaatctccc gaatcctacc gaaacatcag     1860
aagaaacgaa atctcgaat attgtcgata acaataatat cctcggagat gaaattcaag      1920
aagatcatca aggaagtaac tacttgagtt cactttgggt tcatgaggat gagtttgagc     1980
ttagcacact caccaacatg atggacttta tagatggaca ctgttttga tgtgttttct      2040 gcttttgtta ttttagtatt cgtttatgtt ttgttatttt caaagctgat caaacactaa     2100
tacatcaaca gtcttagatt aaagttgtt gatgtggtag tgtatgattg gctaagtcta      2160
ttaattaggt gaactttctt gggttaactc taatgtatat gcttaaaaac tctatatgca     2220
tcgattaatg ttttaaatgt ttcttcaatt tcttcctaag caaaattttg gatttctttt     2280
tgtgaattgt tcatataatc ttattaaatg ttggttcaag atataagcta aaattaaaag     2340
agtcgaacga taacggtagg ttagaaggag tatagtttat ttttattttt attttactttt    2400 gagacgtacg tcccttaatt aatcttcaaa tttgaaaaga agaaatttcc aattaagtgg     2460
atactactac gtaccttttt gtcaactaaa tttcgattgt agttaaaacg atgctaatgt     2520
gtatgtaaac gagaaattag acagaaacct tgattgccct ggcgagttta cttgaaacga     2580
acaaaattaa tactagtcag acaatataat gggtcaaatt gtcacacttc cctaaaaaat     2640
tctataaatt gctatgacaa agctgtcccc cttcttaata gtttaattta tgttctgtgt     2700
ctttggtttt taatatgttc tttgaaagct tgtcccccac tccttccttg attataattg     2760
ctcagacagt tatatacaat gcatgaaact atagtagtat atatattcta attctaaagg     2820
aaggttttcg attatcgaca tggggacatg ttggtcatgt ataagtataa tggaaatgaa     2880
gaggttagta tcaatcttaa tgtatactat agtagccata tctctaatca agacaaacgg     2940
ttttaacatt tttaatatag atagtacaac gcaacattca atgaaaatag caaaataaca     3000
tttccatttc tcaaattttc gtttgacaaa taaataaaat ttatacgatt tgttattct     3060 ctcgtgttgt aaatcaaagc aacttcagca aaacgatatc tgtgaaagta aacatgattt     3120
atttatttat tttataactg gataatgaag gaaagaagc tcatcgcaag taatgtata     3180 ccattacaag tagcaattaa ataagagtaa acatttata tatgaagatg ctgatcatga     3240
tgatgacgac gatgatgatg tttgtgatgg tggtggtagc gatggtgatg gggatcc       3297
```

<210> SEQ ID NO 107
<211> LENGTH: 24
<212> TYPE: DNA
<213> ORGANISM: Artificial sequence

```
<220> FEATURE:
<223> OTHER INFORMATION: Single strand DNA oligonucleotide

<400> SEQUENCE: 107
ggaaatcgtc gactccaaga ttcc                                             24

<210> SEQ ID NO 108
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 108
gtgaatgtgt cactagcaaa cc                                               22

<210> SEQ ID NO 109
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 109
gaactaacgg atccccatca ccat                                             24

<210> SEQ ID NO 110
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 110
tcccaagaga gtcaaagtgt cc                                               22

<210> SEQ ID NO 111
<211> LENGTH: 2183
<212> TYPE: DNA
<213> ORGANISM: Arabidopsis thaliana

<400> SEQUENCE: 111
ggcctggtga atcttctgaa gttattaagg agctgatgca aatggagttg tttagttttt      60
ggatgaaatg ttactctttc gtgtcttcaa aatacatgac tcttcaaacc tttcaagaag     120
ttttagtttt cccctacttg ttttctcaac tcttttatg atatcccaaa tacactgttc      180
tgatttaaca actatcgttt ctgttttaaa cttttgggaa cgttttcatt tgtaaaactt     240
aaacagtgtt cctcatggac acacaaacgc tttcactatg tttgaatccg tattttccat    300
tttctcttaa tcagactcgt ttttattggt tctcgctatg tttcgcggtt ttgtggaatt     360
tttccatgca cgtaattcct cttaagattt tgaccttgtg agagtatgat cacacatcac     420
tatgcatatg tacataacgg cttatcttga ttaccacata ttatatctgc ttaatcctta    480
ttcctcttgc aggtaattta agagcaagct gaacggtcaa cacttacgcc caacaaaaat     540
ctatggggta ccaaatattt gaatgccacc tatctgcttt ttcttttata tatactgaaa    600
agtgaaaagg gatgaatcta tgaattggta gctttataac taagaacga attaagcaaa      660 agttgttttc ttgtttaact tagctaggca tctacctgaa tccaaaagag caacttgttt     720
tgttttgtac taataagtat caacaagtct tgacctgcac atgtcaagtt tttgacttga    780
tttagagcag cttgtttctt gtgtgtccgt ggagttctct actgtttcta tagctttgaa    840
```

```
tgagctttcc atttgaccac atctcaaaaa atttggtaat gtgccttaga ataacaccga    900
gtttggtaac acagctggaa ttggtgtttt gctgtggcat catgggagct ctgaaatgtc    960
ttcccagtta aaggtgagta taactgtttg cattgtgaag atttgtatta actatagaac   1020
attgaattga tggtgttaag ttcttacaca agcgtgcttc tcggtttgaa ctgtttcttt   1080
tgtatgttga atcagagctt agtttatagg aaccagagta tctacttagt cattctctaa   1140
tgctaagtgc taaggttcta cctagttgcc ctctaggccc ttatgttatt gataacttat   1200
gaagctattt gaacacttga ttcttaggag acctaagttg gtacagccag atagagtgta   1260
tgttcttgtt ctctatgtga caggatcaag ctgccacaca tagttcaagg gtatgctctg   1320
tgtgggtttg ctcagattga ggacaaatct atacaaggaa gtagagtctt tgacattttg   1380
atgttgtatg ataagaagaa gaaggagag taataaagaa agagaaaagg gaaacagaaa   1440
cacgtgggag aacatcccaa agaggaagca cacgcggatc ttcatgcaaa gctccccgat   1500
tctcccatgt ggtcccttc tcctttgtc cccctcctct ttcttctttt ctcattttac   1560 tcctttttt accattatac aacgaatctt ttttatcata attttttggt tttggtttat   1620
tttccaataa caccttcttg gttacttccc attctcactt tttcatataa gaaactcact   1680
ttgggaaact tatgtttgag aatgacaagt cttttagag aaagtgatgt aacaaatcta   1740
aagtgattat ataataacct tgcacaatgt ttttgatttt ttgtaagatt cgaatattag   1800
gtttattatt cgtagggaat aaacttactt tcaaaagcgt tcataagtta atactttcat   1860
atatgatcat aagtacggac actattgttt tttgtttgtt tgtgtttatt ctaaaagaaa   1920
gtagctttta attgaaatgt cctcagaggc acagtttaaa gttcgagtgt aacagtttct   1980
aaggcaaaat aagctctctt tctactattt ctctttctct ttctactatt tctctcctgt   2040
ggagaaactc aggagataga gagagagaga gagaagagaa gagagcatgt atgtttggtt   2100
ttataatctc tctactcata ccaaagattt gtctcagacc caccacttgg acagagagaa   2160
cccaagctcc tttctctctt ttt                                           2183
```

<210> SEQ ID NO 112
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 112
cagtactttt taagcttggc ctgg                                            24

<210> SEQ ID NO 113
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 113
ccttgtgtat ttcaagacat gg                                              22

<210> SEQ ID NO 114
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 114
ggagtaggtc gacaaaaaga gaga 24

<210> SEQ ID NO 115
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 115
ataggctctt caatgtttcc tc 22

<210> SEQ ID NO 116
<211> LENGTH: 1358
<212> TYPE: DNA
<213> ORGANISM: Arabidopsis thaliana

<400> SEQUENCE: 116
ggatccacaa gcgaagccat tttgcggctg ctggattctc caaacgttga attcgaagag    60
gagaggatag gagaagagat gaatcgtttt ttgttggttg tctcttacac tttttgagct   120
ccaagtggga gtttatgatt ctctcatcgg taaacgcttc ggaccaagga actaaaaaag   180
aagcgttggt tttgaaggta agtggtgaga gggaaggaca cgtggacgaa tagttacgga   240
agaagggaga gtctacttgt gaggttgagt tttgtcggat gtatatccgc ttgggacaat   300
gagatggact tgctggcct ctgattggct cattgagatt tctattcata ttttcatggt   360
ttgggagtgt ggatattgag tgtcttattt tctttactta tttgacaagt attttatgt    420
tgctctcttg aagatcgtat ttgcggtttc agccatgtaa aagattcttt tccgatgacg   480
acacttttac taggcatatt cgtcgggtag ccggttaat ccggtctaga ttttgtataa    540
tttttggttc agctaggtct ggtttgatat ttttctactt atttcttaaa aactggcttt   600
aatcttttaa ggtaaactca ggattttct ttgaaaacga aatttgaaat atcagactca    660
taacaattgt aacaacaaat gtaaaagtta aaacactcta aaatgtactc aaaattttga   720
tcatcatcat cactattttt tttataataa atggatgtaa aaacttatca tgtttcaata   780
tttaaaactt ttttttttt caatatttaa aacttacata aaatatataa ttaaaagaaa   840
gtttatgaat tagaatatta agttatatgt aattaaatgg agcaatacat gtagcctact   900
agtattgttg ttgcatgagt tgcatcatat tcgaagatat acaatatgtt tttttgatat   960
aagagtaccg cttcattctc ttttttttt ttgtcatttc ccaagtgtaa tattgttatt  1020
aatacatggg ctatactaaa agccccacga aaagtttact gaactatttg aggcccaaca  1080
agagcctatc ggattaacgc ctactgcaga agaaaatctg tctgcactcc acccaagaaa  1140
acgcagacta attaatgaaa tcaacgaaac ggataggtcg ggtctaaggt tgaccatgaa  1200
ccgcaacctg aaccaggagc aaagtggtca agttttgcca tccggtccga gtcccttgga  1260
ggaataatac cagaacagaa aaaaacagaa aagtcgacaa taaacaaaag agacaaattt  1320
gatttgattg gttccagaaa ttcgcagaga aaaagctt                          1358

<210> SEQ ID NO 117
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 117

```
gagacaaaaa gctttttctc tgcg                                              24

<210> SEQ ID NO 118
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 118
tcgcagaagt tgttgtaagt g                                                 21

<210> SEQ ID NO 119
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 119
gtgaatggag gatccacaag cga                                               23

<210> SEQ ID NO 120
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 120
ttacatactg agggaagctc g                                                 21

<210> SEQ ID NO 121
<211> LENGTH: 824
<212> TYPE: DNA
<213> ORGANISM: Arabidopsis thaliana

<400> SEQUENCE: 121
aagatgaagc tcatatacat acataaagat aattatatat gaagatttgt gaaagattct        60
aaaatgatga aatatgattt tgtatgaac ttatgaatag taaccacagc taaattagta        120
agatatgtat attaagcaag aacggcttat cagagttttg ttccaaagct gatcaatcta       180
ctcgtgctta agtgtatatt tgtggtaatg tgttaagagt tcctattaat taccataagt       240
aaatcacaaa cataaataaa atgaaaataa ttatgggctt taaggtctgg aggactactg       300
aaatttggga gaagtagttg gaaaaagaat attagtcgat aggtaggaaa ttgatattgc       360
ttgtggaatg gaggaaaaaa ttgaacgaaa aagaagtttc tagaattcta atcacataac       420
ataaataggg tgaatatttg ggaaaagtaa aacaataggg gtcggtttga tattactaga       480
agataagaaa caaaaggaa aataagaata aggaaaaaa aaagagctct cttttccaac        540
aagaaacgta gagagatata attagagaaa atctgtgctc tttcagatcc cattatcaca       600
aatccatctc tctctctctc tcagagaaga aaccaaagaa gaagaaaaag ctctcaactt       660
tcttcgattt ctcagggaac tctttcgtta atctcaaact caatcatgtc taccccagct       720
gaatcttcag actcgtaagt acccagatct ctgatttgg ttttccgatc gggatttttt        780
tcggatcttc ttaaagtctg ggttttcga ttttggggat tagg                        824

<210> SEQ ID NO 122
<211> LENGTH: 24
<212> TYPE: DNA
<213> ORGANISM: Artificial sequence
```

```
<220> FEATURE:
<223> OTHER INFORMATION: Single strand DNA oligonucleotide

<400> SEQUENCE: 122
ctagcgagat caagcttaag ctca                                         24

<210> SEQ ID NO 123
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 123
gatgagaatg gtatcaccac g                                            21

<210> SEQ ID NO 124
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 124
gatcaaccag gatcctaatc ccca                                         24

<210> SEQ ID NO 125
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 125
gtgtaaaagc ttcgagagac g                                            21

<210> SEQ ID NO 126
<211> LENGTH: 2027
<212> TYPE: DNA
<213> ORGANISM: Arabidopsis thaliana

<400> SEQUENCE: 126
ctacagtact cactcaattt cgttaatctc atagccgagc aaatagctta ccgtttcgtt    60
gatcttgacg ccggctttgg gaacccaggc gaatttgttc tgatgcttcg gtggtccttg   120
ccgtgagccc attttcgatg agctgtgaat ttagatcgga aaaaaacaga ggaagcgatt   180
ttatctggaa gtcgaagaag aggacatgta caagcgagcg gcgcgaaaag aagtcggagc   240
acccaattag gttatgttat ggaatatgtg ttcatgacgg cccaatccat aaactttaaa   300
agcccatcta tttcagctac atttgtgata cttgttgcct tgttgggttt atccttttca   360
aattttggga ggtgtaaatt gttataagta gaaaataata atttaacgtc aatgttccat   420
attgtttaat actgtaaata aagtgtgaga tctacctatc atattttata ggttcacgtt   480
ccatttgtaa tgtttttaaag gtttcttttt ttaaaagacg atgtttagtg aattttcac   540 gatgcatgca atgatcaaac gcaacgtgct tcgacgacct tcccacgacg tataaaatca   600
aagtccaatg attttattg ttattagata acaaaatga atttgttcat ataattgtt     660 ttttagtgaa atttcgtgaa atgcataatc attttcatca tataataaaa taattattaa   720
tagttatcat ccgtggtttc ttttatcatc aatgtactaa tccgtatatt gatgataaaa   780
aaaaaatcgt atagtatatt cataagtgta aggaatgtca aaacttaaaa taagttttga   840
```

```
gattcagctt cccacaatgc cacatgcgaa tgttccttcc atacatagta aagtagatcg    900
aggacagttt ttaatttatt attcccgtta gtaaaaagcc taattacatt ctctaattaa    960
cacctttatt gatgttacac tccggtcaaa aagtattcaa ttattgttcg gttttttgtat   1020 ccccccatct tttaattctc acgaacgact ttttttgttt gttaaaaacg ctcacacacg    1080
aattgaggta cattgatggt aatgtaacta atttaagtaa gaaacaatgg taagcagaaa    1140
tgaattaaat tgctagctga agatctatc cttcgcaagg ttatgtagac cggccaaaaa     1200
aaaagaggtt agctagacct actattctaa actgttcaat ttcctctaag tctaaaactg    1260
attataagta taacaaaaaa aaaaaaacct aaacgaacaa gaaacaaaac tttttaactt    1320
attaaaaagc cttaaatcaa aacaaaattc acaattatat aattaataat aaatgatcaa    1380
aactgaggtt ttgtgatttt tgttggtcag aaatttaata ttgaccacta aaatttgaga    1440
aacaaattta ttttgaatct tttgaccttt taattaacca aaataagtta gtttctaaaa    1500
ttcaaatgtc ttgacaacaa ttttattttt ctgttgacaa caagttataa aaccaaaagt    1560
gtaactgaaa tatataaatc catattagtt cgtaggtata tctgataatt taatttaata    1620
actaaacaag aatatcaaaa agtatggata ttcttcaaaa gtatctgttt aaaaagattg    1680
acaattattt tatttttattt gtggtgataa atatctaaaa tataatctct agacaatatt    1740
ataagcttct attttatgg gaattaatt aacaaatgtt ttctaaacca ataagacaaa      1800
ttattaatag cctagaaaac ggacaattaa gagacaaaat agtaaagtct tcacttcctc    1860
accataacaa ggttaaaaat tcttttgacc tggtgaacga cttataatcc accacgtgtc    1920
aaaactcaca caaagccctc tcacgtgcca actaatataa aagccaaagc gacggtcttc    1980
agagtctccc atcacctccg atctcaaatc tcacaatctt ttctctc                  2027

<210> SEQ ID NO 127
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 127
atcaagggtc gacctacagt actca                                           25

<210> SEQ ID NO 128
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 128
tctcaaactg aacctatgaa ga                                              22

<210> SEQ ID NO 129
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 129
cagagagaag aggatccgga gagaa                                           25

<210> SEQ ID NO 130
<211> LENGTH: 22
```

```
<212> TYPE: DNA
<213> ORGANISM: Artificial sequence
<220> FEATURE:
<223> OTHER INFORMATION: Single strand DNA oligonucleotide

<400> SEQUENCE: 130
caacagagaa tgacaaagaa ga                                              22

<210> SEQ ID NO 131
<211> LENGTH: 3154
<212> TYPE: DNA
<213> ORGANISM: Arabidopsis thaliana

<400> SEQUENCE: 131
aagcttctct ctttatgaca aattttgagc atttaacata gaataaaatg gaaacgcaaa       60
acaaaagagg tatcttaaaa ctgatccaat gaagcagcaa aaaaaaaaaa aaaaaaaagc      120
agaaacagcc gtatacgttt ggagataata cagatattcg aattgtccaa acacaatat       180 atcaaacaag caaaagcaaa cacattgaga tacatacacg taaccaccga aagctctttt     240
tgaaccaagg agagtctatt atgcgaattg gcgcgttgta ccttataaca gatattgggt      300
attgaaggtg aacttccggc ggggatttaa aatctggtgg tggatagcga cggcggacgg      360
cggcggctgc ggccaagcga tgtggaagcg gccgagcgga taagtgagag aaagcggact      420
aaatttagga attaattta ttaaaaataa aaataaaaat caaatgagga ggaggaaaaa       480
caagaaaatg agaggaccga tcatgtccag gtgtcatgat catgttggct aatggctagt      540
ggtggtatca accataacgg catcgttagg taaaaaagga aactaggctc gagtcggtgg      600
gctctagtag cgagagtggt tcgagttggc gatgcttgga gaatttgtta aaaagccgag      660
gcgcttgtag attaaaaatt gttggcccaa taataagtat gggcttttat ataggtgata      720
aatggcccaa ctgtttttt aaaaaggctc gaatcttcct catttgaaat ttctaaggaa       780
tttgattttc caaacttttt gttgaataca tttgaattta aatttgtagg aactttgagg      840
agcaatttgt cttggcaaat tttgttttga aatgtaaatt ttaattgata tatccaaaat      900
ttggtgtcta atctttttat ccatgatgtt atttcaaaac tttaaaaact attgattcat      960
actagtattg atggtattgt acttgtgaat tgttcagaac tcttttgtca aaaaagaaa      1020 aaagagaaca aaatgtttca aaattaaata atccaagaga ggtggaagtg gggactgtaa    1080
cgcaacggga atattgggag tgggcatgca attattgcac tcatgaaaaa taaaactaaa    1140
aatgatttta ctatttggct gaaggtgaca agtgtttggg tggcttggtc ggtttttgta     1200
tacgtaagtt tatgccacgt gtcctcttat ccatggattg gacggcttgg aatcgtggaa    1260
tattttattc tcataccaaa gtccaaatat attacaaccct cccccttttt ttcccttcac    1320
aaaaagctaa aagccattgc ttaaaaaacc aagaaatact aaaaggattt ggaaaagtag    1380
caatcctgat tttgattgat agtactataa tggaacacca gtagttgaaa ttagatacat    1440
aggttgaatg gaattgtaac ataggtttat tttattccct ttttttttg tgaatacatg    1500 acaaaatggt attgaattgt aaatgaactt ttcagaattg tgtgaatggc caaaaaaatt     1560
gcaaaatata aagactatt ctaatatcga cagaattac taatcaagat caaactcata      1620
ccaaaataaa ataggccgt tcaataaata atttcattat ggatgtgagt ttaacttcat      1680
tatggagcat gtacatggtt tgggacacgg gaaaggcgat aacataactt ctgcactata     1740
caccgtttaa agagggaatt taccaggaa atttggtgca tggtcagatc aaatttggtc      1800
catatgagag cttggacggt aataaagaa ggcaagcgat agaacataac gaaatttggt     1860
```

```
aatgggacta gaagaaaaca gcacgtgggt aggacatagt gttacaccca aaaagacaac    1920
aaagcaacga agcaaccata attgtttagt cctttttttc tttcttttgg cttaaacgtt    1980
gtctttcctt tttggcaaat agtggattgc tgccgaatat tacactatcc aatcttcttc    2040
tttaacctca ttaaaaccca ctattcatca tgcatttatt ttacacattc atggtgaaac    2100
tacttggtat atatatgcaa atgaatatgc atgtggatgg tacatggcgt ttgattttgc    2160
atataggcaa tttattgatc aatacttggt gtagttggta cattaaagtt gcattataga    2220
caaacaaaat tcggctgtca tgcttgattg atctatagat gatttcataa taaaaaaata    2280
ttgtcatgga taaaaatagt gaagatgata acaaaaagaa cagaacacaa agaagaatct    2340
catttctttt ttgattaata aaggatata  aagtcattag ttttttttatt cgtctcactc    2400 gacactaata ataactaaaa ttgttggaga attaaaagta agaaagcaat gctataaaat    2460
aaagtaattg ttgggaatgg agcatgtaaa attatcactc ataactaaaa ttagcaatgt    2520
tataaagtat ttaagtaaga aaatgttgta gataatttgt taaatgaggt gtccctatgt    2580
cttttaggtg cggtgagtcc atgtgcttat cctgacagcg gtccaactta accggcggtt    2640
catctcgacc acatattcaa ctgctttttt aatatgattt tctgtatttt cttacctgtc    2700
ataatctaca tttaaacgtt aaaaaatgtc cacaatttta tttattttat tagggtacaa    2760
taacgacatt tgattagagt aaagaaaata gttgcaaagc gggatttgaa actctgtcca    2820
catactttaa ttatcattaa tcaataacaa gcattatcag tattcagcag cagcaaagat    2880
gataacgtta attatactat catgcaatta agttaactaa ttaactatca tcttgtttat    2940
gttttaattt tgtttccatc atcttccaac cttgagtttc ggtcactata aaaagccacc    3000
actctctctg cttctctgca acacataacc cactcacaga aaaacctaga aagctctaga    3060
gagaaagaga gagagagatg gaaggtaaag aagaagatgt tagagtcgga gctaacaagt    3120
ttccggagag gcaaccgatc ggaacttcgg ctca                                3154

<210> SEQ ID NO 132
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 132
catgtaatga agaaccgtgt c                                                21

<210> SEQ ID NO 133
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 133
gtattattac accatcagct cc                                               22

<210> SEQ ID NO 134
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 134
gctctttgtc gaccttgtca ctc                                              23
```

<210> SEQ ID NO 135
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 135
tacgctacct agctaacaca g                                              21

<210> SEQ ID NO 136
<211> LENGTH: 1155
<212> TYPE: DNA
<213> ORGANISM: Arabidopsis thaliana

<400> SEQUENCE: 136
aagcttctgc tttttatcca tgaggatatg aagctgacag taattggtga gtgccatggc    60
cttagatttg catccactac cacaagcaac acaattacca gccttaacgc catcgttgtt   120
gttattatca ttatctccgc taccttcaat ttcatcccca gtttgtcctt caaccttacg   180
tctcttgttt tggtgataat tctcatcttt gaaaggacta acaccatagt tccagctata   240
atatctatgt tgtgccttga gatcctccat tagagcccag taatggtctc tgtagcatct   300
agagagctgc ttcaggttgt gcgatctgcg tcggagaagc tccgggcgag tgaggtgatt   360
ggaatttccc aggatctgat cctccaccgc catcgaaatc ggtgaattcg atgacgtcga   420
cgggttatta gggtttcgaa attgggattc ctccaataca ccggatttcg agggggttga   480
agcaatgatc ggagatggat gcctaggagg tttggaagaa aagggtttt gcttggaagc    540 tgacgccatt gttactgttg aaaacaagg agagagaaa gagagtggcg aagagtggct     600
agaggaaaga caaggacgag acaggaaact ctggcaaaat tgacatttat agaaaggcct   660
tacttaaaag cccaatgggc cataacatga accgaaaacc catgaaaaaa atcgaagtag   720
accgattggt ttaaatcagg ttctgctggt gtgcggctgt cggtggaagg ctccacttca   780
gtaaagtagg gccacaaca cgaaccaggc tgtcttgtct aaccgacaca tacattacac     840
caaacgcaat cttcaccgtt gattgttctc taatccaacg gttgatagag actgctgatc   900
cgtcacccgc tttagtttag tgtttcttct tcctcctctc tttcccaaga atctcttcct   960
tattttctcg gcaacgaagc aaaaagggta attttgtcg gttgaattca caagctagtt    1020
ttctcgatct ctctctggat ctatagctga tctgcattgc gggtaagcat tttttccaca   1080
agtacttatg cctaatttg gtaacgattt agctaaatct tgactagaga atttttgttc     1140
gttgcttggt tattg                                                   1155

<210> SEQ ID NO 137
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 137
gatgatggct gattacagtc ct                                             22

<210> SEQ ID NO 138
<211> LENGTH: 21
<212> TYPE: DNA
<213> ORGANISM: Artificial sequence
<220> FEATURE:

<223> OTHER INFORMATION: Single strand DNA oligonucleotide

<400> SEQUENCE: 138
ctacaagctg caaacatcaa c                                              21

<210> SEQ ID NO 139
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 139
gagatcacgg atccaataac caag                                           24

<210> SEQ ID NO 140
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 140
tgaaagctgg agattgttgt c                                              21

<210> SEQ ID NO 141
<211> LENGTH: 2877
<212> TYPE: DNA
<213> ORGANISM: Arabidopsis thaliana

<400> SEQUENCE: 141
gtcgacagga gccagagatt tattcactta tttgttttcc ttgtattttt agtacacaac      60
atgagaggtc ataaatagac tgagtagacc cattgtgtga gttgatcaac ccctcaatga     120
atacttcttc ccagagaaag cttgaaactt gggctcgtct ttcttctctt gttcctcttt     180 cttttgtctct tttgcagctc caacctgaaa aaaaaaatta agagatgaac aatcatatgc     240
atttgtctct caattccatt acagttttg ttttgtcaat tatcaataaa ctctgaatgc      300
gtactttcgg agcagcttct tttggagcac ggtttccgtt agccccaaat acaagctttc     360
cctgagctcg tgtagctttc tctgagctac ttgctacaga tgactgtcca ttaccattag     420
cgacaacagg ttgtttgcct tttgagctag aggctggcgc tggctcatag caagaggtc      480 tcccatctaa ccgtcttcca gatccggtga aagggttgaa ctttggttca ggttcatcca     540
caacctcctc agctgtgaaa tttggaaaga aagaacaca tgaaatcta acaacttgaa       600 gctgatagta agtccatctg atgatttcat gtccatggat agatacctt tgccggaccc      660 ttagctgcag aaggtgctgt gggacgttca ggctccttgt aatcgagggg aggtgcgaaa    720
tcaacctcac agtctgtttc tatgatgctg attgcgttag caggctttgt ttcaactata     780
tctatgaagt acttcttatt gttgtatgga accataatgc tatccccact agttaggcat     840
gaataatttc tcaaagcagt ctccaagctg caacgttcac tcaattatca gtaaagaata     900
ttgggaacaa gataaaaaga gtgacatcaa acaactacga gccagaaaac gggaagaact     960
tagatataat aatacattct ctaagcaata acaacatga tgtgggaaag tatatgaggg     1020
ctcaaataca agagggtaga aataagtcgg actcacatgg ctttcgggtt ggatatatcc    1080
aggaagtctg ttgtgtgggg ctgtagttta acgtaagttc cctttggaag agtgacattt    1140
ctaactctca caatgtctcc ttcttgcagc agcagattct gcatcatctg gattatatca    1200
aagaagcaaa caatcagtct ggtaagtcca catgatccag agtacttcga ttcacaaaca    1260

-continued

```
aagaggaaac tgattcttac ccaatatggc atgtaaatca tgccttcttc tgcaatgaac    1320
tcaaggactc cacagtgtgt aacacgttca attccagcat tacgaagctc aaacagcatc    1380
ggatagtcaa tatgcaaaga ggctgtaaag tccccaatat tagcgatttg atatgtttct    1440
aagttaaaca aatattagac caaatccaaa agagaaaacc agtaggagca tacctagacg    1500
atcaagggct gatggtggca ttataactga aatagaatta acacaaatta aaacctcagg    1560
cttgaacaat acagatggaa acaaacattg gtgtctagat agaagactta ctcttgtcac    1620
cactttcaag ttgtggctgc agggaagaga aaaggaaata gaaattagat actagatctc    1680
agctttctta tagaacttac ttagtagaac atgacaacga ctaagattct aacattacaa    1740
aagagcactc tcagattcac ttatcaggga attaaactaa aagtagagag atgaaatcaa    1800
accttgtcga taaagatgc cggataacac cggtaactct gctcaaaggt tgttccatga     1860
taatggtatc catcgaaaaa ctgcatcgag tttaaattcc aaaggtttag acaaacaaac    1920
caagggtgcg agatataaaa gctagagtga agactaacgg ttaaaagga aagctttgaa     1980 tacacttacc atagttattg gtggtagtag actaacagag taagttaaca aatggcaacc    2040
tacagaaaaa gaaacctcac acaagtcaat tacaagagat ccaaatcata aagagaaaa    2100 agagggcact ctttaattta agggtttcaa taatcaattg tggccaacaa ttccgaccgg    2160
aaggaacatc aaagttagtg actttaacag ataactaaac aagctattat caaaaaccta   2220
agacctcaat ttcgaatctc agcagaagaa tagaaaccta caaatcgaa gaaccatcta    2280 caacttgcaa aatcccacct tttgaaacaa acccaagtaa gatccttgga aacctattcc   2340
taaacaattc accggaaatc cccagaacag aagattccga tcaaaagttg agagtgggat   2400
cgatacaaac aataccaaag ctaaaaactt tacaaaatta aaagctcgtc ttgagattat    2460
cagagaagaa taagaactca gaaccaccg attgagctgc ccgaccaata aaattacctt    2520
taggaagtaa ttgattccag acacaaccca agtaaagatg caaactttga ggacctgtga   2580
taacgttgct tgtatatata tatacccata cggtgcgtat tgattcatgt ctttgtaaaa    2640
cagtttgggc ttcacaaaaa acggtactag cccattgggc ctcgaatagt gaggaatcat    2700
gaccacttta tattgacgtg tgcgttacca acttaccata ctgggaaact ctcaattctg    2760
agcagatatc tacccaatca cggattgagg agagaagcaa gaagaagaaa tggagattac    2820
actgaacagt ggcttcaaaa tgccgatcat cggcttagga gtttggagaa tggatcc      2877
```

<210> SEQ ID NO 142
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 142
aacaagccgc gtcgacagga gc                                              22

<210> SEQ ID NO 143
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 143
actcactcac atgcaaagaa ac                                              22

<210> SEQ ID NO 144
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 144
gctcttctgg atccattctc caaac                                         25

<210> SEQ ID NO 145
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 145
agagatcaca gatgtgttga gg                                            22

<210> SEQ ID NO 146
<211> LENGTH: 578
<212> TYPE: DNA
<213> ORGANISM: Arabidopsis thaliana

<400> SEQUENCE: 146
aagcttaagc cttgacgaag tcatgaggcg agacgtcttt cacagtttta ccagttgcca    60
tggctcaagt tatcaaaaga ctaatcactg atcttcgtct gggatttgc ccaacgcagc    120 tgaatctctc tccgcaaaga ctagggtttt tattctccaa taacaaaact tatatatacg   180
gccacgatat ttcgattagg gttttctccc catatccggg tcaaaaaatc caacccgttc   240
tcagcccaca ctaatgggcc taattcttca tacggcctta ctatctaacc agtatgaata   300
atgttctttg atacgataat gcgcctacta cggccttatt atatcagttg actagtatta   360
tgtcctaaac gacaccgttc ttaattagta acattaaatg acgtcgtttt ataatcgctt   420
aaccactggc tattagttcg catctcaagt cgtctctgcc attttggct ttttaatcaa    480 accctagaga gattgagaga gcgaagagaa gccatcatca gccatggcga tgaagaatct   540
actgtcccta gctcgccgat ctcagaggcg ttggatcc                           578

<210> SEQ ID NO 147
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 147
cttgagatga gaagcttaag cct                                           23

<210> SEQ ID NO 148
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 148
ctcagtagcg actcgtagac c                                             21

<210> SEQ ID NO 149
<211> LENGTH: 24

<212> TYPE: DNA
<213> ORGANISM: Artificial sequence
<220> FEATURE:
<223> OTHER INFORMATION: Single strand DNA oligonucleotide

<400> SEQUENCE: 149
tggcttgagt gaggatccaa cgcc             24

<210> SEQ ID NO 150
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 150
ggtctcgtga aaaccaaaac a                21

<210> SEQ ID NO 151
<211> LENGTH: 2819
<212> TYPE: DNA
<213> ORGANISM: Arabidopsis thaliana

<400> SEQUENCE: 151
acttgcgtca ctctcatgat ttcatttatt cttgtataat ataaaggtag cggtagtgtg   60
caaatatcaa ataagtagtt taattagtac caatcatttt attcattatt ttttttagta  120
gaatatttgg atgttgaaaa tataaattta attttgtatt tgttgatgtt ataaatttat  180
tgattgtata acattctta gtcatcagtt tcgttaagtc catatctaaa cacttcatat   240 ctgctaaaata gtcaatagat tataaaattg gatcaggaaa aagtaaatcg gagctataaa  300
aaaatagtgt gcaacgaaaa gacaattaat tagttaaaaa tacatacaaa tctaaacaaa  360
ttcaaaattt caatagtgga aaacaccaat caaatggata atgctgtcga agattatcta  420
caaagcatca ataaaagtaa ataattaata ttatcttaca tgctattata aaagattatg  480
agattaggag tataattgtc aagcaactga gcaagagggt aaggtttggt tattatatat  540
gtggagccct atacgaagtt atgtagaaac aaagaaatat caagttgctt caatcatat  600 cctagcaaga caaccctaca agacaagcaa tttgatgaat ttgtctctcc tttttattcg  660
agtgaaagtc attatcttct tatcttttta ctcgaatgtg aatatgcaaa atatcttttg  720
atatttaaga gcttacctag tgagtcatta ctactacgaa aatcatatat caatcttatc  780
ataaactttt aagataaaa aaaaaaaaga aaaaactttt gagagattgg cttttaaaga   840
cttaagttac gattataaac actagtagtt caagtctttt tggttttggt ttgtgttatg  900
ttttagattt aaaatttcaa atgaacctac gtccttaacc aactcaatca aaattctagt  960
taaaaaaaat aatcaccatt tgttagcat tcagcttagg attcgaacca tgggtagctc  1020
aaggtatttt aaactctaga ggaataaaat ggatgttagt gaaatttgtc agcatcatag  1080
acaagatcaa gttggcacaa cttgaagggt cctgacaaaa tatcttaagt tgcctccata  1140
aatgtttaat ggataagact tggccccaca gagttaaacc agagagacac agagagagac  1200
ttttgacacc tcacccatgg ctgcgttaac acatgtttag gattcctttc tttatatagc  1260
caacaatatc atcaaaactt ttcttcaaa caccacttgc agttttcttt attctcctgt  1320
cttgtctaaa gaaaaagag agaggaagaa atggagactt tgaggaaag ctctgatttg   1380 gatgttatac agaaacatct atttgaagac ttgatgatcc ctgatggttt cattgaagat  1440
tttgtctttg atgatactgc ttttgtctcc ggactctggt ctctagaacc ctttaaccca  1500

```
gttccgaaac tggaacctag ttcacctgtt cttgatccag attcctatgt ccaagagatt    1560
ctgcaaatgg aagcagaatc atcatcatca tcatcaacaa caacgtcacc tgaggttgag    1620
actgtctcaa accggaaaaa aacaaagagg tttgaagaaa cgagacatta cagaggcgtg    1680
agaaggaggc catgggggaa atttgcagca gagattcgag atccggcaaa gaaaggatcc    1740
aggatttggt taggcacttt tgagagtgat attgatgctg caagggctta cgactatgca    1800
gcttttaagc tcaggggaag aaaagctgtt ctcaactttc ctttggatgc cggaaagtat    1860
gatgctccgg tcaattcatg ccgaaaaagg aggagaaccg atgtaccaca gcctcaagga    1920
acaacaacaa gtacttcatc atcgtcatca aactaatggg ggaatagtga tgtttaatta    1980
gtatatatag gttaatatct taagtatgtg aagcatcatg tatagagcca agaacctgtt    2040
agactagtgt actgaaaaga actcttgcaa aatatgtact aaagagttcc tgtaacaatg    2100
gaacttctgc gttttctctt gtcttaaaga gcttaaggtt ctagaaacaa agttcttgtc    2160
ctttcggttt attcagagta cactatttgg gaagacaaga ggacctaaat ctatcgacta    2220
catttattta ttaatctact gtgatactta aaatcgaatt tctacctgaa agaccttaac    2280
ataagcctta aagtttctcc aatgacacaa acagtaccgt acagtggctt cagtattcac    2340
tattcgatat cactgaggta ttaattagtt cacatgtcca gaaagcgtga atcagtgaat    2400
tgagtagaaa gatgaacaag ttgcaagagg gaccaagttt aaagaatata gcagccagag    2460
ttttgtctca tggttgggta caagtcagca ttcatttttt aaatatgaca agaattgga    2520 tggaccacac gcaacagctc aagaggggag agatgcacaa gttgcaatat ggaaaagtaa    2580
acagaggaag atatgtatta acatctcaac ctcatcgttg agatggatgt tgattattat    2640
tattaggaat aactaaaacc aaagaattct tataagttat aacaatgaaa ttacttcatg    2700 gtttttgat aaagatatct cctatgcata tatatctagt atacatttgg aacagttgat    2760
gaatatcaac tgacctgttt cttagataga agagatcttc atgttatcga tctttctt    2819
```

<210> SEQ ID NO 152
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 152
atcgacatgg aagcttaaga aaag                                            24

<210> SEQ ID NO 153
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 153
ggtgacggaa gtgacaaata c                                               21

<210> SEQ ID NO 154
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 154
gtacgatgac ggatccactt gcg                                             23

<210> SEQ ID NO 155
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 155
gggttaaagt ggaggaagaa g                                              21

<210> SEQ ID NO 156
<211> LENGTH: 1313
<212> TYPE: DNA
<213> ORGANISM: Arabidopsis thaliana

<400> SEQUENCE: 156
ttgtatgacg cctttattc atattcttgt tatctccgtt atgtcatgtg tgtgaatcac      60
ttatataatt ttcgtaagat tttctgaata tgttggagtc tttgctaact gtttgaatcg     120
agatcagtta acacttatta agaacaaaaa tgtggtttct tgtgagaaaa atggtttaat     180
aaaaatccgt gattgataga agaaaaagat caaaataaat ggttggtgac gggtgatctt     240
aaaaatgttg aaattaaggt gtgtcgtcgt tatacgcggt aaatagatag atagaaaaat     300
agaagtccaa tgcaagagac ttaacttaat catcccaatt aattgattgc attaacttgt     360
acttgtattt tccgtccgcc acctaatttg attaataata taataaagat tacaattgaa     420
aacataaaca agagaaaatc cgcacgaatc taccaaagtg catcacgttt gggtatccat     480
acacgtgacc accagtccac cacaacacaa tgtctgtaga tattttaatg tttcacatga     540
tagaagaagc caaacgtaag aactctcttt tccacttta gcccttccc cgcctaccac      600 tgcttacgac ttgtgtaagt ggcaaactag taataataga gacgaaactt aaatataaaa     660
aagttgaatc caaccaagtt ggtgttaatc aaatggttaa gttataatgg tgaaagattt     720
gccatgtgta ttgtattaag agttaagacc aaggtttggt tcccatcact tacgattctt     780
tcttttcata tgattctaaa gttagttatt ataaacatct taatttacta cacaatattc     840
ggtaatttct acatatttta gagattagtt tgagtttcaa tccatacttt actagtgatt     900
ataaattaat atacgtactt ttcgactata agtgaaact aagtaaatta gaacgtgata      960
ttaaaaagtt aatgttcact gttatatttt tttcacaagt aaaaaatggg ttatttgcgg    1020
taaataaaaa taccagatat tttgaattga ttaaaaaggt tgaaataaga gaggagggga    1080
aagaaaagaa ggtgggggcc cagtatgaaa gggaaaggtg tcatcaaatc atctctctct    1140
ctctctctct accttcgacc cacgggccgt gtccatttaa agcccgtct cttgccattc     1200 cccatctgac caccagaaga agagccacac actcacaaat taaaagaga gagagagaga    1260 gagagacaga gagagagaga gattctgcgg aggagcttct tcttcgtagg gtg          1313

<210> SEQ ID NO 157
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 157
cagtggttaa gcttgtatga cgc                                            23

<210> SEQ ID NO 158

```
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 158
gcaacatatc gttttgtaga cg                                              22

<210> SEQ ID NO 159
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 159
cgttaataac gtcgaccacc ctac                                            24

<210> SEQ ID NO 160
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 160
gtgatagatg tcactttgct c                                               21

<210> SEQ ID NO 161
<211> LENGTH: 2080
<212> TYPE: DNA
<213> ORGANISM: Arabidopsis thaliana

<400> SEQUENCE: 161
catcgttcct tgctggcttc ttctctcgaa gtcacgatgg ctcttatttt tttattattt       60
aagtaatagt ttacttattg aattattttt ggttaattta agaggtatat taataaatgt      120
gggacctaca aattccaatt ctatcggttc tttagtgact gagacgtcgc tatatgtgaa      180
aaggatattt tagttgtcac agaattgcgt ctatttctta ttttttcatc tttttgcaat      240
ttgccgattc tacgagaaca tcatttgttt attggatatg cttttttttaa agaatcaaga    300 gaatacgaaa acaacttgta ctcaagaatg tttactataa ttctctagtg gatctttata     360
agagctggag attagtttgg attttatctt aaagtatcca gttatcaaaa aatgagattg     420
ttaggacttt ttttacccga gagtatttag ttacaaaaaa gaaagttagt ttaatattag     480
ataaactata attgcaacta acggtcagta gaaagctata taagttatat aacgaatctg     540
aatatgactt agttatcttg ttggattgtc tagatatgtt tttgcctttt acggaaagat     600
tcgatttgga caaacttctg aattaacctg aaaaacgtaa ttaaacattg acttgttggt    660
tgtttgtaga atggttggtt tatactttcc gaatgtggct atgtgaaatc acattttgat    720
tatatgtata aagttgagat ataatttttaa aatttgcaaa aaattattag ttttgttaaa    780
ataataggag atgcaaacta aataaattct cttcttaact aaaaaagcaa tagatttgtt     840
acattgaatg atggatagat ttgtgagttg tgactttgct taagctaccc caacagataa     900
cggatatatc atatagatgt tgagtaagaa agaaaaaaaa acatttacga ttgcattctc     960
gtaatgggct ttatgatttt aaggcccaat agatgaagta aggctaatgc acaactttaa    1020
gaaacgtaat tctagcaagt gtttatcgac tgcgttgtag gttcttgtg ttcgtggcac     1080 tatggattag gttttaatat ggtttctaat ttcgttgatt tcagtggcat aagtccagtt    1140
```

```
gttgcttgtg gcaaactgtt tcatgtacaa aaacacttac atcattacta aattatgtca   1200
tgggtttggt ttcgttaaca ataagtcaat ctccttgatg agttttatct atatgattat   1260
ctatttgtct atttgcaaca tgtagtagat tgaaatgggg ctgcaaaata tgctcttgca   1320
attcctagtt agatctagct tttgataata cgattatcta atttgtcatt tcgatatgat   1380
agatagattg tttttaaaag agatctcaac cacttttctt taactaaaat aaaaaattta   1440 gtcactttt attaaaaata actaaaaagt tttaaaccta tcaggacact tccatcaaca    1500
gtatttaaaa gagatattta ttattaaaat aatacaaagt ggtgaaaaga agagagaagt   1560
gagaatcgtc tctgttttca gaaactctga aaaatgttta tggccacgtg ttttccaga    1620 aatgattgat tttattcttt ttattaaaat ttaatacttt atctaaattc aattaaaata   1680
agcaatattt tattcatgag aaactctttt ttgagaatca accgatgtag atggtctcat   1740
actctacttt gttgattgtg tttaagtttc tgaggatttt tctactttcc gacgttatgc   1800
caagaggctg gtcttcacta gaaaactact tccacccaat tcaagcaagt atgacctctt   1860
ctcccaacaa tttattcatg tactgaaagg ccattagaag ttgactgaag tgtgaaggtg   1920
gagattatgt attcacttgt tgatttggta tacattctat gtaaggttca attatttacg   1980
ttatataatt ataatggagt aatttacagt aattgggtta aaatggtttg attcggtcag   2040
gttgatacgg tttggaagtt aaacccggcc tagatatgat                         2080

<210> SEQ ID NO 162
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 162
tgatgccgta ataagcttca tcg                                           23

<210> SEQ ID NO 163
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 163
gacaatgaac cagtactatg c                                             21

<210> SEQ ID NO 164
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 164
gactggttgt cgacatcata tctag                                         25

<210> SEQ ID NO 165
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 165
```

```
cgtggagaaa gattaaaagg tg                                              22

<210> SEQ ID NO 166
<211> LENGTH: 174
<212> TYPE: DNA
<213> ORGANISM: Arabidopsis thaliana

<400> SEQUENCE: 166
aagctttgtc atttctgaat accgcaaagt cttacgggtt agtttattca tttacaagct     60
atttcatcac gtatggctta ttcaaacgaa aaggaacaat agctttatat aaaaaaaaat   120
ggtcctaata tgaaatatct cactatctcc tctaaatttc atcaatacgt cgac         174

<210> SEQ ID NO 167
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 167
tgactacgta agctttgtca tttc                                            24

<210> SEQ ID NO 168
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 168
atcgacatgg aagcttaaga aaa                                             23

<210> SEQ ID NO 169
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 169
gtaactagta atgtcgacgt attg                                            24

<210> SEQ ID NO 170
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 170
ggtgacggaa gtgacaaata c                                               21

<210> SEQ ID NO 171
<211> LENGTH: 2096
<212> TYPE: DNA
<213> ORGANISM: Arabidopsis thaliana

<400> SEQUENCE: 171
aagcttaaga aatcaacaat attaacctgt aactataaga atgtttagtg aagagactaa     60
ctcgcaagca gaggaccaaa taccaacttc aaatctctca agacaaaact tcataaactc   120
ttcagcaaac ggtctcttat acactaaaca acaaacaaa cacaaataaa ctataaatac    180
aaaaaaggta gcaaagttaa taaaagaata atgaaacgtt accaagattt ggcccacaag   240
```

```
aagcatcagg agagcggttc ttgggtttct tacgcaactc ttttttgtgg actctgtgaa     300
gaagaagacc acttagactc aagaccaaga gtttctttt ctccgtctta ggttctagac     360
taagtttatc aagaatcgaa ctcagttctg tctgatctga aactgtatca cctcttgagt     420
actcatcgtc gctgtcgtcc gcagcaagca agctcttctt gatcttttct tcagccattg     480
tattgaatga gattgatcaa actcatatgg tgcatatata tatatactag gtgagtcatt     540
taaggtggtg actaatggcg atttggcttc acgagatcaa aaccatttat ttggcgtttt     600
tcttcaagcg gctctttgga tactcacaaa tcttttttgt acttatcctt aatttctctc     660
tttttttttt tttttttttt ttttcctgta tccaacttgg tagtgtgaat cgacttacag     720
cgaccaatca gaaaattcca cctgtcagca gttgttatac atggacaaaa gtcgatacat     780
caattaatcg acgctgattt gtcgagttat atttcccgtt taccattttg ttttcttgtt     840
atgatttggg gaatctctca cgaattctat caaaagaaat agcactaaag gctcggagga     900
agcctgatga acatggaag attgtgctct attttcttct gacaattttt acataagtaa     960
aacgcatttg tttactattt ttttcatata aaacatgaaa aacttatatt tgaattaatc    1020
gaaattaaaa ttattaacag aaatatctaa gtttatatga accttttaac aaaaaaaaaa    1080
gtttataaga acataaaaat cataatagtt tagcaacatt taaattattt tcaaaaatta    1140
gtaacttaga ttaaaataaa tattagatca cctcataatc ttgagtttga aactccaaag    1200
tccaaagagc atccaaaaat ccgacgcaaa caccacattt tgataagaat tatagaacta    1260
gtgatttgca ttttaaatgt tgatacatat agaataagca taatcaaaca atgattactg    1320
aaaaatatgg tccattaata tcgtataaaa atggttgatg acattgaaa ccctagtgga    1380 gaatttgtca cataagtaag gcccaaagtt tttgacccac aaacatatcc attaagttat    1440
agtttagcga accccttta acaaaaaaga aaattttcaa ctagtgaatt gtttctagag    1500
agttctgtac aaccatccaa atttcaaaca tggtataaaa gatgttattg acaaaataaa    1560
aatggaaaca gtgaaacgta gtcggaaa atggaataaa atctagatgc catatattat    1620
tcttacttgt tctaaagtct ttaataaaaa tagtcggtat tacttggaca aggagcaaaa    1680
caatatggaa aaaactcttc tattctgcaa aaggcgtgca gcgcatcgtt ttggcttctt    1740
gcatcagagc tgactgttct catccaacgg ctgttattaa aacaatccaa cggttttggc    1800
taaatccgtg acgtctttat atatcgaacc agaccaccaa cccatttcct cagctactac    1860
tgttgaagcg attctcacta aaaccctcga acacatcgcc tttatctctt tctctagatc    1920
tactcgctat ggctactatc accgttgtta aggctagaca gatcttcgac agtcgtggta    1980
atcccaccgt tgaggttagt ttctccgatc acttttgtat ttcccagtca ctttccggct    2040
ttgtacagta ttcgtgacgg atctgtttgt ttgatgacta tccgatgcta aaacca        2096
```

<210> SEQ ID NO 172
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 172
ttggatcacc tagcttcatc a                                              21

<210> SEQ ID NO 173
<211> LENGTH: 21
<212> TYPE: DNA

```
<213> ORGANISM: Artificial sequence
<220> FEATURE:
<223> OTHER INFORMATION: Single strand DNA oligonucleotide

<400> SEQUENCE: 173
cagctgctgt aaccttaata c                                                    21

<210> SEQ ID NO 174
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 174
tagccttgtc gacggtgata gtag                                                 24

<210> SEQ ID NO 175
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 175
ctatttctcg tttaccagtt gt                                                   22

<210> SEQ ID NO 176
<211> LENGTH: 1617
<212> TYPE: DNA
<213> ORGANISM: Arabidopsis thaliana

<400> SEQUENCE: 176
gtgtcgtgct atgtgtgtgt gctcgtttct tttgtctttg agcttaaaag ttaaaactct          60
agtctatatg gacctgaata aaaatatttc caccaccttg aggttttggt gtttgcggtt         120
atggacggtt tattgaatgt aatattttcg taccaaatcg gtttactaga tttgagacgg         180
atcatatggc tcttcttgga aaagagacg gtttaaatcg gtttatcttt agctctgctt          240
tttttcttcc cggaatttgc ggaccaattt tgattgtgtt ggttcagata tagaaaccta         300
gtatattgta gcaattactc tccaaaaata gcattagatc catccaagac aattggagaa         360
acagagagga gagaaagaga acttgtgttt atatacgttt atcaaaacta aatttatgtt         420
ggttaatagt tataccatga tggagtaaaa tcagatattg tatacaatag ctttagtatt         480
caatctaact actataagtc tacatcttca atacatgtag tcacatgaaa actcagccac         540
aaccgcaaat aaaagggaga tcaaattagt tggctgtatt aatggtaatg gatccaccta         600
ctttacacta caactatatc attggaaagc catttataat atacattcca tatagctaga         660
gccatatcca ctacgtaacc gaatctaaaa tttctaaacc cttctctttc tttctgcatg         720
ctgattaaaa ccgacgctgc agaagttcga tcagttatat gagtgcatta aatagaatcg         780
attttagaaa aagaagaaga aagaatcgat ttaacttaaa gtcaagctgt ttgcttaggc         840
tagaccggat ctgatcttca tgtataggtc tcaaggatca tgcgatcgat gtatataaat         900
atgttttggg gttgggacca aattaaagta gtatatagtg gtatttctct tggctcccca         960
attaatttta tcggttgggt tgtctgtctt tttatgctca tttacctaac tatcacggca        1020
tctccatagg aattaatact tttgtgtaac tatatatgtg taagtgtcta tactgaatat        1080
aatccggtaa tatgtgaata tatgcacgtg aatttaattt aaatatatgt gtcccgcctc        1140
ttgcaaaaat agttatgata ataagatgac taaaatttaa gaatgtataa aaccaacaaa        1200
```

```
aatatgttta agaatgtaag ttttgtgtat cacatcccat gttttaaggt tgttaggaat   1260
ctcacatgca cattgaaaag agactaacac taattaatgt acgagagttg attgatgcta   1320
tgtttaatct ctttgtatac aaatacatat cgtttgacat agaaatacaa atacatatcg   1380
tttgacattg tactctttga aaagagacta acactaatat gttagtaaga ctaatttata   1440
tttagctaca ttgtactcaa ggtcctatat ccaaagtttt atctgcattt attgcacact   1500
tacattacgt atgtgtgtgt atacataaca gcctatatat atggtcttgt aacacagctc   1560
agggattcac cataaacaaa aagaatttga accaacaaag caaaacatga aaggcac      1617

<210> SEQ ID NO 177
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 177
agatgtggtt aagcttgtgt cgtg                                           24

<210> SEQ ID NO 178
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 178
ctagtagcaa gacctttttg g                                              21

<210> SEQ ID NO 179
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 179
acaagcaagt tagtcgacgt gcctt                                          25

<210> SEQ ID NO 180
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 180
aggaaagatc actagagaag c                                              21

<210> SEQ ID NO 181
<211> LENGTH: 428
<212> TYPE: DNA
<213> ORGANISM: Arabidopsis thaliana

<400> SEQUENCE: 181
ggatcctagc cacacgcact aatctcgcca ttgcagaaag agaaatgtag agagatagaa     60
gcggcttgag ctttgagctt accctaaaca agaacgtgca cgaacatatg ctctttagat    120
tcttttccca ttttgcccta agttaactg acgtggcatg tgacttttc tctgagatca     180 tggttacatc atctgacacg tgtaataacc caactccacg agattaacca acggtatgag    240
```

-continued

```
aaaatcgatt tcgatttaa attgggatta ttattatttt cagctttctc tggaagcaac      300
aatggcgatt gctctctcgt cgtcgtcgac gatcacgtcc attactctgc agccgaagct      360
gaagacgatt catggattag ggacagtact tcctggttat tcggtcaaat ctcactttcg      420
taggatcc                                                                428
```

<210> SEQ ID NO 182
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 182

```
ccggagaggg atcctacgaa agt                                               23
```

<210> SEQ ID NO 183
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 183

```
gtacgatgac ggatccactt gcg                                               23
```

<210> SEQ ID NO 184
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 184

```
gggaggagga tccagccac                                                    19
```

<210> SEQ ID NO 185
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 185

```
gggttaaagt ggaggaagaa g                                                 21
```

<210> SEQ ID NO 186
<211> LENGTH: 1022
<212> TYPE: DNA
<213> ORGANISM: Arabidopsis thaliana

<400> SEQUENCE: 186

```
catcttcact gacaaaacac ggttctgtgt ggttttcgct gaatgatcca ttctactact       60
gcttggtttt cttctgtaat tcaatacaag gacaaccatt actcaatctg acatagtatt      120
ccaaggaaaa agagagagca taacatgtag atccaatcga aaacgaagat ggtgtcgaag      180
aatctaacta catttctatt gtaaatccat taattaaaaa ctgcattttt tagacaagga      240
aaccctcaaa atcacactgc aaacgagaag aatatatttc gaaacaaaaa gaaacccaga      300
aacatgagag aacaatacga cggtaccttt tttttctcag cggatggatc gaagaaatgg      360
gtctctctat actctctcgg acggagaaaa agaaaggaat agaaaagtga attcaaagaa      420
gaagcgtgaa tgagaagcag agtgagagaa tcattgatct gcgtgcgtga cgataatggg      480
```

-continued

```
aggcaatgat gctttagttt attttttgaaa atcaaatttc aaaaatcaaa aagacaaaca    540
tcggagagcc catccatgga gattagggtt tattctatct ccgaaatgac gattaagccc    600
ctacacaacc ctaaccacga aagcccaaag cccattaata actaatttag aaagcccagt    660
cttcttcttg ctaaaaatta ataatggaaa aaagacaggg cagcgcagcg atgattaagg    720
tgacacggtg ggctcccacc accgccagct ggactcgccg acggtgaact gtctctctct    780
accacacatc actccttcct tctgtccttt cttttttgta tttattatta ttattcattt    840
taaaatcaaa aacccttaaa ttattaaata aaataaaata aaaggcaata atggaaactt    900
tccttcttct tcacaattct tcgcggcttc ttttagcttc taagcttcag agcagcaaaa    960
aaaaaacaat ggagaagcgc cggagataga tctgctttct tccattctcc ggaccttctc   1020
ta                                                                  1022
```

<210> SEQ ID NO 187
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 187
gttggttcgt cgactagaga agg                                            23

<210> SEQ ID NO 188
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 188
gcaatgaaga tgatgatgtg c                                              21

<210> SEQ ID NO 189
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 189
cttactcggg atccacatct tcac                                           24

<210> SEQ ID NO 190
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 190
aactcctgtt gctaaaacgg a                                              21

<210> SEQ ID NO 191
<211> LENGTH: 1056
<212> TYPE: DNA
<213> ORGANISM: Arabidopsis thaliana

<400> SEQUENCE: 191
aagcttagac cagaccgaaa ggtttactgg gtcaatttgg tgcctacaca tccacttggc     60

```
cacctgttgt gcaatgatga cgatgagatt gcagtgtctc tcgactgatg atgtagactt          120
cacaatctct taaaaatccc agtacttaac ctcagcctta agaaaacgca gggaactacg          180
tcctcacaaa atctttctct ttgagtgtaa ctttcagacg catctttggc tctaaattct          240
aaaaaggaaa atttaatag gttttcataa tcatgggttc actggattag catataagtc           300
tatggttgag aaacttgaga cccagactaa cgaaacctct ttccggatcc aaaggtcctc          360
ttgtgtagtt gacgtggtaa actctctacc gtcaaattta gacattagct aatctgatca          420
ataatctcgg cagctcttaa aaattaaaaa ttagaaatga tacgaacctc ataattttc           480 tttctcttat caaaacacca tctttgtatc tttataagcc tgttgccact attttttaatt         540 gaaaatgatg cgtttgtctt atgttttctg tcctggagtt caacattatg acaatatgta         600
tagtaaatta gtgatataca agacgtttgc aattcaagaa aaaaacttat aaactaatta         660
atattatggt ccacggtgct acatattaac tcttgatggt tttatacatc ttttctacat        720
gctaatatgc ttttaatatt gtagcctaac gttataattt gttttttctt aaagaaacag       780
tatcttgaac gaatcttaac tatttctgta cttattcgat tttattcgat ttttatccgt         840
gtaaaggcaa acgattatta tgtaacgacg ggcataaaaa gagtatcgat ttcctattcg         900
gagaaaaaaa aaaagataaa aattggagtg tatgtatatt tcttgaattg agagtaatac         960
aagattacgg tccaggtggc ggaatattat tggcaaggtc acaagaacct caaataactg        1020
atctgaagag aaatataaat ccaaaagagg gtcgac                                  1056

<210> SEQ ID NO 192
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 192
cccttatctc tcagtcgacc ctc                                                  23

<210> SEQ ID NO 193
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 193
gaagagagga tatgtgtgaa g                                                    21

<210> SEQ ID NO 194
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 194
ttcaaaataa gcttctagac caga                                                 24

<210> SEQ ID NO 195
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 195
```

```
aagagatttt caaagtgtgg                                             20

<210> SEQ ID NO 196
<211> LENGTH: 2027
<212> TYPE: DNA
<213> ORGANISM: Arabidopsis thaliana

<400> SEQUENCE: 196
gagagaaaag attgtgagat tgagatcgg aggtgatggg agactctgaa gaccgtcgct     60
ttggctttta tattagttgg cacgtgagag ggctttgtgt gagttttgac acgtggtgga    120
ttataagtcg ttcaccaggt caaaagaatt tttaaccttg ttatggtgag aagtgaaga    180 ctttactatt ttgtctctta attgtccgtt ttctaggcta ttaataattt gtcttattgg    240
tttagaaaac atttgttaat taatttccca taaaaataga agcttataat attgtctaga    300 gattatatt tagatattta tcaccacaaa taaaataaaa taattgtcaa tcttttaaa     360 cagatacttt tgaagaatat ccatactttt tgatattctt gtttagttat taaattaaat    420
tatcagatat acctacgaac taatatggat ttatatattt cagttacact tttggttta    480 taacttgttg tcaacagaaa aataaaattg ttgtcaagac atttgaattt tagaaactaa    540
cttattttgg ttaattaaaa ggtcaaaaga ttcaaaataa atttgtttct caaattttag    600
tggtcaatat taaatttctg accaacaaaa atcacaaaac ctcagttttg atcatttatt    660
attaattata taattgtgaa ttttgttttg atttaaggct ttttaataag ttaaaaagtt    720
ttgtttcttg ttcgtttagg ttttttttt tttgttatac ttataatcag ttttagactt    780
agaggaaatt gaacagttta gaatagtagg tctagctaac ctctttttt ttggccggtc    840 tacataaccct tgcgaaggat agatctttca gctagcaatt taattcattt ctgcttacca    900
ttgtttctta cttaaattag ttacattacc atcaatgtac ctcaattcgt gtgtgagcgt    960
ttttaacaaa caaaaaaagt cgttcgtgag aattaaaaga tgggggggata caaaaaccga   1020 acaataattg aatactttt gaccggagtg taacatcaat aaaggtgtta attagagaat   1080
gtaattaggc ttttttactaa cgggaataat aaattaaaaa ctgtcctcga tctactttac   1140
tatgtatgga aggaacattc gcatgtggca ttgtgggaag ctgaatctca aaacttattt   1200
taagttttga cattccttac acttatgaat atactatacg atttttttttt tatcatcaat   1260 atacggatta gtacattgat gataaaagaa accacggatg ataactatta ataattattt   1320
tattatatga tgaaaatgat tatgcattttc acgaaatttc actaaaaaac aattattatg   1380
aacaaattca ttttgtttat ctaataacaa taaaaatcat tggactttga ttttatacgt   1440
cgtgggaagg tcgtcgaagc acgttgcgtt tgatcattgc atgcatcgtg aaaattccac   1500
taaacatcgt cttttaaaaa aagaaacctt taaaacatta caaatggaac gtgaacctat   1560
aaaatatgat aggtagatct cacactttat ttacagtatt aaacaatatg gaacattgac   1620
gttaaattat tattttctac ttataacaat ttacacctcc caaaatttgg aaaggataaa   1680
cccaacaagg caacaagtat cacaaatgta gctgaaatag atgggctttt aaagtttatg   1740
gattgggccg tcatgaacac atattccata acataaccta attgggtgct ccgacttctt   1800
ttcgcgccgc tcgcttgtac atgtcctctt cttcgacttc cagataaaat cgcttcctct   1860 gttttttttcc gatctaaatt cacagctcat cgaaaatggg ctcacggcaa ggaccaccga   1920
agcatcagaa caaattcgcc tgggttccca agccggcgt caagatcaac gaaacggtaa   1980
gctatttgct cggctatgag attaacgaaa ttgagtgagt actgtag               2027
```

```
<210> SEQ ID NO 197
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 197
atcaagggtc gacctacagt act                                            23

<210> SEQ ID NO 198
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 198
tctcaaactg aacctatgaa ga                                             22

<210> SEQ ID NO 199
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 199
cagagagaag aggatccgga g                                              21

<210> SEQ ID NO 200
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 200
caacagagaa tgacaaagaa ga                                             22

<210> SEQ ID NO 201
<211> LENGTH: 2819
<212> TYPE: DNA
<213> ORGANISM: Arabidopsis thaliana

<400> SEQUENCE: 201
aagaaaagat cgataacatg aagatctctt ctatctaaga aacaggtcag ttgatattca    60
tcaactgttc caaatgtata ctagatatat atgcatagga gatatcttta tcaaaaaacc   120
atgaagtaat tcattgtta taacttataa gaattctttg gttttagtta ttcctaataa    180
taataatcaa catccatctc aacgatgagg ttgagatgtt aatacatatc ttcctctgtt   240
tacttttcca tattgcaact tgtgcatctc tcccctcttg agctgttgcg tgtggtccat   300
ccaattcttt gtcatattta aaaaatgaat gctgacttgt acccaaccat gagacaaaac   360
tctggctgct atattcttta aacttggtcc ctccttgcaac ttgttcatct ttctactcaa   420
ttcactgatt cacgctttct ggacatgtga actaattaat acctcagtga tatcgaatag   480
tgaatactga agccactgta cggtactgtt tgtgtcattg gagaaacttt aaggcttatg   540
ttaaggtctt tcaggtagaa attcgatttt aagtatcaca gtagattaat aaataaatgt   600
agtcgataga tttaggtcct cttgtcttcc caaatagtgt actctgaata aaccgaaagg   660
acaagaactt tgtttctaga accttaagct ctttaagaca agagaaaacg cagaagttcc   720
```

```
attgttacag gaactcttta gtacatattt tgcaagagtt cttttcagta cactagtcta    780
acaggttctt ggctctatac atgatgcttc acatacttaa gatattaacc tatatatact    840
aattaaacat cactattccc ccattagttt gatgacgatg atgaagtact tgttgttgtt    900
ccttgaggct gtggtacatc ggttctcctc ctttttcggc atgaattgac cggagcatca    960
tactttccgg catccaaagg aaagttgaga acagcttttc ttcccctgag cttaaaagct   1020
gcatagtcgt aagcccttgc agcatcaata tcactctcaa aagtgcctaa ccaaatcctg   1080
gatccttttct ttgccggatc tcgaatctct gctgcaaatt tcccccatgg cctccttctc   1140
acgcctctgt aatgtctcgt ttcttcaaac ctctttgttt ttttccggtt tgagacagtc   1200
tcaacctcag gtgacgttgt tgttgatgat gatgatgatg attctgcttc catttgcaga   1260
atctcttgga cataggaatc tggatcaaga acaggtgaac taggttccag tttcggaact   1320
gggttaaagg gttctagaga ccagagtccg gagacaaaag cagtatcatc aaagacaaaa   1380
tcttcaatga aaccatcagg gatcatcaag tcttcaaata gatgtttctg tataacatcc   1440
aaatcagagc tttcctcaaa agtctccatt tcttcctctc tctttttttct ttagacaaga   1500
caggagaata agaaaaactg caagtggtgt ttgaagaaaa agttttgatg atattgttgg   1560
ctatataaag aaaggaatcc taaacatgtg ttaacgcagc catgggtgag gtgtcaaaag   1620
tctctctctg tgtctctctg gtttaactct gtggggccaa gtcttatcca ttaaacattt   1680
atggaggcaa cttaagatat tttgtcagga cccttcaagt tgtgccaact tgatcttgtc   1740
tatgatgctg acaaatttca ctaacatcca ttttattcct ctagagttta aaataccttg   1800
agctacccat ggttcgaatc ctaagctgaa tgctaacaaa atggtgatta ttttttttaa   1860
ctagaatttt gattgagttg gttaaggacg taggttcatt tgaaatttta aatctaaaac   1920
ataacacaaa ccaaaaccaa aaagacttga actactagtg tttataatcg taacttaagt   1980
cttaaaagc caatctctca aaagtttttt cttttttttt tttatcttaa aagttttatg   2040
ataagattga tatatgattt tcgtagtagt aatgactcac taggtaagct cttaaatatc   2100
aaaagatatt ttgcatattc acattcgagt aaaaagataa gagataatg actttcactc   2160
gaataaaaag gagagacaaa ttcatcaaat tgcttgtctt gtagggttgt cttgctagga   2220
tatgatttga agcaacttga tatttctttg tttctacata acttcgtata gggctccaca   2280
tatataataa ccaaaccta ccctcttgct cagttgcttg acaattatac tcctaatctc   2340
ataatctttt ataatagcat gtaagataat attaattatt tacttttatt gatgctttgt   2400
agataatctt cgacagcatt atccatttga ttggtgtttt ccactattga aattttgaat   2460
ttgtttagat ttgtatgtat ttttaactaa ttaattgtct tttcgttgca cactattttt   2520
ttatagctcc gatttacttt ttcctgatcc aattttataa tctattgact atttagcaga   2580
tatgaagtgt ttagatatgg acttaacgaa actgatgact aagaatgttt atacaatcaa   2640
taaatttata acatcaacaa atacaaaatt aaatttatat tttcaacatc caaatattct   2700
actaaaaaaa ataatgaata aaatgattgg tactaattaa actacttatt tgatatttgc   2760
acactaccgc tacctttata ttatacaaga ataaatgaaa tcatgagagt gacgcaagt    2819
```

<210> SEQ ID NO 202
<211> LENGTH: 428
<212> TYPE: DNA
<213> ORGANISM: Arabidopsis thaliana

<400> SEQUENCE: 202

```
ggatcctacg aaagtgagat ttgaccgaat aaccaggaag tactgtccct aatccatgaa      60
tcgtcttcag cttcggctgc agagtaatgg acgtgatcgt cgacgacgac gagagagcaa     120
tcgccattgt tgcttccaga gaaagctgaa ataataata atcccaattt aaaatcgaaa     180
tcgattttct cataccgttg gttaatctcg tggagttggg ttattacacg tgtcagatga     240
tgtaaccatg atctcagaga aaaagtcaca tgccacgtca gttaacttta gggcaaaatg     300
ggaaaagaat ctaaagagca tatgttcgtg cacgttcttg tttagggtaa gctcaaagct     360
caagccgctt ctatctctct acatttctct ttctgcaatg gcgagattag tgcgtgtggc     420
taggatcc                                                               428

<210> SEQ ID NO 203
<211> LENGTH: 1358
<212> TYPE: DNA
<213> ORGANISM: Arabidopsis thaliana

<400> SEQUENCE: 203 aagcttttc tctgcgaatt tctggaacca atcaaatcaa atttgtctct tttgtttatt      60
gtcgactttt ctgttttttt ctgttctggt attattcctc caagggactc ggaccggatg     120
gcaaaacttg accactttgc tcctggttca ggttgcggtt catggtcaac cttagacccg     180
acctatccgt ttcgttgatt tcattaatta gtctgcgttt tcttgggtgg agtgcagaca     240
gattttcttc tgcagtaggc gttaatccga taggctcttg ttgggcctca aatagttcag     300
taaacttttc gtggggcttt tagtatagcc catgtattaa taacaatatt acacttggga     360
aatgacaaaa aaaaaaaaga gaatgaagcg gtactcttat atcaaaaaaa catattgtat     420
atcttcgaat atgatgcaac tcatgcaaca acaatactag taggctacat gtattgctcc     480
atttaattac ataaacttaa atattctaat tcataaactt tcttttaatt atatatttta     540
tgtaagtttt aaatattgaa aaaaaaaaaa gttttaaata ttgaaacatg ataagttttt     600
acatccattt attataaaaa aaatagtgat gatgatgatc aaaattttga gtacatttta     660
gagtgtttta acttttacat ttgttgttac aattgttatg agtctgatat ttcaaatttc     720
gttttcaaag aaaaatcctg agtttacctt aaaagattaa agccagtttt taagaaataa     780
gtagaaaaat atcaaaccag acctagctga accaaaaatt atacaaaatc tagaccggat     840
taaaccggct acccgacgaa tatgcctagt aaaagtgtcg tcatcggaaa agaatctttt     900
acatggctga aaccgcaaat acgatcttca agagagcaac ataaaaatac ttgtcaaata     960
agtaaagaaa ataagacact caatatccac actcccaaac catgaaaata tgaatagaaa    1020
tctcaatgag ccaatcagag gccagcaaag tccatctcat tgtcccaagc ggatatacat    1080
ccgacaaaac tcaacctcac aagtagactc tcccttcttc cgtaactatt cgtccacgtg    1140
tccttccctc tcaccactta ccttcaaaac caacgcttct tttttagttc cttggtccga    1200
agcgtttacc gatgagagaa tcataaactc ccacttggag ctcaaaaagt gtaagagaca    1260
accaacaaaa aacgattcat ctcttctcct atcctctcct cttcgaattc aacgtttgga    1320
gaatccagca gccgcaaaat ggcttcgctt gtggatcc                           1358

<210> SEQ ID NO 204
<211> LENGTH: 24
<212> TYPE: DNA
<213> ORGANISM: Arabidopsis thaliana

<400> SEQUENCE: 204
gagacaaaaa gcttttctc tgcg                                              24
```

<210> SEQ ID NO 205
<211> LENGTH: 21
<212> TYPE: DNA
<213> ORGANISM: Arabidopsis thaliana

<400> SEQUENCE: 205
tcgcagaagt tgttgtaagt g                                          21

<210> SEQ ID NO 206
<211> LENGTH: 23
<212> TYPE: DNA
<213> ORGANISM: Arabidopsis thaliana

<400> SEQUENCE: 206
gtgaatggag gatccacaag cga                                        23

<210> SEQ ID NO 207
<211> LENGTH: 21
<212> TYPE: DNA
<213> ORGANISM: Arabidopsis thaliana

<400> SEQUENCE: 207
ttacatactg agggaagctc g                                          21

<210> SEQ ID NO 208
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 208
gttggttcgt cgactagaga aggt                                       24

<210> SEQ ID NO 209
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 209
ttggatccgg gaggcaatga tgctttag                                   28

<210> SEQ ID NO 210
<211> LENGTH: 470
<212> TYPE: DNA
<213> ORGANISM: Arabidopsis thaliana

<400> SEQUENCE: 210
aagcttagaa gctaaaagaa gccgcgaaga attgtgaaga agaaggaaag tttccattat    60
tgcctttat tttatttat ttaataattt aagggttttt gattttaaaa tgaataataa    120
taataaatac aaaaaagaaa ggacagaagg aaggagtgat gtgtggtaga gagagacagt   180
tcaccgtcgg cgagtccagc tggcggtggt gggagcccac cgtgtcacct taatcatcgc   240
tgcgctgccc tgtctttttt ccattattaa tttttagcaa gaagaagact gggctttcta   300
aattagttat taatgggctt tgggctttcg tggttagggt tgtgtagggg cttaatcgtc   360
atttcggaga tagaataaac cctaatctcc atgatgggc tctccgatgt ttgtcttttt   420
gattttgaa atttgatttt caaaaataaa ctaaagcatc attgcctccc                470

```
<210> SEQ ID NO 211
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 211
ttgtaagctt gcagggatac ggatgggtag                                    30

<210> SEQ ID NO 212
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 212
aaatattgga tcctttgggg ttctc                                         25

<210> SEQ ID NO 213
<211> LENGTH: 1569
<212> TYPE: DNA
<213> ORGANISM: Arabidopsis thaliana

<400> SEQUENCE: 213
aagcttgcag ggatacggat gggtagcttt caaaacttac atcatcttct gtttcttgag   60
atcaactatt tttggagctt tgtctcaatc gtaccaaagg ataatggtcc tacctccttt  120
tgcattctta actttatctt ctctacttat ttcttttttg ggattttgg gggtattatt   180 ttatcttttg tagatataca cattgattta ctacaaacgt atactactat ccatcttcaa  240
ctcttcggaa tatgatttcg aaaaaactat gaagattaac gggtatctta acatgttaa   300 gatacaccgg acaattttca tttagaagaa ttgatatgca attaacaata aatagttgat  360
gatcttttag ttttgaagat gtgcgttaag acttaagcgt gtggtaacaa ggtgggactc  420
gggcaacgca aagccttgta gagtccactt gctcaacttg tctttctttt atctcttttc  480
caagtctcaa gattcaatga actccgtgta acacaaacac gcccatagat gagctcattt  540
ttggtatttc caatattgcc actccatgat aatatcatct agggatgggg ttcatttatt  600
ttgaaatctc aacaaatctc gtcgattcta acacacatga ttgatttgtt tacttacttg  660
aaagttggca actatctggg attaaaattt atcttttttct actgctagct agaagcatct  720
atatatgtta gcctaatacg tggaagatgt cattgctaat aatggctaaa gatgtgtatt  780 aattttctt cttttttcct tgaatttttg ttctttgaca taaactatgc tgtcaaaatg   840
tgtagaatct tttacataa atcattccct gttacacact aaaaggttca aacggacga    900 ttgtattgga cttccagatc ataaaccatg caaaactgaa accacaaga ataattagtt   960 ctaactttag aacgttcgta cgtgtttcat gttcaaaaag cgtcaattat aaaagttggg  1020
aaattacttt tgagttttga catttctaag gacagtcaaa tatgacaaca ttgggatgca  1080
acttaccttg tattaactta ttttgttata aaccatata ttacatattt taagggttg    1140 ataaataatc aaatatacca aaacatagct tttcaatata tttgtaaaac cgtttggtc   1200 tactagctaa ttatgagaac atttgttcaa tgcatgatta tctagtatct actagtggat  1260
tatgaaaatt agatattttc attgcatgat tatcttccat atatagtgat aacatcaaaa  1320
gaatctacac caattattgc attttttcat tatataataa gcactaaact gtaaaattat  1380
attcagccac ccaaaccatg acaaatcacc ttaaaggctt aaacacataa cagccattac  1440
```

```
gagtcacagg taagggtata atagtaaaga atcaatctat ataatatacg acccacccct    1500
tctcattctt tctggagagt aacatcgaga caaagaagaa aaactaaaaa agagaacccc    1560
aaaggatcc                                                            1569

<210> SEQ ID NO 214
<211> LENGTH: 2000
<212> TYPE: DNA
<213> ORGANISM: Arabidopsis thaliana

<400> SEQUENCE: 214
ggttaaagaa tgatgattcg attatagcct caactagaag atacgtgtag tgcaggtgtg      60
tagttaactg gtggtagtgg cagacaacca gattaggagt taaataaagc ctttagattt     120
gagagattga aatattcgat tggaaccttt ctagattttt acagccatct aaaattagat     180
gcagatcacc tactaccatt caaaaatgaa caaaataatt tcatttacat tttcctagca     240
taagatataa aataaaaata gtgctcattt taattacttt ttctaaatat tttcgttatt     300
ttaaattttg cttgtctata ctctacagct catttaataa cggaaacaaa ataattgca     360 gggatacgga tgggtagctt tcaaaactta catcatcttc tgtttcttga gatcaactat     420
ttttggagct ttgtctcaat cgtaccaaag gataatggtc ctacctcctt ttgcattctt     480
aactttatct tctctactta tttcttttt gggattttg ggggtattat tttatctttt      540
gtagatatac acattgattt actacaaacg tatactacta tccatcttca actcttcgga     600
atatgatttc gaaaaaacta tgaagattaa cgggtatctt aaacatgtta agatacaccg     660
gacaattttc atttagaaga attgatatgc aattaacaat aaatagttga tgatctttta     720
gttttgaaga tgtgcgttaa gacttaagcg tgtggtaaca aggtgggact cgggcaacgc     780
aaagccttgt agagtccact tgctcaactt gtctttcttt tatctctttt ccaagtctca     840
agattcaatg aactccgtgt aacacaaaca cgcccataga tgagctcatt tttggtattt     900
ccaatattgc cactccatga taatatcatc tagggatggg gttcatttat tttgaaatct     960
caacaaatct cgtcgattct aacacacatg attgatttgt ttacttactt gaaagttggc    1020
aactatctgg gattaaaatt tatcttttc tactgctagc tagaagcatc tatatatgtt     1080
agcctaatac gtgaagatg tcattgctaa taatggctaa agatgtgtat taatttttct     1140
tcttttttcc ttgaattttt gttctttgac ataaactatg ctgtcaaaat gtgtagaatc    1200 ttttttacata aatcattccc tgttacacac taaaaggttc acaacggacg attgtattgg    1260
acttccagat cataaaccat gcaaaactga aaccacaag aataattagt tctaacttta     1320
gaacgttcgt acgtgtttca tgttcaaaaa gcgtcaatta taaagttgg gaaattactt     1380 ttgagttttg acatttctaa ggacagtcaa atatgacaac attgggatgc aacttacctt    1440
gtattaactt attttgttat aaaccatat attacatatt ttaaagggtt gataaataat     1500
caaatatacc aaaacatagc ttttcaatat atttgtaaaa cacgtttggt ctactagcta    1560
attatgagaa cattttgttca atgcatgatt atctagtatc tactagtgga ttatgaaaat    1620 attatttt cattgcatga ttatcttcca tatatagtga taacatcaaa agaatctaca     1680
ccaattattg catttttttca ttatataata agcactaaac tgtaaaatta tattcagcca    1740
cccaaaccat gacaaatcac cttaaaggct taaacacata acagccatta cgagtcacag    1800
gtaagggtat aatagtaaag aatcaatcta tataatatac gacccacccct ttctcattct    1860 ttctggagag taacatcgag acaaagaaga aaaactaaaa aagagaaccc caagaatcg     1920
```

```
aatatttatt atttcgcccc gaagattcta tttctgatca tttacacccc taaaaagagt    1980
agagctttcg tgaagccacc                                                2000
```